(12) United States Patent
Komuro et al.

(10) Patent No.: US 9,427,457 B2
(45) Date of Patent: Aug. 30, 2016

(54) WNT SIGNALING INHIBITOR COMPRISING INSULIN-LIKE GROWTH FACTOR-BINDING PROTEIN

(71) Applicant: National University Corporation Chiba University, Chiba (JP)

(72) Inventors: Issei Komuro, Chiba (JP); Ichiro Shiojima, Chiba (JP); Weidong Zhu, Chiba (JP)

(73) Assignee: National University Corporation Chiba University, Chiba (JP)

( * ) Notice: Subject to any disclaimer, the term of this patent is extended or adjusted under 35 U.S.C. 154(b) by 0 days.

(21) Appl. No.: 14/633,155

(22) Filed: Feb. 27, 2015

(65) Prior Publication Data

US 2015/0164987 A1 Jun. 18, 2015

Related U.S. Application Data

(62) Division of application No. 12/988,533, filed as application No. PCT/JP2009/058045 on Apr. 23, 2009, now abandoned.

(30) Foreign Application Priority Data

Apr. 25, 2008 (JP) ................. 2008-115342

(51) Int. Cl.
| | |
|---|---|
| *A61K 38/17* | (2006.01) |
| *A61K 31/7088* | (2006.01) |
| *A61K 48/00* | (2006.01) |
| *C07K 14/47* | (2006.01) |
| *C12N 15/113* | (2010.01) |
| *C12N 5/09* | (2010.01) |
| *A61K 38/00* | (2006.01) |

(52) U.S. Cl.
CPC ......... *A61K 38/1754* (2013.01); *A61K 31/7088* (2013.01); *A61K 48/005* (2013.01); *C07K 14/4743* (2013.01); *C12N 5/0693* (2013.01); *C12N 15/113* (2013.01); *C12N 15/1138* (2013.01); *A61K 38/00* (2013.01); *C12N 2310/14* (2013.01); *C12N 2501/105* (2013.01)

(58) Field of Classification Search
None
See application file for complete search history.

(56) References Cited

U.S. PATENT DOCUMENTS

| | | |
|---|---|---|
| 6,004,775 A | 12/1999 | Shimasaki et al. |
| 6,395,890 B1 | 5/2002 | Sheppard et al. |
| 8,293,529 B2 | 10/2012 | Koshimizu et al. |
| 2005/0148509 A1 | 7/2005 | Dake et al. |
| 2007/0204351 A1 | 8/2007 | Davidson et al. |
| 2011/0034381 A1 | 2/2011 | Kleinberg et al. |
| 2011/0243899 A1 | 10/2011 | Komuro et al. |

FOREIGN PATENT DOCUMENTS

| | | |
|---|---|---|
| WO | 99/55359 A1 | 11/1999 |
| WO | 2007/070964 A1 | 6/2007 |
| WO | 2008/137641 A2 | 11/2008 |

OTHER PUBLICATIONS

Wood et al., "Targeted Knockdown of Insulin-Like Growth Factor Binding Protein-2 Disrupts Cardiovascular Development in Zebrafish Embryos," Molecular Endocrinology, vol. 19, No. 4, Apr. 2005, pp. 1024-1034.

Zhu et al., "IGFBP-4 is an inhibitor of canonical Wnt signalling required for cardiogenesis," Nature, vol. 454, Jul. 17, 2008, pp. 345-350.

Hwa et al., "The Insulin-Like Growth Factor-Binding Protein (IGFBP) Superfamily," Endocrine Reviews, vol. 20, No. 6, 1999, pp. 761-787.

*Primary Examiner* — Marianne P Allen
(74) *Attorney, Agent, or Firm* — Kilyk & Bowersox, P.L.L.C.

(57) ABSTRACT

Provided is a novel soluble factor that modulates morphogenesis and cell proliferation, such as cardiac development and/or cardiomyocyte differentiation. Specifically provided are: an inhibitor of Wnt signalling, comprising an insulin-like growth-factor-binding protein (IGFBP), the protein being binding to a Wnt receptor, and/or a polynucleotide encoding the protein; a medicament for prevention and/or treatment of a disease due to enhanced Wnt signalling, comprising the inhibitor of Wnt signalling, and a medicament for induction of cardiomyocyte differentiation; and a method for prevention and/or treatment of a disease due to enhanced Wnt signalling and a method of inducing cardiomyocyte differentiation, the methods each comprising using the inhibitor of Wnt signalling, and a cardiomyocyte, which is obtained by the method of inducing cardiomyocyte differentiation, and a use thereof.

2 Claims, 24 Drawing Sheets

Figure 1-a
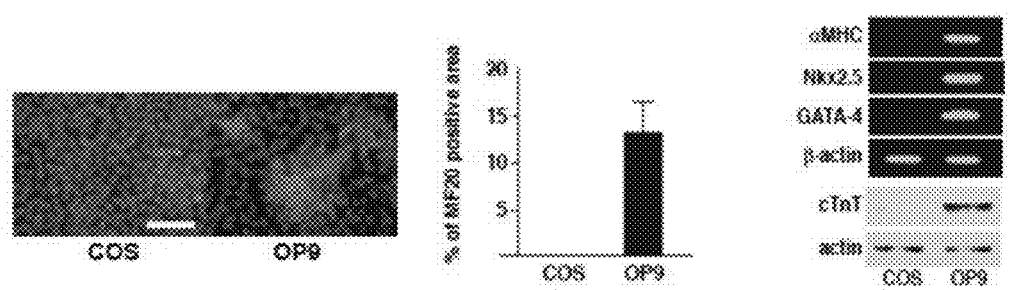
Figure 1-b
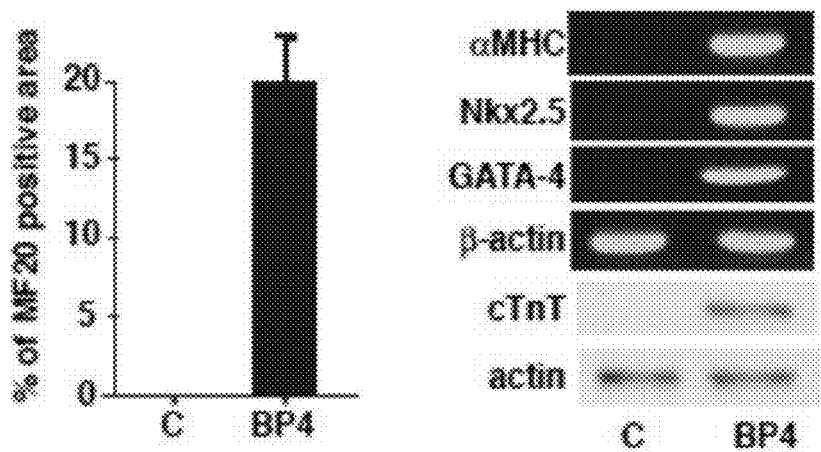

Figure 1-c
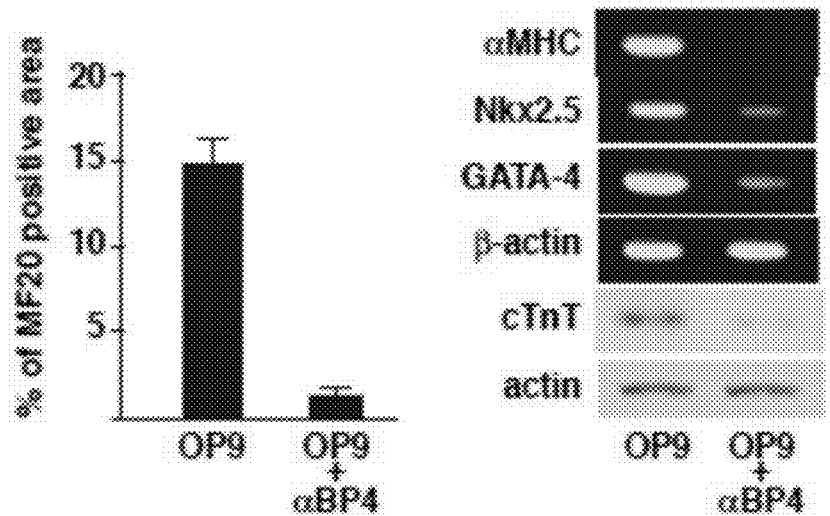
Figure 1-d
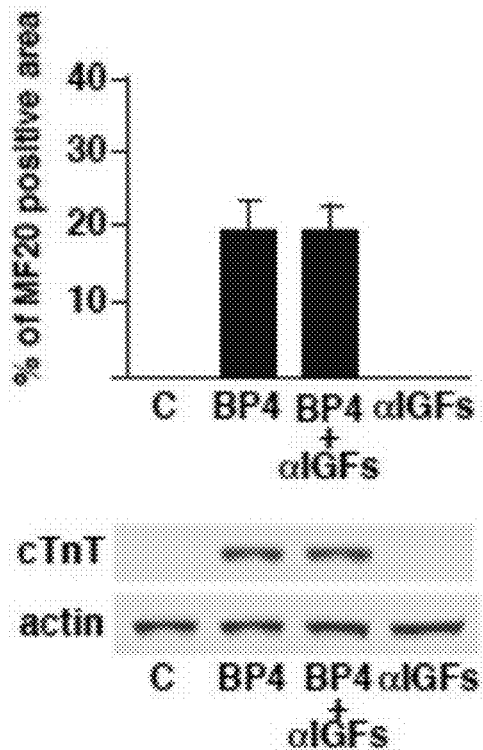

Figure 1-e
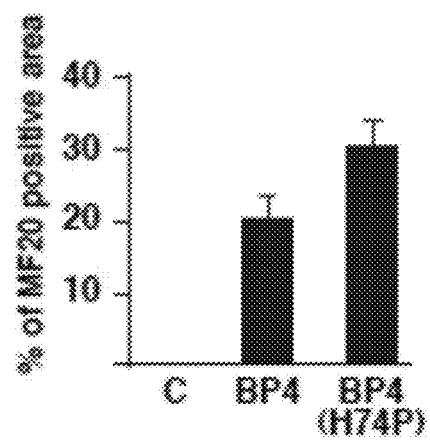

Figure 1-f
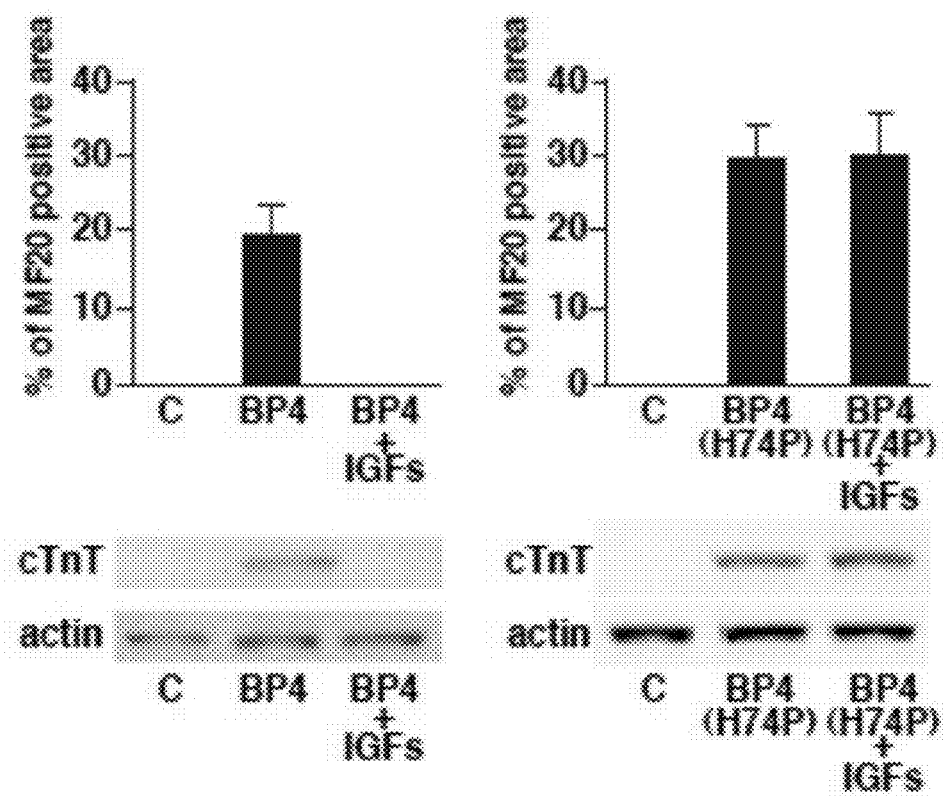

Figure 2-a
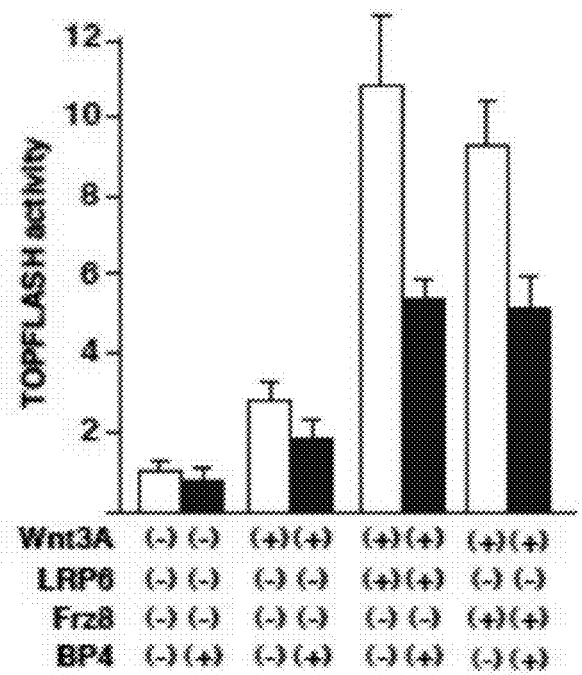
Figure 2-b
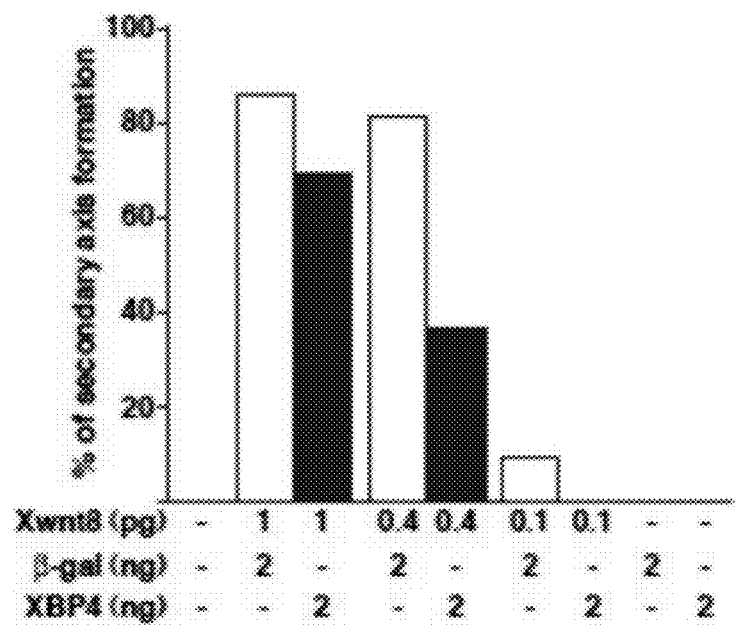

Figure 2-c
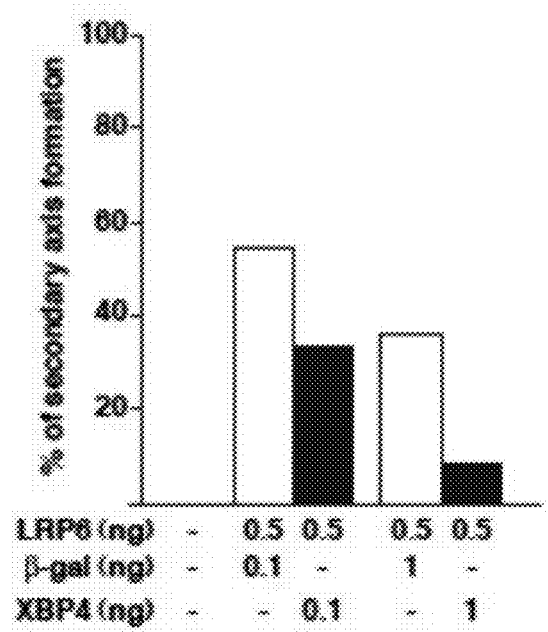
Figure 2-d
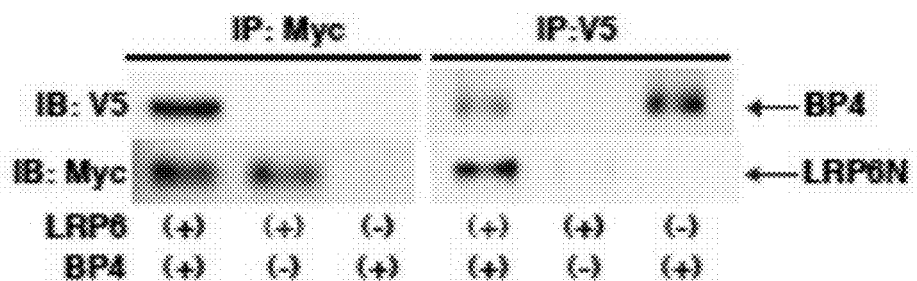
Figure 2-e
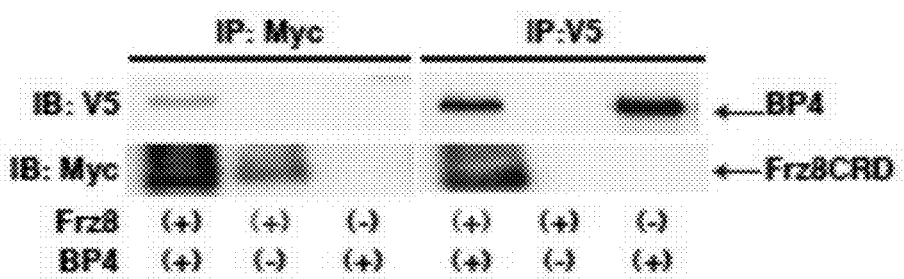

Figure 2-f
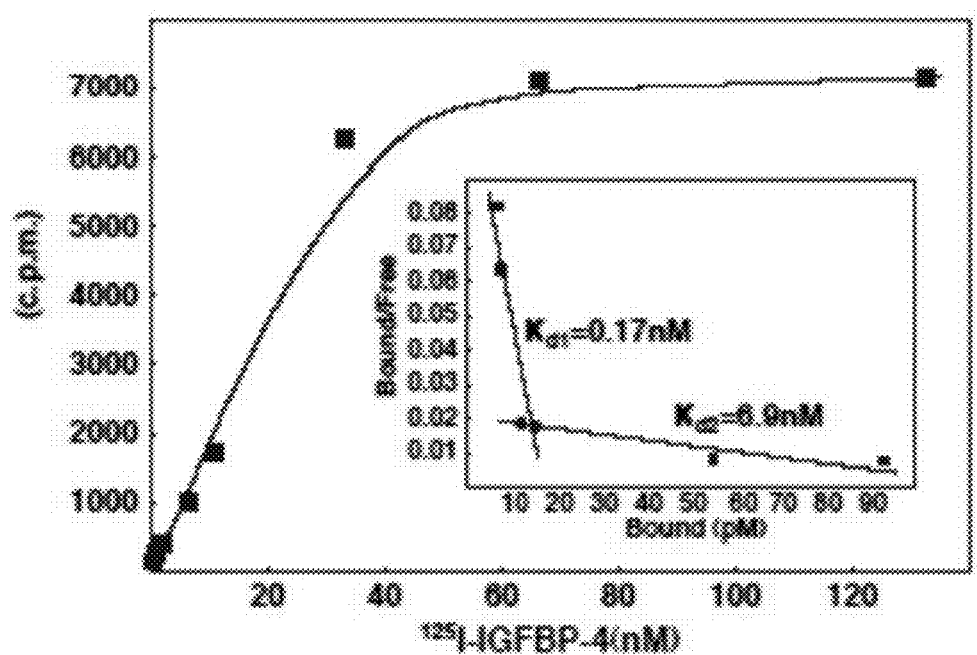
Figure 2-g
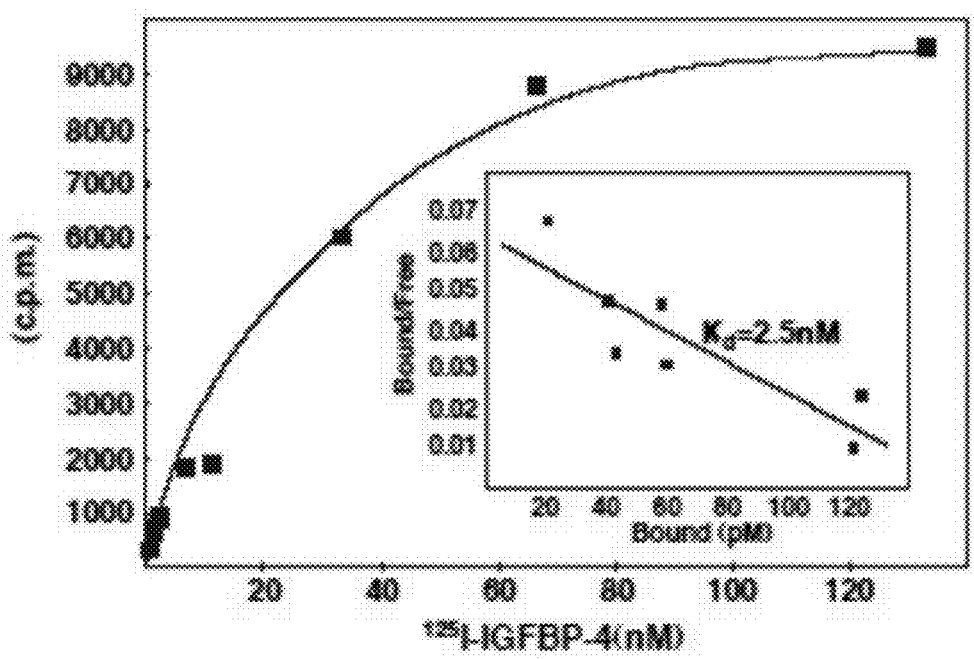

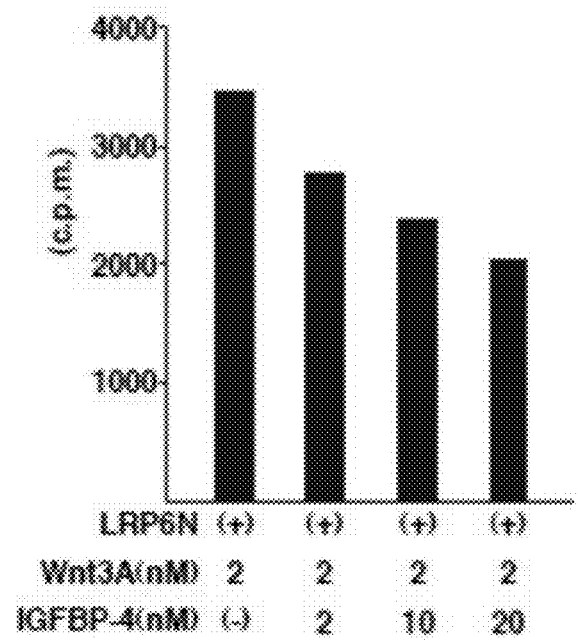
Figure 2-h
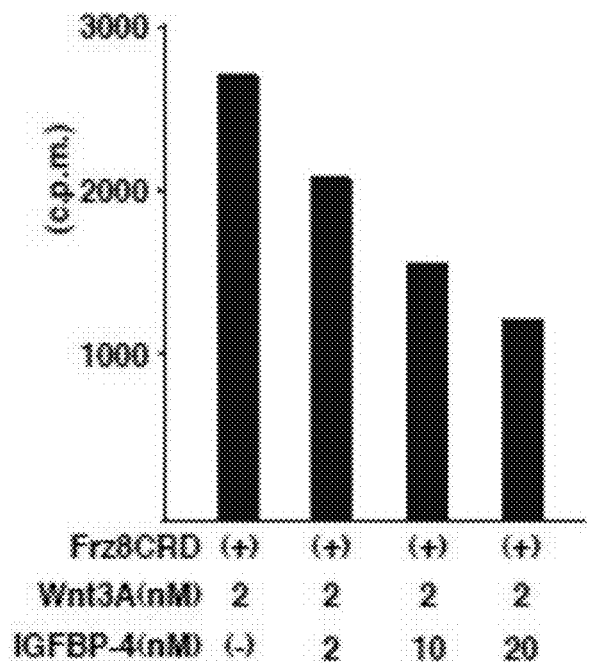
Figure 2-i

Figure 3-a
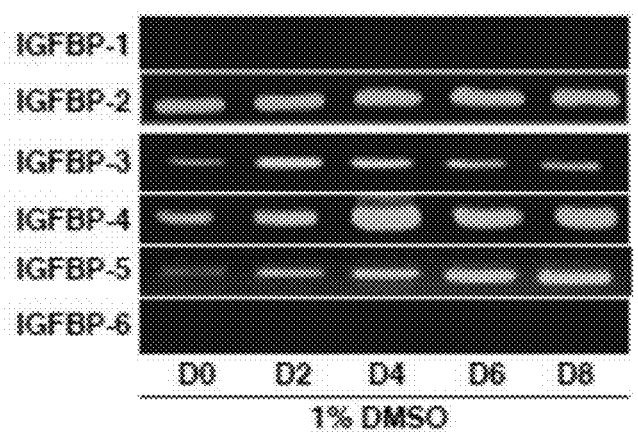
Figure 3-b
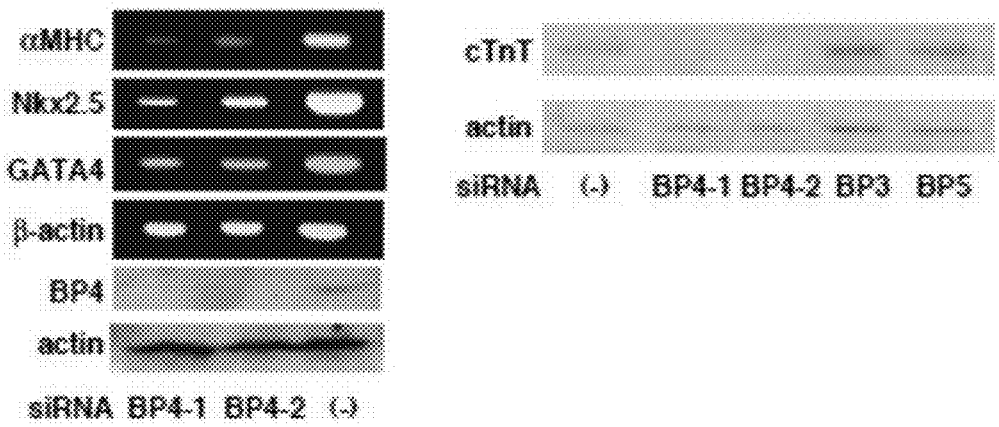

Figure 3-c
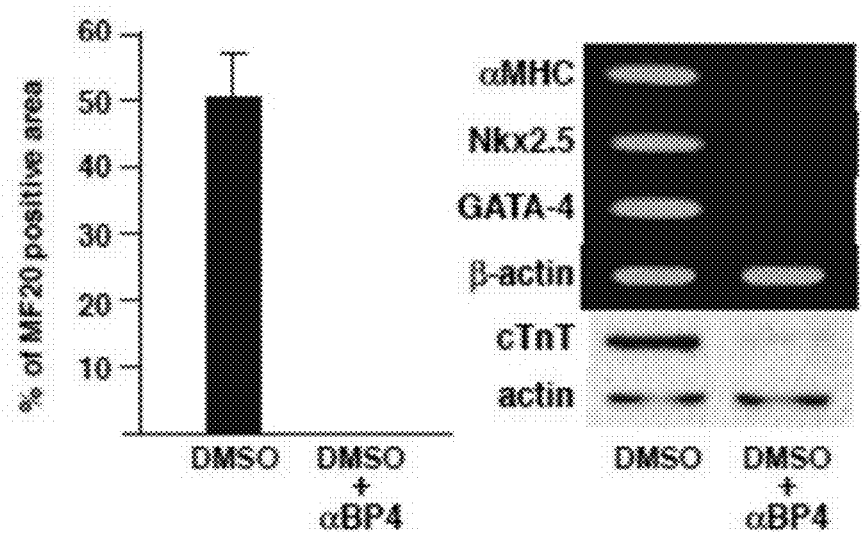

Figure 3-d
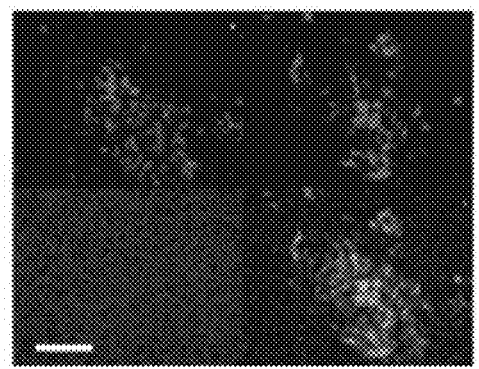
Figure 3-e
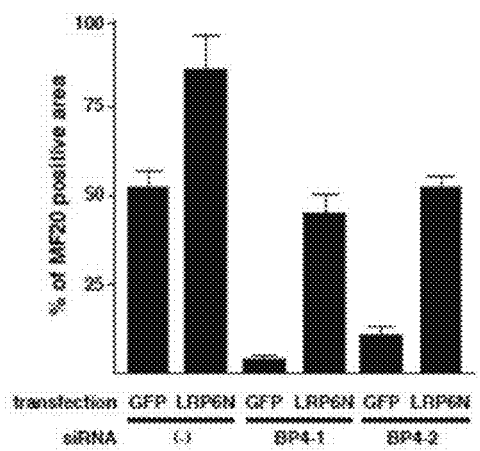
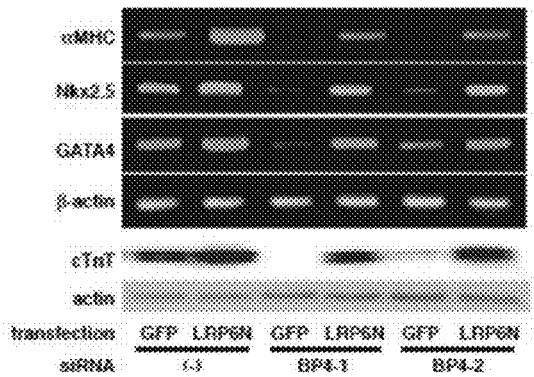

Figure 4-a
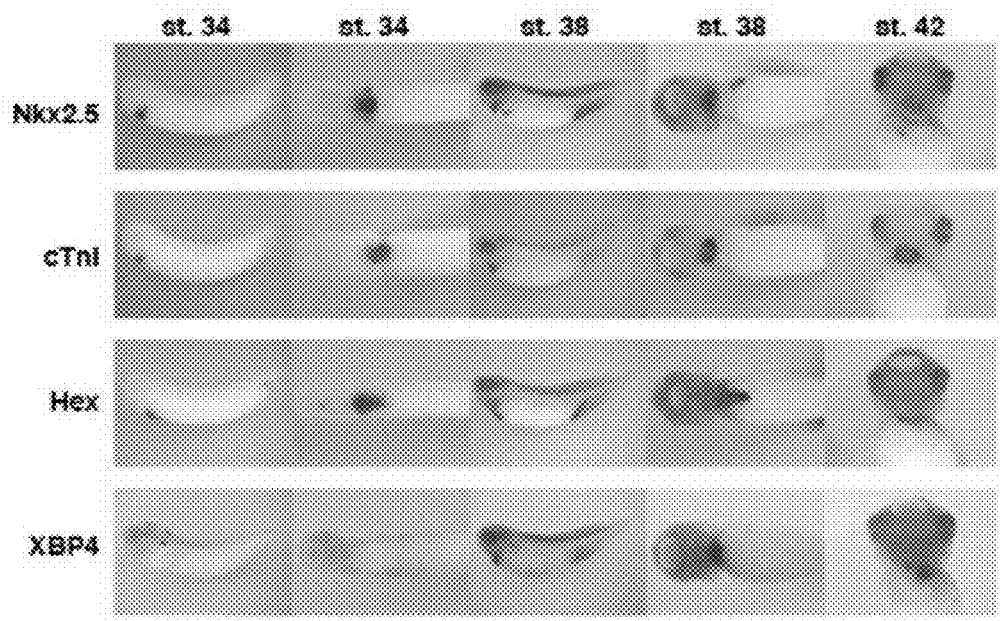
Figure 4-b
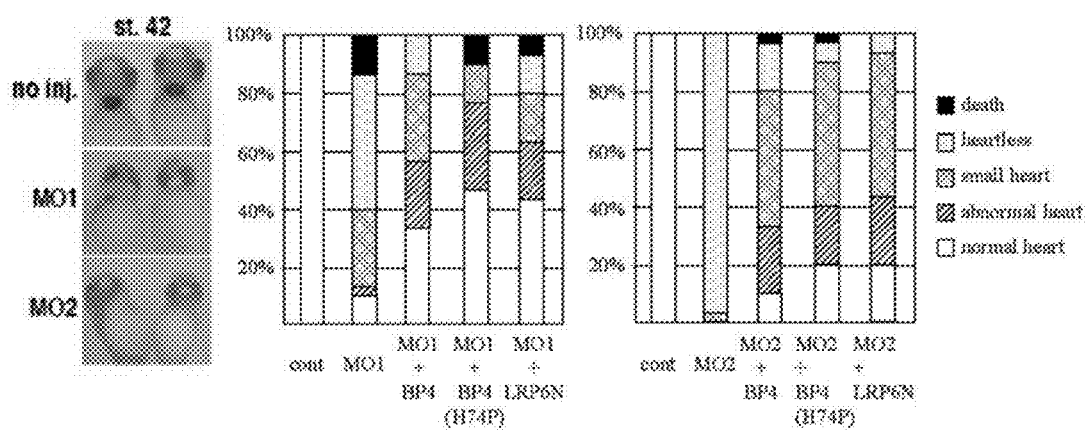

Figure 4-c
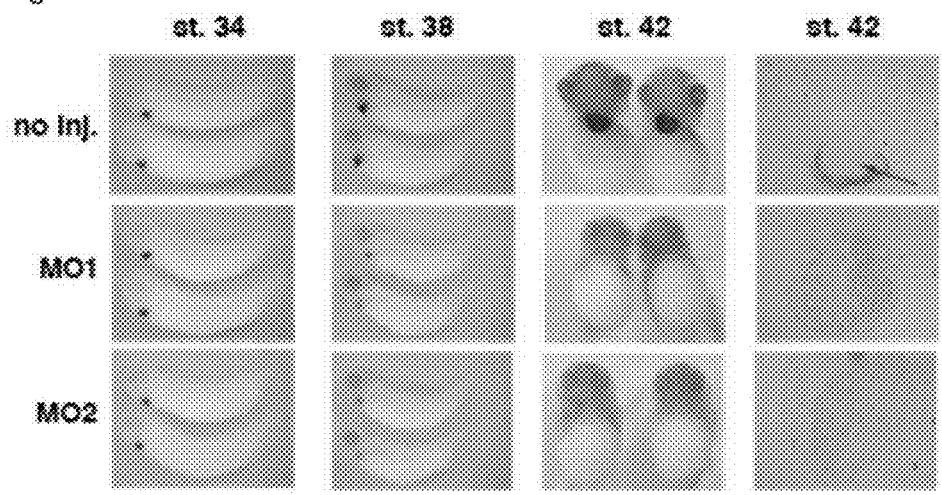
Figure 5-a
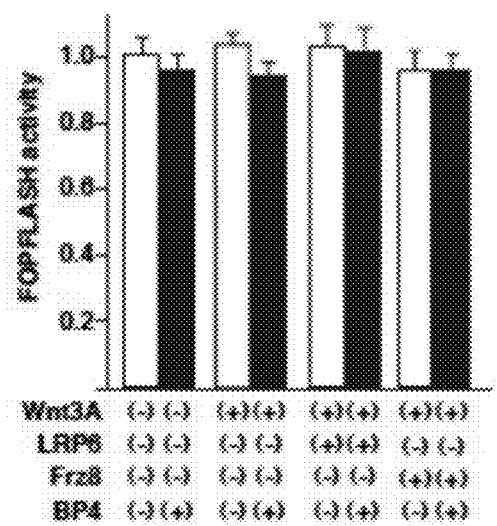

Figure 5-b
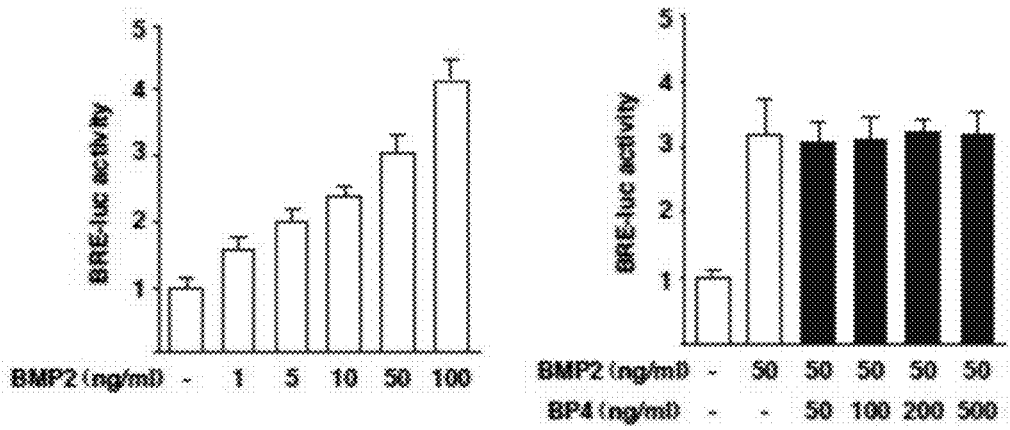
Figure 5-c
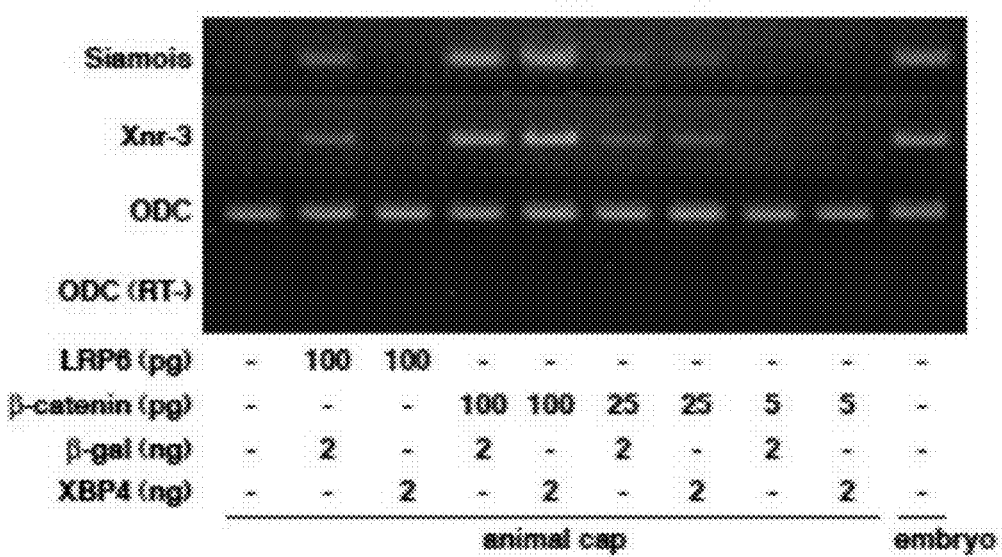
Figure 5-d
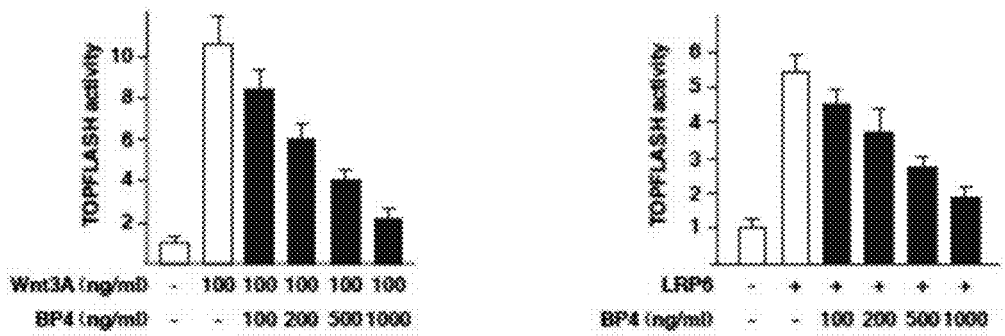

Figure 5-e
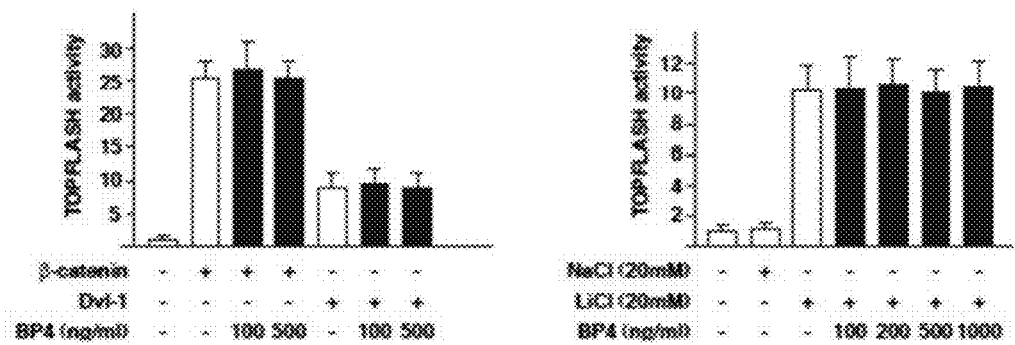
Figure 6-a
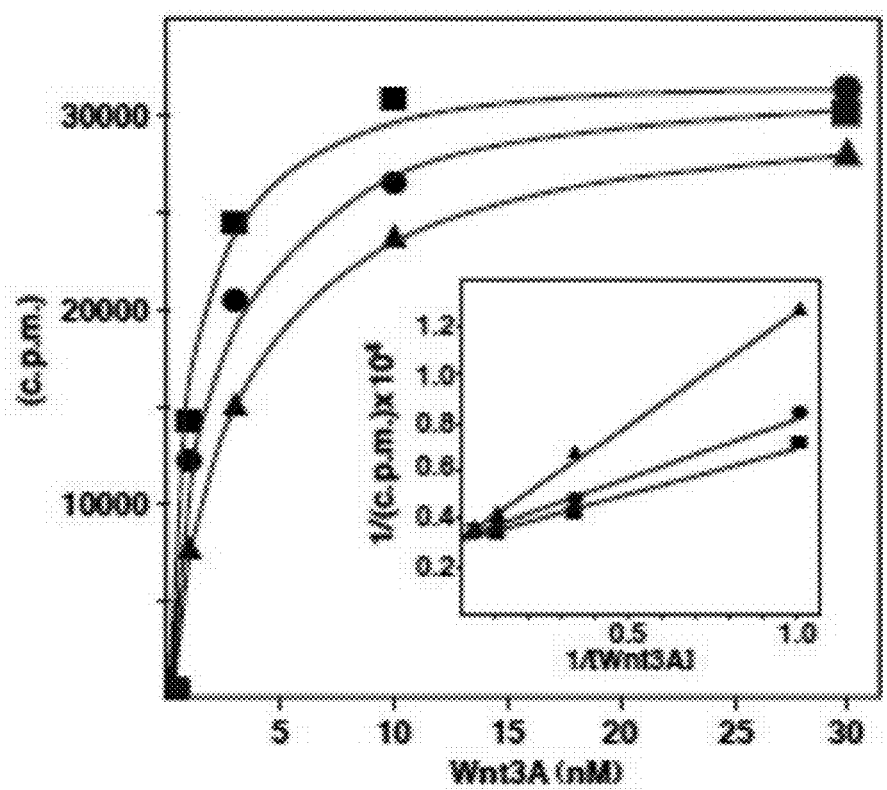

Figure 6-b
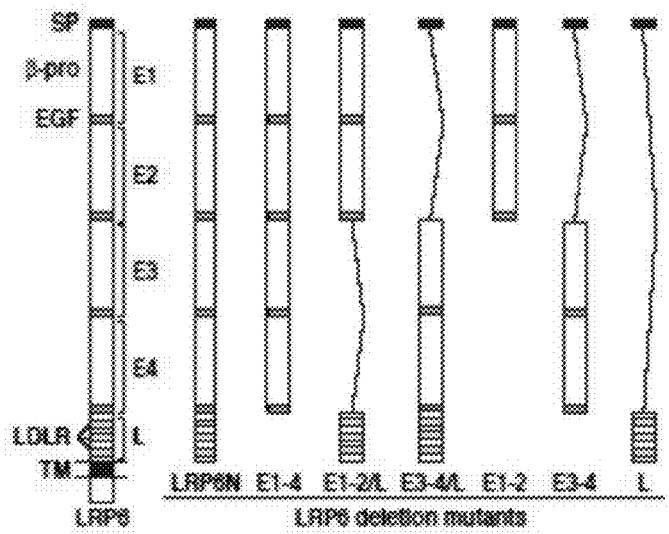
Figure 6-c
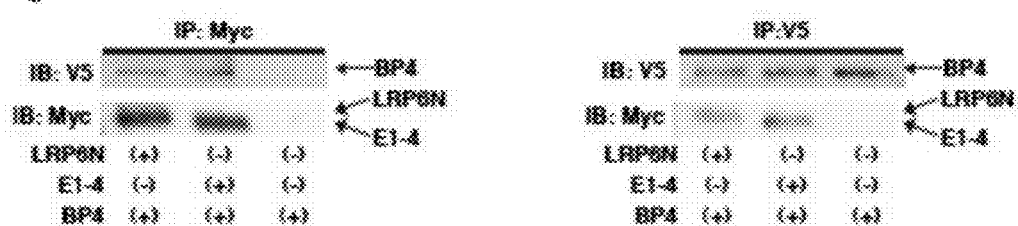
Figure 6-d
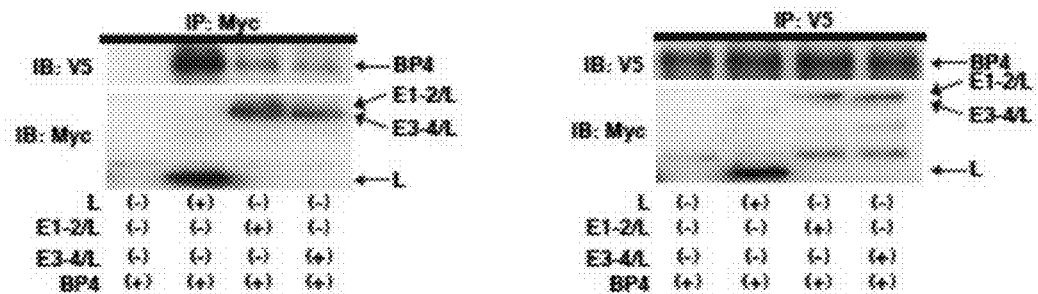

Figure 6-e
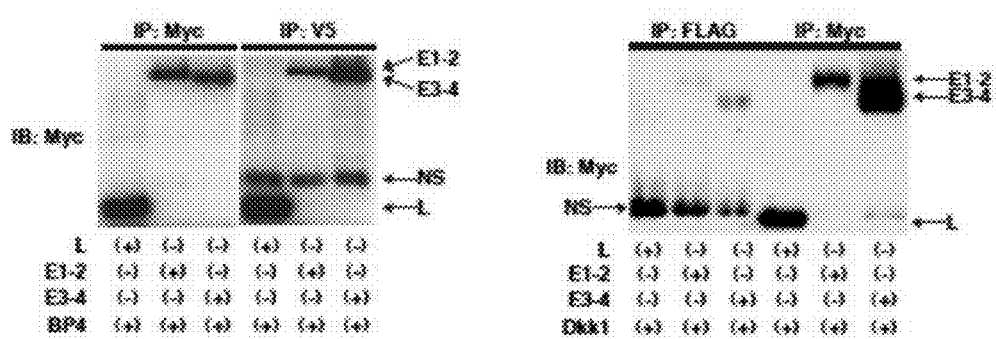
Figure 6-f
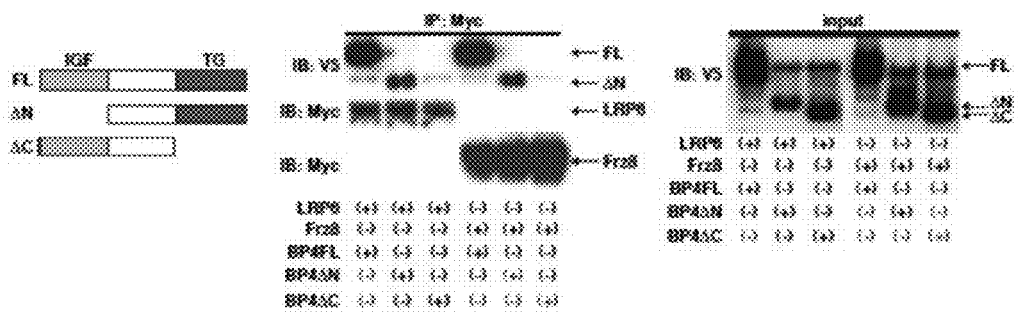

Figure 7-a
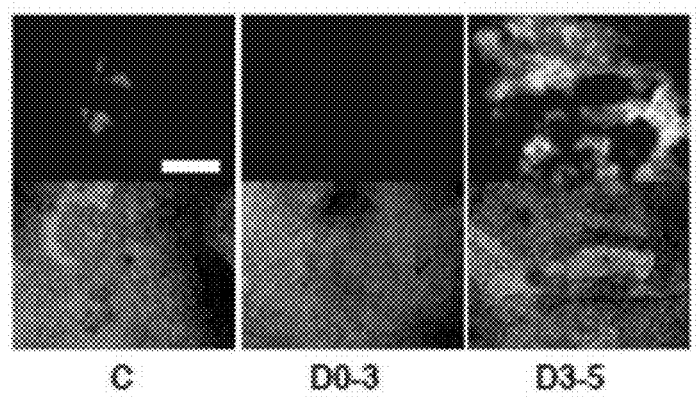
Figure 7-b
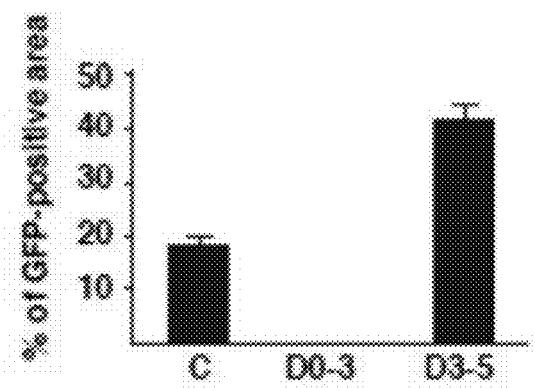
Figure 7-c
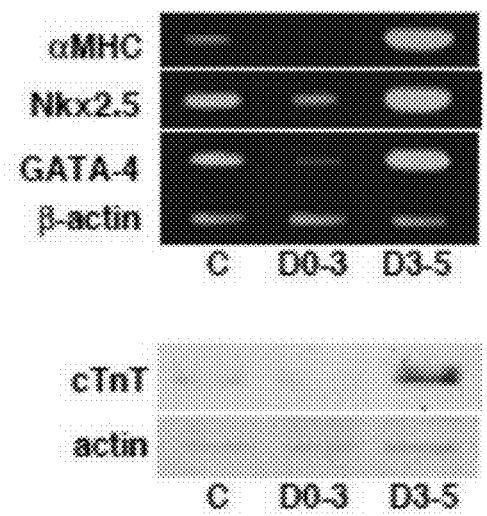

Figure 7-d
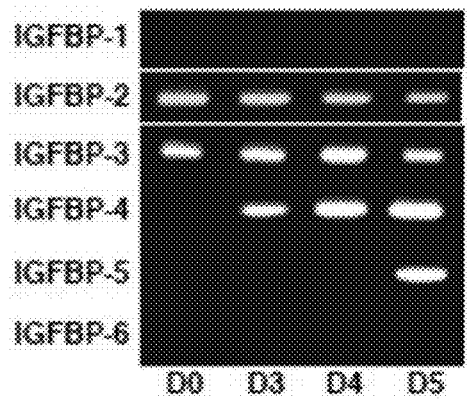
Figure 7-e
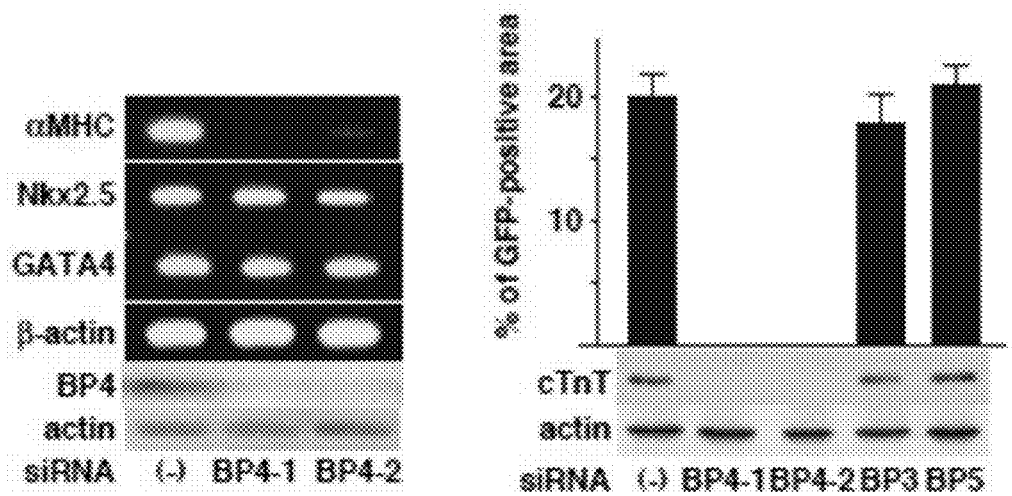
Figure 7-f
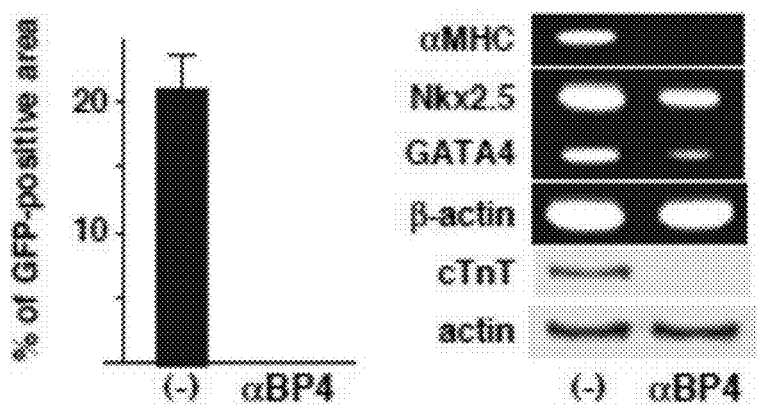

Figure 7-g
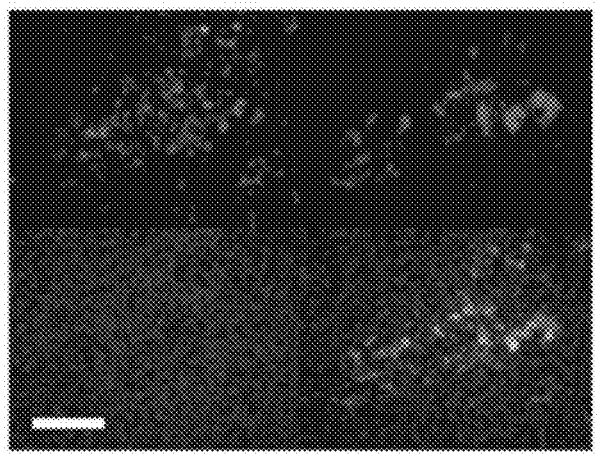
Figure 7-h
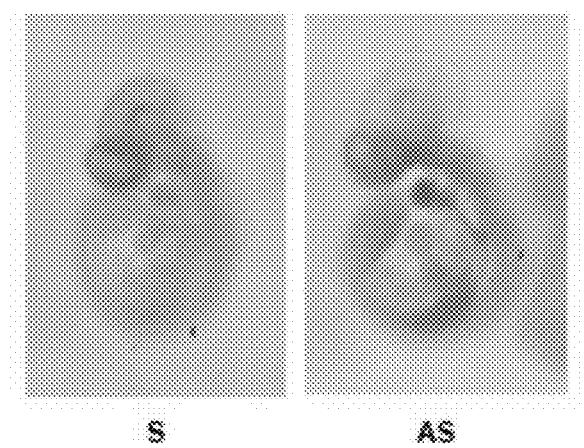
S       AS
Figure 8-a

Figure 8-b
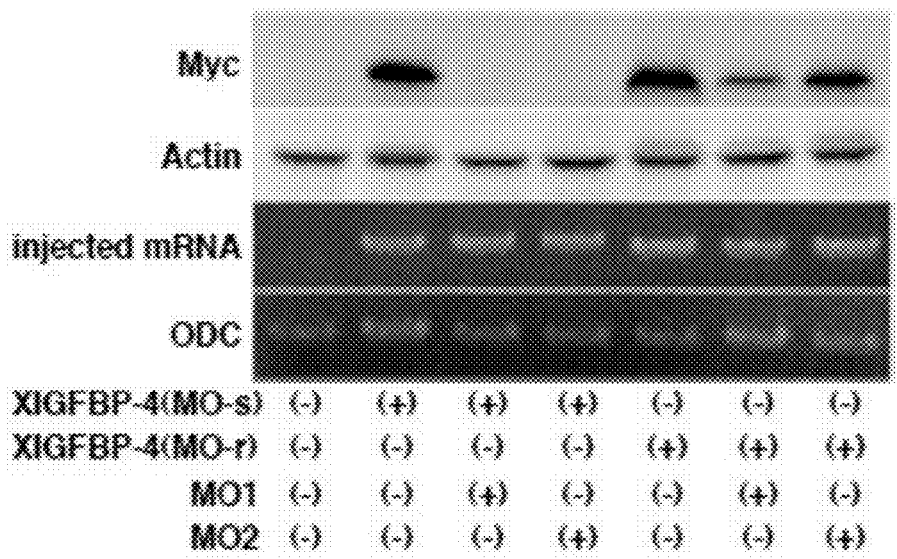
Figure 8-c
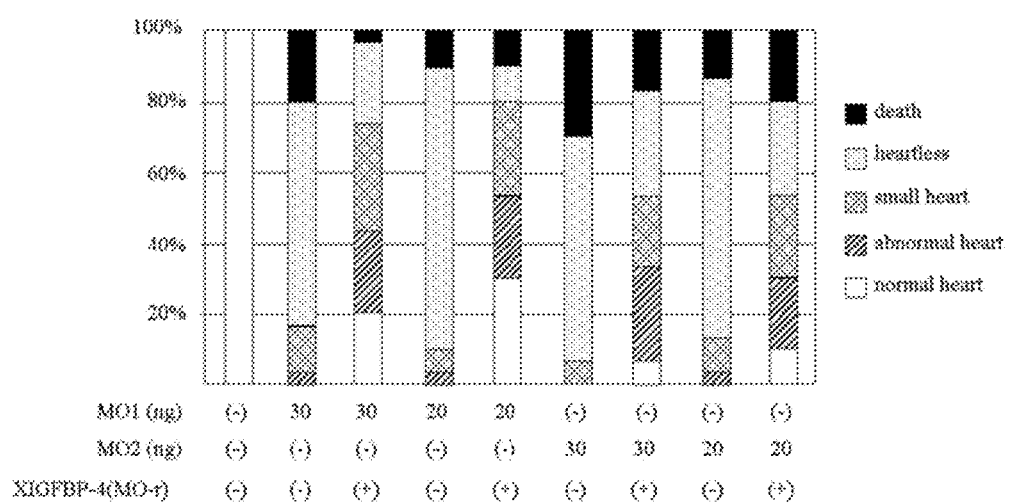

Figure 8-d
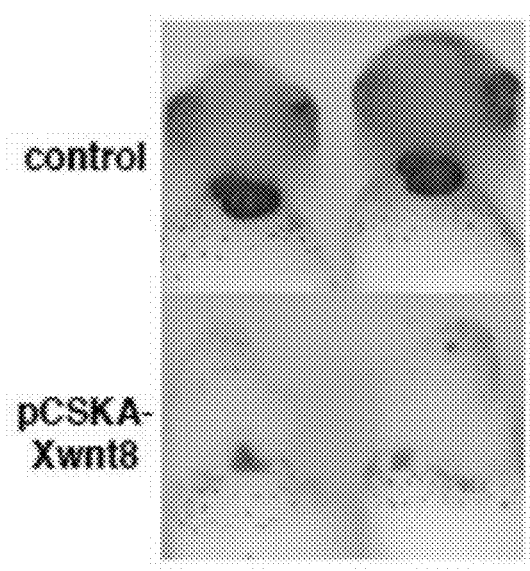
Figure 8-e
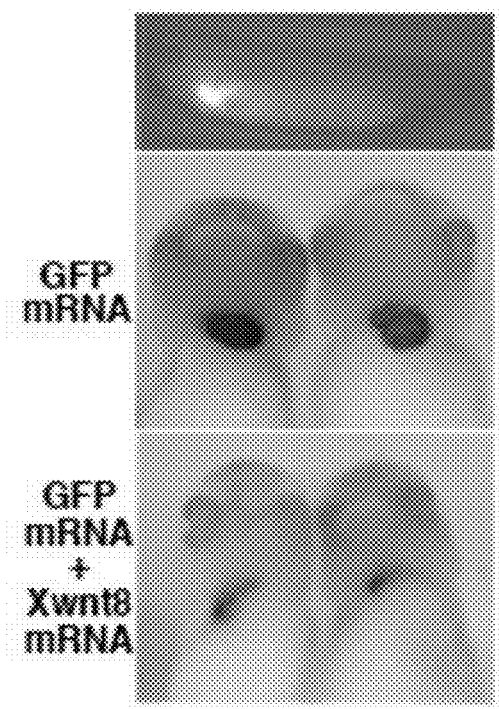

Figure 8-f
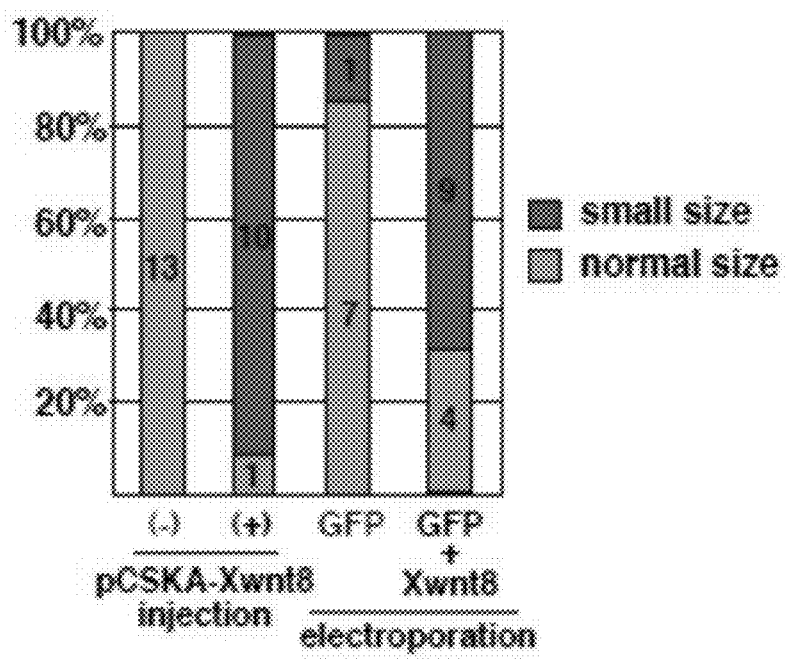
Figure 9-a
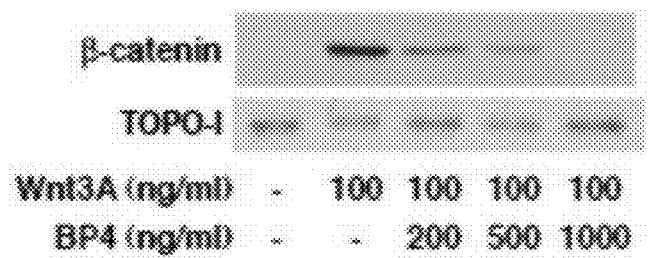
Figure 9-b
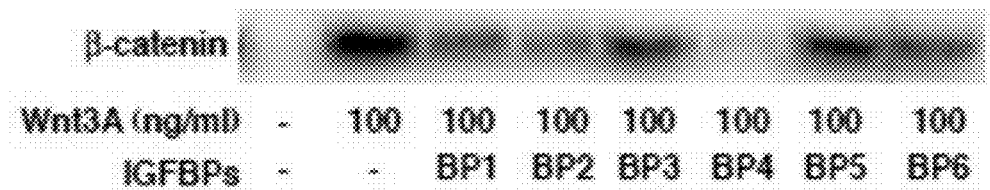

Figure 9-c
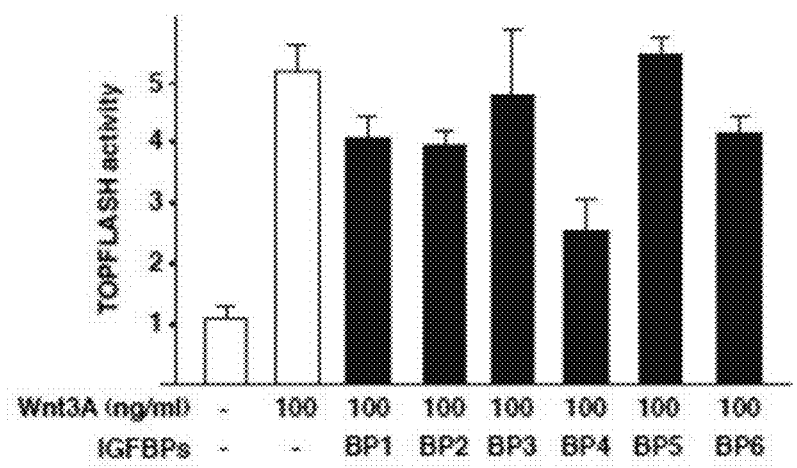
Figure 9-d
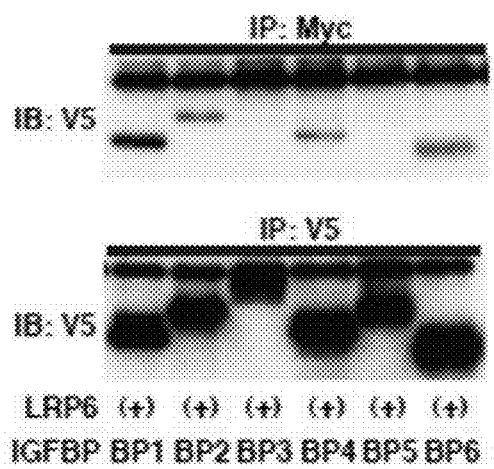
Figure 9-e
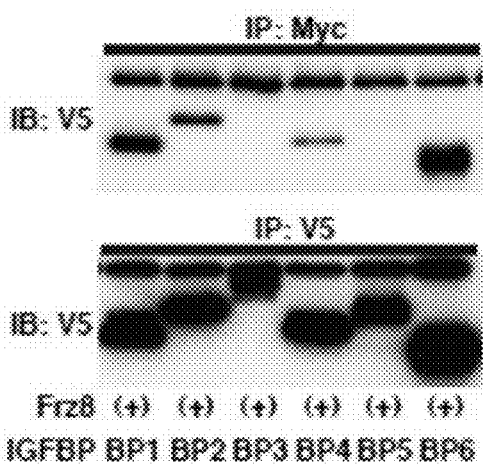

WNT SIGNALING INHIBITOR COMPRISING INSULIN-LIKE GROWTH FACTOR-BINDING PROTEIN

This application is a divisional application of U.S. patent application Ser. No. 12/988,533, filed Oct. 19, 2010, which is a National Stage Application of PCT/JP2009/058045, filed Apr. 23, 2009, which claims priority to Japanese Patent Application No. 2008-115342, filed Apr. 25, 2008.

TECHNICAL FIELD

The present invention relates to an inhibitor of Wnt signalling, comprising an insulin-like growth-factor-binding protein (hereinafter, sometimes abbreviated as IGFBP). The present invention also relates to an inhibitor of Wnt signalling, comprising a polynucleotide encoding IGFBP. The present invention also relates to a method of inhibiting Wnt signalling, comprising using IGFBP. The present invention also relates to a method of inhibiting Wnt signalling, comprising using a polynucleotide encoding IGFBP. The present invention also relates to a use of IGFBP and/or a polynucleotide encoding IGFBP in the manufacture of an inhibitor of Wnt signalling. The present invention also relates to a medicament for the prevention and/or treatment of a disease due to enhanced Wnt signalling, comprising the inhibitor of Wnt signalling. The present invention also relates to a method for the prevention and/or treatment of a disease due to enhanced Wnt signalling, comprising administering the inhibitor of Wnt signalling. The present invention also relates to a use of the inhibitor of Wnt signalling in the prevention and/or treatment of a disease due to enhanced Wnt signalling. The present invention also relates to a medicament for the induction of cardiomyocyte differentiation, comprising the inhibitor of Wnt signalling. The present invention also relates to a method of inducing cardiomyocyte differentiation, comprising bringing the inhibitor of Wnt signalling into contact with a cell capable of differentiating into a cardiomyocyte. The present invention also relates to a method of inducing cardiomyocyte differentiation, comprising administering the inhibitor of Wnt signalling. The present invention also relates to a cardiomyocyte, which is obtained by the method of inducing cardiomyocyte differentiation, and a use thereof.

BACKGROUND ART

The heart is the first organ to form during embryogenesis, and abnormalities in this process result in congenital heart diseases, the most common cause of birth defects in humans (Non-Patent References 1 and 2). Molecules that mediate cardiogenesis are of particular interest because of their potential use for cardiac regeneration (Non-Patent References 3 and 4).

Previous studies have shown that soluble factors such as Wnts, Wnt inhibitors, bone morphogenetic proteins (hereinafter, abbreviated as BMPs), and fibroblast growth factors (hereinafter, abbreviated as FGFs) mediate tissue interactions that are crucial for cardiomyocyte specification (Non-Patent References 2 and 4).

Wnts are proteins that control morphogenesis, and are known to be involved in various phenomena such as development, stem cell differentiation control, and cell malignant transformation. Further, there are reports that Wnts are important factors for the growth regulation and survival of stem cells (Non-Patent References 5 and 6).

It is known that Wnts bind to cell membrane receptors and transmit intracellular signals via at least three kinds of pathways, to thereby express their actions. Known as the cell membrane receptors to which Wnts bind are Frizzled (sometimes abbreviated as Frz) as a seven-pass transmembrane receptor and low-density lipoprotein receptor-related proteins 5 and 6 (sometimes abbreviated as LRP5 and LRP6, respectively) as single-pass transmembrane receptors (Non-Patent References 7 and 8). It is conceivable that there are at least three kinds of pathways in signalling pathways to be controlled by Wnts, i.e., a β-catenin pathway, a planar cell polarity (PCP) pathway, and a calcium ion ($Ca^{2+}$) pathway. The β-catenin pathway has been known for many years and is also called a canonical pathway. The pathway is characterized by the stabilization of cytoplasmic β-catenin that plays an important role in the transmission of Wnt signals to the nucleus. The abnormal activation of the pathway is thought to be associated with oncogenesis. On the other hand, the PCP pathway and the $Ca^{2+}$ pathway are called non-canonical pathways. The PCP pathway is characterized by the activation of a low molecular weight G protein Rho and Jun kinase belonging to the MAP kinase family. Further, the $Ca^{2+}$ pathway is characterized by the activation of downstream protein kinases, protein kinase C (PKC) and calmodulin kinase, through an increase in intracellular calcium concentration.

IGFBPs are proteins that bind to insulin-like growth factors (hereinafter, abbreviated as IGFs) to modulate the actions of the factors. It has been made clear that there are two molecular species in IGFs, which are called IGF-I and IGF-II, respectively. IGF-I and IGF-II, each of which is structurally highly similar to insulin, bind to the corresponding cell surface receptors, a type I IGF receptor and a type II IGF receptor, and play an important role in the proliferation and differentiation of various cells.

It has been made clear that there are six molecular species in IGFBPs, which are called IGFBP-1 to IGFBP-6, and those species are widely expressed in various tissues. Any of IGFBP-1 to IGFBP-6 binds to IGFs to modulate interactions between the IGFs and their receptors, to thereby control the actions of the IGFs.

Meanwhile, there are reports that several actions of IGFBPs are independent of IGFs. However, there are little findings on detailed mechanisms of such IGF-independent actions of IGFBPs (Non-Patent References 9 and 10).

REFERENCE LIST

Non-Patent References

[Non-Patent Reference 1] Srivastava, D., Genetic assembly of the heart: implications for congenital heart disease., Annu Rev Physiol 63, 451-69 (2001).

[Non-Patent Reference 2] Olson, E. N. & Schneider, M. D., Sizing up the heart: development redux in disease., Genes Dev 17, 1937-56 (2003).

[Non-Patent Reference 3] Leri, A., Kajstura, J. & Anversa, P. Cardiac stem cells and mechanisms of myocardial regeneration., Physiol Rev 85, 1373-416 (2005).

[Non-Patent Reference 4] Foley, A. & Mercola, M., Heart induction: embryology to cardiomyocyte regeneration., Trends Cardiovasc Med 14, 121-5 (2004).

[Non-Patent Reference 5] Willert K., Brown J. D., Danenberg E., Duncan A. W., Weissman I. L., Reya T., Yates J R 3rd, Nusse R., Nature 423, 448-52 (2003).

[Non-Patent Reference 6] Reya T., Duncan A. W., Ailles L., Domen J., Scherer D. C., Willert K., Hintz L., Nusse R., Weissman I. L., Nature 423, 409-14 (2003).

[Non-Patent Reference 7] Moon, R. T., Kohn, A. D., DeFerrari, G. V. & Kaykas, A., WNT and beta-catenin signalling: diseases and therapies., Nat Rev Genet 5, 691-701 (2004).

[Non-Patent Reference 8] Kikuchi, A., Yamamoto, H. & Kishida, S., Multiplicity of the interactions of Wnt proteins and their receptors., Cell Signal 19, 659-71 (2007).

[Non-Patent Reference 9] Firth, S. M. & Baxter, R. C., Cellular actions of the insulin-like growth factor binding proteins., Endocr Rev 23, 824-54 (2002).

[Non-Patent Reference 10] Mohan, S. & Baylink, D. J., IGF-binding proteins are multifunctional and act via IGF-dependent and -independent mechanisms., J Endocrinol 175, 19-31 (2002).

SUMMARY OF INVENTION

Problem to be Solved by the Invention

An object of the present invention is to provide a novel soluble factor that modulates morphogenesis and cell proliferation, such as cardiac development and/or cardiomyocyte differentiation.

Means for Solving the Object

The inventors of the present invention have made extensive studies using P19CL6 cells, a cell line that differentiates into cardiomyocytes, in order to achieve the above-mentioned object. As a result, the inventors have found that: (1) IGFBP-4 induces the cardiomyocyte differentiation of P19CL6 cells in vitro; (2) the knockdown of IGFBP-4 attenuates cardiomyogenesis both in vitro and in vivo; (3) those actions of IGFBP-4 are independent of an IGF-binding activity of IGFBP-4; and (4) IGFBP-4 physically interacts with Wnt receptors, Frizzled 8 (hereinafter, abbreviated as Frz8) and LRP5/6, to thereby inhibit the binding of Wnt3A to Frz8 and LRP6. Based on those results, the inventors have revealed that IGFBP-4 inhibits Wnt signalling, and the inhibition of Wnt signalling induces cardiomyocyte differentiation. The inventors have also found that not only IGFBP-4 but also IGFBP-1, IGFBP-2, and IGFBP-6 bind to Frz8 and LRP6 to inhibit Wnt signalling. The present invention has been achieved based on those findings.

That is, the present invention relates to an inhibitor of Wnt signalling, comprising at least one kind of insulin-like growth-factor-binding protein (IGFBP), the protein being capable of binding to a Wnt receptor.

The present invention also relates to an inhibitor of Wnt signalling, comprising as an active ingredient an effective amount of at least one kind of insulin-like growth-factor-binding protein (IGFBP), the protein being capable of binding to a Wnt receptor, wherein the at least one kind of the protein is at least one kind of protein selected from the following group of proteins:
(1) a protein that is represented by an amino acid sequence set forth in any one of SEQ ID NOS: 2, 4, 6, and 8 of Sequence Listing;
(2) a protein that has 70% or more homology to the protein according to the item (1) and is capable of binding to a Wnt receptor; and
(3) a protein that is represented by an amino acid sequence having 1 to 10 amino acid mutations in the amino acid sequence of the protein according to the item (1) and is capable of binding to a Wnt receptor.

The present invention also relates to the above-mentioned inhibitor of Writ signalling, wherein the at least one kind of insulin-like growth-factor-binding protein (IGFBP), the protein being capable of binding to a Wnt receptor, is a protein represented by an amino acid sequence set forth in any one of SEQ ID NOS: 2, 4, 6, and 8 of Sequence Listing.

The present invention also relates to the above-mentioned inhibitor of Writ signalling, wherein the at least one kind of insulin-like growth-factor-binding protein (IGFBP), the protein being capable of binding to a Wnt receptor, is a protein represented by an amino acid sequence set forth in SEQ ID NO: 2 of Sequence Listing.

The present invention also relates to any one of the above-mentioned inhibitors of Wnt signalling, wherein the Wnt receptor is low-density lipoprotein receptor-related protein 6 (LRP6) and Frizzled 8 (Frz8).

The present invention also relates to an inhibitor of Wnt signalling, comprising at least one kind of polynucleotide encoding an insulin-like growth-factor-binding protein (IGFBP), the protein being capable of binding to a Wnt receptor.

The present invention also relates to an inhibitor of Wnt signalling, comprising as an active ingredient an effective amount of at least one kind of polynucleotide encoding an insulin-like growth-factor-binding protein (IGFBP), the protein being capable of binding to a Wnt receptor, wherein the at least one kind of the polynucleotide is at least one kind of polynucleotide selected from the following group of polynucleotides:
(1) a polynucleotide that is represented by a base sequence set forth in any one of SEQ ID NOS: 1, 3, 5, and 7 of Sequence Listing;
(2) a polynucleotide that has 70% or more homology to the polynucleotide according to the item (1) and encodes a protein capable of binding to a Wnt receptor;
(3) a polynucleotide that is represented by a base sequence having 1 to 30 nucleotide mutations in the base sequence of the polynucleotide according to the item (1) and encodes a protein capable of binding to a Wnt receptor; and
(4) a polynucleotide that includes the polynucleotide according to any one of the items (1) to (3).

The present invention also relates to the above-mentioned inhibitor of Wnt signalling, wherein the at least one kind of polynucleotide encoding an insulin-like growth-factor-binding protein (IGFBP), the protein being capable of binding to a Wnt receptor, is a polynucleotide represented by a base sequence set forth in any one of SEQ ID NOS: 1, 3, 5, and 7 of Sequence Listing.

The present invention also relates to the above-mentioned inhibitor of Wnt signalling, wherein the at least one kind of polynucleotide encoding an insulin-like growth-factor-binding protein (IGFBP), the protein being capable of binding to a Wnt receptor, is a polynucleotide represented by a base sequence set forth in SEQ ID NO: 1 of Sequence Listing.

The present invention also relates to the above-mentioned inhibitor of Wnt signalling, wherein the Wnt receptor is low-density lipoprotein receptor-related protein 6 (LRP6) and Frizzled 8 (Frz8).

The present invention also relates to a method for inhibiting Wnt signalling, comprising using at least one kind of insulin-like growth-factor-binding protein (IGFBP), the protein being capable of binding to a Wnt receptor.

The present invention also relates to the above-mentioned method for inhibiting Wnt signalling, wherein the at least one kind of insulin-like growth-factor-binding protein (IGFBP), the protein being capable of binding to a Wnt receptor, is at least one kind of protein selected from the following group of proteins:
(1) a protein that is represented by an amino acid sequence set forth in any one of SEQ ID NOS: 2, 4, 6, and 8 of Sequence Listing;

(2) a protein that has 70% or more homology to the protein according to the item (1) and is capable of binding to a Wnt receptor; and (3) a protein that is represented by an amino acid sequence having 1 to 10 amino acid mutations in the amino acid sequence of the protein according to the item (1) and is capable of binding to a Wnt receptor.

The present invention also relates to the above-mentioned method for inhibiting Wnt signalling, wherein the at least one kind of insulin-like growth-factor-binding protein (IGFBP), the protein being capable of binding to a Wnt receptor, is a protein represented by an amino acid sequence set forth in any one of SEQ ID NOS: 2, 4, 6, and 8 of Sequence Listing.

The present invention also relates to the above-mentioned method for inhibiting Wnt signalling, wherein the at least one kind of insulin-like growth-factor-binding protein (IGFBP), the protein being capable of binding to a Wnt receptor, is a protein represented by an amino acid sequence set forth in SEQ ID NO: 2 of Sequence Listing.

The present invention also relates to any one of the above-mentioned method for inhibiting Wnt signalling, wherein the Wnt receptor is low-density lipoprotein receptor-related protein 6 (LRP6) and Frizzled 8 (Frz8).

The present invention also relates to a method for inhibiting Wnt signalling, comprising using at least one kind of polynucleotide encoding an insulin-like growth-factor-binding protein (IGFBP), the protein being capable of binding to a Wnt receptor.

The present invention also relates to the above-mentioned method for inhibiting Wnt signalling, wherein the at least one kind of polynucleotide encoding an insulin-like growth-factor-binding protein (IGFBP), the protein being capable of binding to a Wnt receptor, is at least one kind of polynucleotide selected from the following group of polynucleotides:

(1) a polynucleotide that is represented by a base sequence set forth in any one of SEQ ID NOS: 1, 3, 5, and 7 of Sequence Listing;

(2) a polynucleotide that has 70% or more homology to the polynucleotide according to the item (1) and encodes a protein capable of binding to a Wnt receptor;

(3) a polynucleotide that is represented by a base sequence having 1 to 30 nucleotide mutations in the base sequence of the polynucleotide according to the item (1) and encodes a protein capable of binding to a Wnt receptor; and (4) a polynucleotide that includes the polynucleotide according to any one of the items (1) to (3).

The present invention also relates to the above-mentioned method for inhibiting Wnt signalling, wherein the at least one kind of polynucleotide encoding an insulin-like growth-factor-binding protein (IGFBP), the protein being capable of binding to a Wnt receptor, is a polynucleotide represented by a base sequence according to any one of SEQ ID NOS: 1, 3, 5, and 7 of Sequence Listing.

The present invention also relates to the above-mentioned method for inhibiting Wnt signalling, wherein the at least one kind of polynucleotide encoding an insulin-like growth-factor-binding protein (IGFBP), the protein being capable of binding to a Wnt receptor, is a polynucleotide represented by a base sequence set forth in SEQ ID NO: 1 of Sequence Listing.

The present invention also relates to any on of the above-mentioned method for inhibiting Wnt signalling, wherein the Wnt receptor is low-density lipoprotein receptor-related protein 6 (LRP6) and Frizzled 8 (Frz8).

The present invention also relates to a use of an insulin-like growth-factor-binding protein (IGFBP), the protein being capable of binding to a Wnt receptor, and/or a polynucleotide encoding the protein, in the manufacture of an inhibitor of Wnt signalling.

The present invention also relates to a medicament for the prevention and/or treatment of a disease due to enhanced Wnt signalling, comprising as an active ingredient an effective amount of any one of the above-mentioned inhibitor of Wnt signalling.

The present invention also relates to a method for the prevention and/or treatment of a disease due to enhanced Wnt signalling, comprising administering to a subject an effective amount of any one of the above-mentioned inhibitor of Wnt signalling.

The present invention also relates to a use of any one of the above-mentioned inhibitor of Wnt signalling in the prevention and/or treatment of a disease due to enhanced Wnt signalling.

The present invention also relates to a medicament for the induction of cardiomyocyte differentiation, comprising as an active ingredient an effective amount of any one of the above-mentioned inhibitor of Wnt signalling.

The present invention also relates to a method of inducing cardiomyocyte differentiation, comprising bringing an effective amount of any one of the above-mentioned inhibitor of Wnt signalling into contact with a cell capable of differentiating into a cardiomyocyte.

The present invention also relates to the above-mentioned method of inducing cardiomyocyte differentiation, wherein the cell capable of differentiating into a cardiomyocyte is a pluripotent stem cell.

The present invention also relates to the above-mentioned method of inducing cardiomyocyte differentiation, wherein the cell capable of differentiating into a cardiomyocyte is an embryonic stem cell.

The present invention also relates to a cardiomyocyte, which is obtained by any one of the above-mentioned method of inducing cardiomyocyte differentiation.

The present invention also relates to a use of a cardiomyocyte, which is obtained by any one of the above-mentioned method of inducing cardiomyocyte differentiation.

The present invention also relates to a method of inducing cardiomyocyte differentiation, comprising administering to a subject an effective amount of any one of the above-mentioned inhibitor of Wnt signalling.

Advantageous Effects of Invention

According to the present invention, there can be provided the inhibitor of Wnt signalling, comprising as an active ingredient an insulin-like growth-factor-binding protein (IGEBP), the protein binding to a Wnt receptor, and/or a polynucleotide encoding the protein.

Wnt signals are involved in the control of morphogenesis and are important for various phenomena such as development, differentiation control, growth regulation, and survival of stem cells, and cell malignant transformation. The inhibitor of Wnt signalling according to the present invention is therefore useful as a medicament that modulates morphogenesis and cell proliferation, such as cardiac development and/or cardiomyocyte differentiation, in the fields of pharmaceutical development, scientific research, and the like.

According to the present invention, there can also be provided the medicament for the prevention and/or treatment of a disease due to enhanced Wnt signalling and the medicament for the induction of cardiomyocyte differentiation, the medicaments each comprising as an active ingredient the protein and/or a polynucleotide encoding the protein. The present invention can also provide the use of an insulin-like growth-factor-binding protein (IGFBP), the protein binding to a Wnt receptor, and/or a polynucleotide encoding the protein, in the manufacture of an inhibitor of Wnt signalling, a medicament for the prevention and/or treatment of a disease due to enhanced Wnt signalling, and a medicament for the induction of cardiomyocyte differentiation. The present invention can also provide the use of an insulin-like growth-factor-binding protein (IGFBP), the protein binding to a Wnt receptor, and/or a polynucleotide encoding the protein, in the inhibition of Wnt signalling, the prevention and/or treatment of a disease due to enhanced Wnt signalling, and the induction of cardiomyocyte differentiation. According to the present invention, there can also be provided the method of inhibiting Wnt signalling, comprising using an insulin-like growth-factor-binding protein (IGFBP), the protein binding to a Wnt receptor, and/or a polynucleotide encoding the protein, the method for the prevention and/or treatment of a disease due to enhanced Wnt signalling, the method of inducing cardiomyocyte differentiation, and the cardiomyocyte which is obtained by the method of inducing cardiomyocyte differentiation and the use thereof.

BRIEF DESCRIPTION OF DRAWINGS

FIG. 1-*a* shows that the cardiomyocyte differentiation of P19CL6 cells was induced with culture media conditioned by OP9 cells but was not induced with culture media conditioned by COS7 cells. The cardiomyocyte differentiation was assessed by cytomorphology (two left panels), the induction of an MF20-positive area (middle panel), and the induction of the expression of cardiac marker genes (α myosin heavy chain (αMHC), Nkx2.5, and GATA-4) and a cardiac troponin (cTnT) protein (right panel). Scale bar=100 μm.

FIG. 1-*b* shows that treatment with IGFBP-4 (1 μg/ml) induced the cardiomyocyte differentiation of P19CL6 cells in the absence of dimethylsulfoxide (hereinafter, abbreviated as DMSO). The cardiomyocyte differentiation was assessed by the induction of an MF20-positive area (left panel) and the induction of the expression of cardiac marker genes (αMHC, Nkx2.5, and GATA-4) and a cTnT protein (right panel). In the figure, IGFBP-4 is represented by BP4 and a control is represented by C.

FIG. 1-*c* shows that treatment with a neutralizing antibody against IGFBP-4 (40 μg/ml) attenuated the cardiomyocyte differentiation of P19CL6 cells induced by OP9-conditioned media. The cardiomyocyte differentiation was assessed by the induction of an MF20-positive area (left panel) and the induction of the expression of cardiac marker genes (αMHC, Nkx2.5, and GATA-4) and a cTnT protein (right panel). In the figure, the neutralizing antibody against IGFBP-4 is represented by αBP4.

FIG. 1-*d* shows that treatment with a combination of 5 μg/ml each of a neutralizing antibody against IGF-I and a neutralizing antibody against IGF-II did not exhibit any effect on the cardiomyocyte differentiation of P19CL6 cells induced by IGFBP-4. The cardiomyocyte differentiation was assessed by the induction of an MF20-positive area (upper panel) and the induction of the expression of a cTnT protein (middle panel). In the figure, the combination of the neutralizing antibodies (the above-mentioned combination) is represented by αIGFs and a control is represented by C.

FIG. 1-*e* shows that IGFBP-4 mutant (IGFBP-4-H74P) incapable of binding to IGFs retains a cardiomyogenic activity. The cardiomyogenic activity was assessed by the cardiomyocyte differentiation of P19CL6 cells. The cardiomyocyte differentiation was assessed by the induction of an MF20-positive area (upper panel) and the induction of the expression of a cTnT protein (middle panel). In the figure, IGFBP-4-H74P is represented by BP4 (H74P) and a control is represented by C.

FIG. 1-*f* shows that a combination of 100 ng/ml each of IGF-I and -II attenuates the cardiomyocyte differentiation of P19CL6 cells induced by wild-type IGFBP-4 (left panels) but does not attenuate the cardiomyocyte differentiation of P19CL6 cells induced by mutant IGFBP-4-H74P (right panels). The cardiomyocyte differentiation was assessed by the induction of an MF20-positive area (upper panels) and the induction of the expression of a cTnT protein (middle panels). In the figure, the combination of IGF-I and -II is represented by IGFs, IGFBP-4 is represented by BP4, IGFBP-4-H74P is represented by BP4(H74P), and a control is represented by C.

FIG. 2-*a* shows that IGFBP-4 attenuated Wnt/β-catenin signalling in P19CL6 cells. When P19CL6 cells were transfected with a TOPFLASH reporter gene and an LRP6 or Frz8 expression vector, and treated with Wnt3A and IGFBP-4, the TOPFLASH activity was lowered as compared to the case of being treated with Wnt3A alone. The TOPFLASH activity was assessed by measuring a luciferase activity. In the figure, IGFBP-4 is represented by BP4.

FIG. 2-*b* shows that *Xenopus* IGFBP-4 (hereinafter, sometimes abbreviated as XIGFBP-4) inhibited secondary axis formation induced by *Xenopus* Wnt8 (hereinafter, abbreviated as Xwnt8) in *Xenopus* embryos (N=20 for each group). In the figure, XIGFBP-4 is represented by XBP4.

FIG. 2-*c* shows that XIGFBP-4 inhibited secondary axis formation induced by LRP6 in *Xenopus* embryos (N=30 for each group). In the figure, XIGFBP-4 is represented by XBP4.

FIG. 2-*d* shows that IGFBP-4 directly interacted with LRP6N. The interaction was assessed by allowing LRP6N-Myc to react with IGFBP-4-V5 and then performing immunoprecipitation (IP) with an anti-Myc antibody and subsequent immunoblotting (IB) with an anti-V5 antibody or an anti-Myc antibody (left panels), and immunoprecipitation (IP) with an anti-V5 antibody and subsequent immunoblotting (IB) with an anti-Myc antibody or an anti-V5 antibody (right panels).

FIG. 2-*e* shows that IGFBP-4 directly interacted with a cysteine-rich domain of Frz8 (hereinafter, abbreviated as Frz8CRD). The interaction was assessed by allowing Frz8CRD-Myc to react with IGFBP-4-V5 and then performing immunoprecipitation (IP) with an anti-Myc antibody and subsequent immunoblotting (IB) with an anti-V5 antibody or an anti-Myc antibody (left panels), and immunoprecipitation (IP) with an anti-V5 antibody and subsequent immunoblotting (IB) with an anti-Myc antibody or an anti-V5 antibody (right panels).

FIG. 2-*f* shows the results of binding assays of $^{125}$I-labelled IGFBP-4 and LRP6N. The inset is a scatchard plot showing the presence of two binding sites with different binding affinities (Kd).

FIG. 2-*g* shows the results of binding assays of $^{125}$I-labelled IGFBP-4 and Frz8CRD. The inset is a scatchard plot showing the presence of a single binding site with a binding affinity (Kd) of 25 nM.

FIG. 2-*h* shows that IGFBP-4 inhibited the binding of $^{125}$I-labelled Wnt3A to LRP6N in a dose-dependent fashion.

FIG. 2-*i* shows that IGFBP-4 inhibited the binding of $^{125}$I-labelled Wnt3A to Frz8CRD in a dose-dependent fashion.

FIG. 3-*a* shows changes in expression of IGFBP family members during the DMSO-induced cardiomyocyte differentiation of P19CL6 cells. The expression of IGFBPs was measured by a reverse transcription polymerase chain reaction (RT-PCR) on day 0 (D0), day 2 (D2), day 4 (D4), day 6 (D6), and day 8 (D8) after the addition of DMSO.

FIG. 3-b shows that the knockdown of IGFBP-4 in P19CL6 cells attenuated the expression of cardiac markers (αMHC, Nkx20.5, and GATA-4) (left panel) and the expression of cTnT (right panel) in the responses of the cells to DMSO treatment. The knockdown of IGFBP-4 was conducted using two kinds of IGFBP-4 siRNAs (represented by BP4-1 and BP4-2 in the figure). On the other hand, the knockdown of IGFBP-3 and IGFBP-5 mediated by IGFBP-3 siRNA (represented by BP3 in the figure) and IGFBP-5 siRNA (represented by BP5 in the figure) did not have any influence on the expression of cTnT in the responses to DMSO treatment (right panel).

FIG. 3-c shows that treatment with a neutralizing antibody against IGFBP-4 (40 µg/ml) attenuated the DMSO-induced cardiomyocyte differentiation of P19CL6 cells. The cardiomyocyte differentiation was assessed by the induction of an MF20-positive area (left panel) and the induction of the expression of cardiac marker genes (αMHC, Nkx2.5, and GATA-4) and a cTnT protein (right panel). In the figure, the neutralizing antibody against IGFBP-4 is represented by αBP4.

FIG. 3-d shows the results of immunostaining of IGFBP-4 after the DMSO-induced differentiation of P19CL6 cells stably transfected with an αMHC-green fluorescent protein (αMHC-GFP) reporter gene. The upper left panel shows IGFBP-4 staining, the upper right panel shows GFP expression representing differentiated cardiomyocytes, the lower left panel shows nuclear staining with 4',6-diamidino-2-phenylindole (DAPI), and the lower right panel shows a merged picture. Scale bar=100 µm.

FIG. 3-e shows that the cardiomyocyte differentiation of P19CL6 cells attenuated by the knockdown of IGFBP-4 was rescued by inhibiting Wnt/β-catenin signalling. Control P19CL6 cells and IGFBP-4-knocked-down P19CL6 cells were treated with an expression vector for GFP or an extracellular portion of LRP6 (LRP6N), and induced to differentiate into cardiomyocytes by DMSO treatment. LRP6N is a dominant-negative form of wild-type LRP6, and the overexpression thereof rescued cardiomyocyte differentiation attenuated by the knockdown of IGFBP-4. The cardiomyocyte differentiation was assessed by an MF20-positive area (left panel) and the expression of cardiac marker genes (αMHC, Nkx2.5, and GATA-4) and a cTnT protein (right panel).

FIG. 4-a shows the results of the in situ hybridization analyses of the expression of mRNAs of Nkx2.5 as an early cardiac marker, cardiac troponin I (cTnI) as a mature cardiac marker, Hex as a liver marker, and XIGFBP-4 at stages 34, 38 and 42 in Xenopus embryos. In the figure, XIGFBP-4 mRNA is represented by XBP4.

FIG. 4-b shows that the knockdown of XIGFBP-4 with two independent morpholinos (MO1 or MO2) resulted in severe cardiac defects (left panel) and that the cardiac defects were rescued by co-injection of MO-resistant wild-type XIGFBP-4, mutant XIGFBP-4-H74P, or an extracellular portion of LRP6 (LRP6N) (middle and right panels). The heart was assessed by in situ hybridization of cTnI at stage 42 (N=30 for each group). In the figure, wild-type XIGFBP-4 is represented by BP4, and XIGFBP-4-H74P is represented by BP4 (H74P). Further, no inj. means that no knockdown with a morpholino was conducted. In the middle and right panels, an open column, a hatched column, a cross-hatched column, a stippled column, and a solid column represent normal heart, abnormal heart, small heart, heartless, and death, respectively.

FIG. 4-c shows temporal profiles of cardiac defects induced by the knockdown of XIGFBP-4 with a morpholino (MO1 or MO2). The morphology of the heart as assessed by the in situ hybridization of cTnI was almost normal at stage 34 but was severely perturbed at stages 38 and 42. In the figure, no inj. means that no knockdown with a morpholino was conducted. The right columns represent sections of control embryos and MO-injected embryos. The arrow indicates the heart in the control embryos. No heart-like structure was observed in the MO-injected embryos.

FIG. 5-a shows that IGFBP-4 did not alter any activity of FOPFLASH that is a negative control of TOPFLASH.

FIG. 5-b shows that IGFBP-4 did not alter the activation of a BRE-luc reporter gene with BMP. BMP-responsive BRE-luc was activated by BMP2 in a concentration-dependent manner (left panel) and the activation was not altered by IGFBP-4 (right panel). In the figure, IGFBP-4 is represented by BP4. Reporter gene assays were performed in 293 cells.

FIG. 5-c shows the results of the studies by animal cap assays for the IGFBP-4-induced inhibition of a canonical Wntpathway. The assays were performed by injecting each of LRP6, β-catenin, β-galactosidase, and XIGFBP-4 RNA into the animal pole of two-cell embryos, dissecting an animal cap at stage 85, and measuring the expression of Wnt target genes (Siamois and Xnr-3). XIGFBP-4 attenuated the expression of Siamois and Xnr-3 induced by LRP6, but did not have any influence on the expression induced by β-catenin. ODC represents ornithine decarboxylase and was measured as a control.

FIG. 5-d shows that IGFBP-4 inhibited canonical Wnt signalling activated by Wnt3A and LRP6 (left and right panels, respectively). The activation of canonical Wnt signalling was measured by TOPFLASH reporter gene assays and assessed based on a TOPFLASH activity. In the figure, IGFBP-4 is represented by BP4. The TOPFLASH reporter gene assays were performed in 293 cells.

FIG. 5-e shows that IGFBP-4 did not inhibit canonical Wnt signalling induced by β-catenin, Disheveled-1 (left panel), or lithium chloride (right panel) that is a glycogen synthase kinase 3 (GSK3) inhibitor. In the figure, IGFBP-4 is represented by BP4, and Disheveled-1 is represented by Div-1. TOPFLASH reporter gene assays were performed in 293 cells.

FIG. 6-a shows the results of binding assays between $^{125}$I-labelled Wnt3A and Frz8CRD in the presence or absence of various concentrations of IGFBP-4. In the figure, a rectangle symbol represents no IGFBP-4, a circle symbol represents 50 nM IGFBP-4, and a triangle symbol represents 100 nM IGFBP-4. The inset is a Lineweaver-Burk plot showing that IGFBP-4 is a competitive inhibitor of the binding of Wnt3A to Frz8CRD.

FIG. 6-b schematically illustrates LRP6 deletion mutants used in Example 1. All the deletion mutants are soluble forms. In the figure, SP represents a signal peptide, β-pro represents a β-propeller domain, and EGF represents an EGF-like domain, LDLR represents LDL receptor type A repeats, and TM means a transmembrane domain.

FIG. 6-c shows that IGFBP-4 interacted with E1-4 mutants of LRP6N and LRP6. The interaction was assessed by allowing an LRP6N-Myc or LRP6 mutant to react with IGFBP-4-V5, and performing immunoprecipitation (IP) with an anti-Myc antibody and subsequent immunoblotting (IB) with an anti-V5 antibody or an anti-Myc antibody (left panel), and immunoprecipitation (IP) with an anti-V5 antibody and subsequent immunoblotting (IB) with an anti-Myc antibody or an anti-V5 antibody (right panel). In the figure, IGFBP-4 is represented by BP4.

FIG. 6-*d* shows that IGFBP-4 interacted with an L mutant, an E1-2/L mutant, and an E3-4/L mutant of LRP6. The interaction was assessed by allowing each Myc-tagged LRP6 mutant to react with IGFBP-4-V5, and performing immunoprecipitation (IP) with an anti-Myc antibody and subsequent immunoblotting (IB) with an anti-V5 antibody or an anti-Myc antibody (left panel), and immunoprecipitation (IP) with an anti-V5 antibody and subsequent immunoblotting (IB) with an anti-Myc antibody or an anti-V5 antibody (right panel). In the figure, IGFBP-4 is represented by BP4.

FIG. 6-*e* shows that IGFBP-4 interacted with E1-2 mutant and E3-4 mutant of LRP6. Meanwhile, Dkk1 used as a control predominantly interacted with an LRP6 E3-4 mutant. The interaction between IGFBP-4 and the LRP6 mutant was assessed by allowing each Myc-tagged LRP6 mutant to react with IGFBP-4-V5, and performing immunoprecipitation (IP) with an anti-Myc antibody and subsequent immunoblotting (IB) with an anti-Myc antibody (three lanes at the left side in the left panel), and immunoprecipitation (IP) with an anti-V5 antibody and subsequent immunoblotting (IB) with an anti-Myc antibody (three lanes at the right side in the left panel). Further, the interaction between the Dkk1 and the LRP6 mutant was assessed by allowing each Myc-tagged LRP6 mutant to react with FLAG-tagged Dkk1, and performing immunoprecipitation (IP) with an anti-FLAG antibody and subsequent immunoblotting (IB) with an anti-Myc antibody (three lanes at the left side in the left panel), and performing immunoprecipitation (IP) with an anti-Myc antibody and subsequent immunoblotting (IB) with an anti-Myc antibody (three lanes at the right side in the left panel). In the figure, IGFBP-4 is represented by BP4. Further, NS means non-specific binding.

FIG. 6-*f* shows that amino-terminal deletion mutants of IGFBP-4 interacted with LRP6 and Frz8, whereas carboxy-terminal thyroglobulin domain deletion mutants did not interact with LRP6 and Frz8. The interaction between each IGFBP-4 and Frz8 or LRP6 was assessed by allowing V5-tagged full-length IGFBP-4, amino-terminal deletion IGFBP-4, and carboxy-terminal deletion IGFBP-4 to react with Myc-tagged LRP6 or Frz8, and performing immunoprecipitation (IP) with an anti-Myc antibody and subsequent immunoblotting (IB) with an anti-V5 antibody or immunoblotting (IB) with an anti-Myc antibody (middle panel). The left panel schematically illustrates full-length IGFBP-4 and IGFBP-4 deletion mutants. In the figure, full-length IGFBP-4 is represented by FL or BP4FL, amino-terminal deletion IGFBP-4 is represented by ΔN or BP4ΔN, and carboxy-terminal deletion IGFBP-4 is represented by ΔC or BP4ΔC. Further, IGF means an IGF-binding domain and TG means a thyroglobulin domain.

FIG. 7-*a* shows the results of the studies for effects of IGFBP-4 on the induction of cardiomyocyte differentiation of ES cells. The ES cells were stably transfected with an αMHC-GFP reporter gene, and the cardiomyocyte differentiation was induced by a hanging drop method. IGFBP-4 (1 μg/ml) inhibited the cardiomyocyte differentiation of the ES cells when being applied on day 0 today 3 (D0-3) but enhanced cardiogenesis when being applied on day 3 to day 5 (D3-5). The extent of the cardiomyocyte differentiation of the ES cells was assessed by the microscopic observation of a GFP-positive area. Scale bar=200 μm.

FIG. 7-*b* shows the results of the studies for effects of IGFBP-4 on the induction of the cardiomyocyte differentiation of ES cells. The ES cells were stably transfected with an αMHC-GFP reporter gene, and the cardiomyocyte differentiation was induced by a hanging drop method. IGFBP-4 (1 μg/ml) inhibited the cardiomyocyte differentiation of the ES cells when being applied on day 0 today 3 (D0-3) but enhanced cardiogenesis when being applied on day 3 to day 5 (D3-5). The extent of the cardiomyocyte differentiation of the ES cells was assessed by a ratio of a GFP-positive area.

FIG. 7-*c* shows the results of the studies for effects of IGFBP-4 on the induction of the cardiomyocyte differentiation of ES cells. The ES cells were stably transfected with an αMHC-GFP reporter gene, and the cardiomyocyte differentiation was induced by a hanging drop method. IGFBP-4 (1 μg/ml) inhibited the cardiomyocyte differentiation of the ES cells when being applied on day 0 to day 3 (D0-3) but enhanced cardiogenesis when being applied on day 3 to day 5 (D3-5). The extent of the cardiomyocyte differentiation of the ES cells was assessed by the expression of cardiac marker genes (αMHC, Nkx2.5, and GATA-4) and a cTnT protein (right panel).

FIG. 7-*d* shows the expression of IGFBP family members in the cardiomyocyte differentiation of ES cells. The expression of IGFBPs was measured by RT-PCR on day 0 (D0), day 3 (D3), day 4 (D4), and day 5 (D5) after the induction of the differentiation.

FIG. 7-*e* shows that the knockdown of IGFBP-4 in ES cells attenuated the cardiomyocyte differentiation of the cells. The ES cells were stably transfected with an αMHC-GFP reporter gene. Further, IGFBP-4 was knocked down using two kinds of IGFBP-4 siRNAs (represented by BP4-1 and BP4-2 in the figure), and the cardiomyocyte differentiation was induced by a hanging drop method. The cardiomyocyte differentiation was assessed by the expression of cardiac marker genes (αMHC, Nkx2.5, and GATA-4) (left panel), and by a GFP-positive area and the expression of cTnT (right panel). On the other hand, the knockdown of IGFBP-3 and IGFBP-5 mediated by IGFBP-3 siRNA (represented by BP3 in the figure) and IGFBP-5 siRNA (represented by BP5 in the figure) did not exhibit any effect on the ratio of the GFP-positive area and the expression of cTnT (right panel).

FIG. 7-*f* shows that treatment with a neutralizing antibody against IGFBP-4 (40 μg/ml) attenuated the cardiomyocyte differentiation of ES cells. The ES cells were stably transfected with an αMHC-GFP reporter gene, and the cardiomyocyte differentiation was induced by a hanging drop method. The cardiomyocyte differentiation was assessed by a ratio of a GFP-positive area (left panel) and the expression of cardiac marker genes (αMHC, Nkx2.5, and GATA-4) and cTnT (right panel). In the figure, the neutralizing antibody against IGFBP-4 is represented by αBP4.

FIG. 7-*g* shows the results of immunostaining of IGFBP-4 after inducing the cardiomyocyte differentiation of ES cells stably transfected with an αMHC-GFP reporter gene. The upper left panel shows IGFBP-4 staining, the upper right panel shows GFP expression representing differentiated cardiomyocytes, the lower left panel shows nuclear staining with DAPI, and the lower right panel shows a merged picture. Scale bar=100 μm.

FIG. 7-*h* shows that the in situ hybridization analysis of IGFBP-4 in mouse embryos (E95) detected strong signals in pharyngeal arches, liver bud, and limb bud. S and AS show the results of in situ hybridization analysis using a sense probe and an antisense probe, respectively.

FIG. 8-*a* illustrates partial sequences of two alleles of XIGFBP-4, target sequences of MO1 and MO2 for XIGFBP-4 and their positions, a partial sequence of MO-sensitive (MO-s) XIGFBP-4 cDNA, and a partial sequence of MO-resistant (MO-r) XIGFBP-4 cDNA. An initiation codon ATG, and a mismatch introduced for the generation of MO-resistant XIGFBP-4 cDNA were underlined.

FIG. 8-b shows the validation results of the activity and specificity of MO1 and MO2 for XIGFBP-4. MO-sensitive (MO-s) and MO-resistant (MO-r) XIGFBP-4-Myc mRNAs were injected into Xenopus embryos. The expression of an XIGFBP-4-Myc protein translated from MO-sensitive mRNA was attenuated by the co-injection of MO1 or MO2, whereas the expression of a protein from MO-resistant mRNA was not affected by the co-injection. RT-PCR analysis revealed that mRNAs were injected in an equivalent amount. ODC represents ornithine decarboxylase and was measured as a control for RT-PCR.

FIG. 8-c illustrates the specificity of cardiac phenotypes induced by MO1 and MO2 for XIGFBP-4. XIGFBP-4 MO1 or MO2 resulted in cardiac defects. Meanwhile, cardiac defects induced by XIGFBP-4 MO1 or MO2 were rescued by co-injection of MO-resistant XIGFBP-4 cDNA (N=30 for each group). In the figure, an open column, a hatched column, a cross-hatched column, a stippled column, and a solid column represent normal heart, abnormal heart, small heart, heartless, and death, respectively.

FIG. 8-d shows that normal cardiac development was impaired by the activation of a Wnt pathway. Plasmid DNA (pCSKA-Xwnt8) encoding Xwnt8 under control of a cytoskeletal actin promoter was injected into the dorsal regions of two dorsal-vegetal blastomeres fated to be heart and liver anlage at 8-cell stage of Xenopus embryos to activate Wnt in the heart-forming region. pCSKA-Xwnt8-injected embryos (lower panel) were reduced in cardiac size as compared to control embryos (upper panel) at stage 42.

FIG. 8-e shows that the activation of a Wnt pathway caused abnormalities of cardiogenesis at the late stage of embryogenesis. Xwnt8 mRNA was introduced into the vicinity of Xenopus heart anlage at stage 28 by electroporation. At this time, GFP mRNA was co-injected to assess the efficiency of the electroporation. The expression of GFP was observed in the heart-forming region at stage 34 (upper panel, the head is at the left side and the dorsal side is at the upper side). The abnormal cardiac morphogenesis was observed at stage 42 in embryos injected with Xwnt8 and GFP mRNA (lower panel) as compared to the control embryos (middle panel) injected with GFP mRNA alone.

FIG. 8-f shows the results of quantitative analysis for an effect of Wnt activation on cardiac development. In Xenopus embryos injected with plasmid DNA (pCSKA-Xwnt8) encoding Xwnt8 under control of a cytoskeletal actin promoter, the heart mostly has a small size as compared to the heart of a normal size in control embryos. Further, also in Xenopus embryos introduced with Xwnt8 by electroporation, the ratio of small sized heart was high.

FIG. 9-a shows that an intranuclear β-catenin amount increased by treatment of L cells with Wnt3A was lowered by treatment with IGFBP-4. In the figure, IGFBP-4 is represented by BP4. TOPO-I, which was an expression control for an intranuclear protein, was not affected by treatment with Wnt3A and IGFBP-4.

FIG. 9-b shows that an intranuclear β-catenin amount increased by treatment of L cells with Wnt3A was lowered by IGFBP-1, IGFBP-2, IGFBP-4, and IGFBP-6, but was not lowered by IGFBP-3 and IGFBP-5. In the figure, IGFBP-1, IGFBP-2, IGFBP-3, IGFBP-4, IGFBP-5, and IGFBP-6 are represented by BP1, BP2, BP3, BP4, BP5, and BP6, respectively.

FIG. 9-c shows that a TOPFLASH activity increased by treatment with Wnt3A in cells transfected with a TOPFLASH reporter gene was lowered by IGFBP-1, IGFBP-2, IGFBP-4, and IGFBP-6, but was not lowered by IGFBP-3 and IGFBP-5. In the figure, IGFBP-1, IGFBP-2, IGFBP-3, IGFBP-4, IGFBP-5, and IGFBP-6 are represented by BP1, BP2, BP3, BP4, BP5, and BP6, respectively.

FIG. 9-d shows that each of IGFBP-1, IGFBP-2, IGFBP-4, and IGFBP-6 interacted with LRP6, whereas IGFBP-3 and -5 did not interact with LRP6. The interaction was assessed by allowing LRP6N-Myc to react with each V5-tagged IGFBP, and performing immunoprecipitation (IP) with an anti-Myc antibody and subsequent immunoblotting (IB) with an anti-V5 antibody (upper panel), and immunoprecipitation (IP) with an anti-V5 antibody and subsequent immunoblotting (IB) with an anti-V5 antibody (lower panel). In the figure, IGFBP-1, IGFBP-2, IGFBP-3, IGFBP-4, IGFBP-5, and IGFBP-6 are represented by BP1, BP2, BP3, BP4, BP5, and BP6, respectively.

FIG. 9-e shows that each of IGFBP-1, IGFBP-2, IGFBP-4, and IGFBP-6 interacted with Frz8, whereas IGFBP-3 and -5 did not interact with Frz8. The interaction was assessed by allowing Frz8-Myc to react with each V5-tagged IGFBP, and performing immunoprecipitation (IP) with an anti-Myc antibody and subsequent immunoblotting (IB) with an anti-V5 antibody (upper panel), and immunoprecipitation (IP) with an anti-V5 antibody and subsequent immunoblotting (IB) with an anti-V5 antibody (lower panel). In the figure, IGFBP-1, IGFBP-2, IGFBP-3, IGFBP-4, IGFBP-5, and IGFBP-6 are represented by BP1, BP2, BP3, BP4, BP5, and BP6, respectively.

DETAILED DESCRIPTION OF THE PRESENT INVENTION

The present invention relates to an inhibitor of Wnt signalling, comprising as an active ingredient an effective amount of an insulin-like growth-factor-binding protein (IGFBP), the protein being capable of binding to a Wnt receptor. The inhibitor of Wnt signalling according to the present invention may be an inhibitor comprising one kind of insulin-like growth-factor-binding protein (IGFBP), the protein being capable of binding to a Wnt receptor, or may be an inhibitor comprising two or more kinds of the protein.

The term "Wnt signalling" refers to signalling generated in cells by the binding of Wnts, which belongs to the secretory glycoprotein ligand family, to the corresponding cell membrane receptors. The Wnt signalling is broadly classified into canonical Wnt signalling and non-canonical Wnt signalling. The canonical Wnt signalling refers to Wnt signalling that functions in a β-catenin-dependent manner, i.e., signalling wherein a Wnt protein binds to the Frizzled family as its cell surface receptor to activate a Disheveled family protein, resulting in the induction of nuclear localization of β-catenin to activate a transcription factor Tcf and promote the transcription of a Wnt-responsive gene. As the non-canonical Wnt signaling, two kinds of pathways called a PCP pathway and a $Ca^{2+}$ pathway has been known. The PCP pathway is characterized by the activation of a low molecular weight G protein Rho and Jun kinase belonging to the MAP kinase family. Further, the $Ca^{2+}$ pathway is characterized by the activation of downstream protein kinases PKC and calmodulin kinase through an increase in intracellular calcium concentration. The inhibitor of Wnt signalling according to the present invention is preferably an inhibitor of canonical Wnt signalling.

The IGFBP binds to a Wnt receptor to inhibit the binding of Wnt to the Wnt receptor, to thereby inhibit Wnt signalling. The Wnt receptor to which the IGFBP binds is exemplified preferably by Frizzled and LRP, more preferably by Frz8, LRP6, and LRP5. The phrase "bind to a Wnt receptor" means interacting by a non-covalent bond such as a hydrogen bond, a hydrophobic bond, or an electrostatic interaction so as to form a complex with a Wnt receptor protein. It is sufficient for the binding of a Wnt receptor and a protein that the Wnt receptor and the protein bind to each other in part of those molecules. The phrase "inhibit the binding of Wnt to the Wnt receptor" refers to attenuating the binding of Wnt to the Wnt receptor, or preventing the binding. The phrase "inhibit Wnt signalling" refers to inhibiting the generation of Wnt signals and/or attenuating Wnt signalling.

The IGFBP included in the inhibitor of Wnt signalling according to the present invention is not particularly limited as long as the IGFBP is capable of binding to a Wnt receptor. It is suitable to use IGFBP that binds to a Wnt receptor to inhibit Wnt signalling. Preferred examples of the IGFBP capable of binding to a Wnt receptor include IGFBP-1, IGFBP-2, IGFBP-4, and IGFBP-6. Any of IGFBP-1, IGFBP-2, IGFBP-4, and IGFBP-6 inhibited Wnt signalling elicited by Wnt3A (see Example 2). Among IGFBP-1, IGFBP-2, IGFBP-4, and IGFBP-6, IGFBP-4 exhibits the highest binding activity to a Wnt receptor and the highest Wnt signalling inhibitory action. Accordingly, a more preferred example of the IGFBP included in the inhibitor of Wnt signalling according to the present invention is IGFBP-4. The IGFBP may be derived from any species and is suitably derived from species identical to those of a subject, to which the inhibitor of Wnt signalling according to the present invention is applied, and tissues or cells derived from the subject. For example, when the inhibitor of Wnt signalling according to the present invention is applied to humans and human-derived tissues or cells, the IGFBP included in the inhibitor is preferably derived from humans.

A preferred example of IGFBP-4 is a human-derived protein represented by an amino acid sequence set forth in SEQ ID NO: 2.

A preferred example of IGFBP-1 is a human-derived protein represented by an amino acid sequence set forth in SEQ ID NO: 4.

A preferred example of IGFBP-2 is a human-derived protein represented by an amino acid sequence set forth in SEQ ID NO: 6.

A preferred example of IGFBP-6 is a human-derived protein represented by an amino acid sequence set forth in SEQ ID NO: 8.

The IGFBP included in the inhibitor of Wnt signalling according to the present invention encompasses a protein having sequence homology to a protein represented by an amino acid sequence set forth in any one selected from SEQ ID NO: 2, SEQ ID NO: 4, SEQ ID NO: 6, and SEQ ID NO: 8, the protein being capable of binding to a Wnt receptor. The sequence homology is generally about 50% or more, preferably about 70% or more, more preferably about 80% or more, still more preferably about 90% or more, yet still more preferably about 95% or more with respect to the entire amino acid sequence.

The IGFBP included in the inhibitor of Wnt signalling according to the present invention also encompasses a protein represented by an amino acid sequence having 1 or more, e.g., 1 to 100, preferably 1 to 30, more preferably 1 to 10, still more preferably 1 to 5, yet still more preferably 1 to 3, particularly preferably 1 or 2 amino acid mutations such as deletions, substitutions, additions, or insertions in the amino acid sequence set forth in any one selected from SEQ ID NO: 2, SEQ ID NO: 4, SEQ ID NO: 6, and SEQ ID NO: 8, the protein capable of binding to a Wnt receptor. The extent of mutations, positions thereof, and the like are not particularly limited as long as the protein having mutations is a protein capable of binding to a Wnt receptor, more preferably a protein inhibiting Wnt signalling. Such protein having mutations may be a protein generated by, for example, mutation and posttranslational modification in the nature, or may be a protein obtained by introducing mutations into a naturally occurring gene. Means for introducing mutations are known per se, and for example, a site-directed mutagenesis method, a gene homologous recombination method, a primer elongation method, or a polymerase chain reaction (PCR) may be used alone or in an appropriate combination thereof. For example, the methods described in books (Sambrook et al. ed., "Molecular Cloning, A Laboratory Manual 2nd ed.," 1989, Cold Spring Harbor Laboratory; Muramatsu, M. ed., "Genetic Engineering Lab Manual," 1988, Maruzen Co., Ltd.) or modified methods thereof may be used, and Ulmer's technique (Ulmer, K. M., "Science," 1983, Vol. 219, p. 666-671) may also be used. In view of not changing basic properties (physical properties, functions, bioactivity, immunological activity, etc.) of the protein in introduction of a mutation, for example, substitution between amino acids in the same class (polar amino acids, nonpolar amino acids, hydrophobic amino acids, hydrophilic amino acids, positively charged amino acids, negatively charged amino acids, aromatic amino acids, etc.) can be easily assumed.

The IGFBP capable of binding to a Wnt receptor may be selected, for example, by performing binding reactions of IGFBP with Wnt receptors Frz8 and LRP6. In place of Frz8 and LRP6, binding domains thereof to Wnts such as a cysteine-rich domain of Frz8 (Frz8CRD) and an extracellular portion of LPR6 (LRP6N) may be also used to perform such binding reactions (see Example 1). The binding reactions may be performed by conventional protein binding assays.

The IGFBP may be further modified by, for example, amidation of a component amino group, a carboxyl group or the like thereof as long as the modification causes no marked change in functions. Furthermore, this protein may be labeled by adding another protein or the like on the N-terminus or C terminus side directly or indirectly via a linker peptide or the like using a genetic engineering technique or the like. Preferably, labeling that does not inhibit basic properties of this protein is desired. Examples of proteins or the like to be added include enzymes such as glutathione S-transferase, β-galactosidase, horseradish peroxidase, or alkaline phosphatase, tag peptides such as His-tag, Myc-tag, HA-tag, FLAG-tag, or Xpress-tag, fluorescent substances such as fluorescein isothiocyanate or phycoerythrin, a maltose-binding protein, an immunoglobulin Fc fragment, biotin and so forth, but are not limited to these examples. Further, labelling may also be performed with a radioisotope. An inhibitor of Wnt signalling, comprising such labelled IGFBP, can be effectively utilized in the elucidation of Wnt signalling pathways and physiological events and diseases associated with the pathways.

A commercially available product may be purchased and utilized as the IGFBP. Alternatively, the IGFBP may be manufactured by a common chemical synthesis method. A solid-phase synthesis method, a liquid-phase synthesis method, and the like are known as chemical synthesis methods for a protein, and any of the methods may be used. More specifically, such protein synthesis methods include a so-called stepwise elongation method, in which each amino acid is bound one by one to extend the strand based on the amino acid sequence information, and a fragment condensation method, in which fragments comprising several amino acids are synthesized beforehand, and then each fragment is coupled, and this protein may be synthesized by either of the methods. The condensation method used in the above-mentioned protein synthesis may also be implemented according to a usual method, and examples thereof include azide methods, mixed anhydride methods, DCC methods, active ester methods, oxidation reduction methods, diphenylphosphoryl azide (DPPA) methods, DCC+additive (1-hydroxybenzotriazole, N-hydroxysuccinamide, N-hydroxy-5-norbornene-2,3-dicarboxyimide, etc.) methods, the Woodward method, and so forth. The IGFBP, which is obtained by chemical synthesis, may be further subjected to purification as required in accordance with various conventional purification methods. Separation and/or purification may be performed using as an indicator a function, such as a binding activity to IGF or a Wnt receptor, of the IGFBP. In a separation procedure, for example, ammonium sulfate precipitation, ultrafiltration, gel chromatography, ion-exchange chromatography, affinity chromatography, high-performance liquid chromatography, a dialysis method, or the like may be used alone or in an appropriate combination thereof. Preferably, it is recommended to use a method for specific adsorption using a specific antibody against IGFBP, such as affinity chromatography utilizing a column conjugated with the antibody.

The IGFBP may also be manufactured by a general genetic engineering technique (e.g., Sambrook J., Russell D. W., Molecular Cloning: A Laboratory Manual second edition, (1989) Cold Spring Harbor Laboratory; Ulmer K. M., Science, 219, 666-671 (1983); Ehrlich H. A., PCR Technology: Principles and Applications for DNA Amplification, (1989) Stockton Press, New York) based on sequence information of a gene encoding IGFBP. Specifically, the IGFBP may be acquired by preparing a cDNA library from various cells or tissues in which the expression of a gene encoding IGFBP has been confirmed or cultured cells derived from those cells or tissues in accordance with a conventional method, amplifying the gene using an appropriate primer unique for the gene, and inducing the expression of the resultant gene by a known genetic engineering technique. The expression of a gene encoding IGFBP-4 is observed at a high level in the liver and is also observed in, for example, the ovary, thyroid, and smooth muscle cells. The expression of a gene encoding IGFBP-1 is observed in the liver. The expression of a gene encoding IGFBP-2 is observed in, for example, the prostate, liver, heart, and pancreas. The expression of a gene encoding IGFBP-6 is observed in, for example, the smooth muscle, prostate, thyroid, and cardiomyocytes. The manufacture of the IGFBP using a genetic engineering technique may be specifically performed, for example, by first inserting a gene encoding IGFBP into an appropriate expression vector, introducing the resultant recombinant vector into appropriate host cells to produce a transformant, and then culturing the transformant to afford a culture. The expression vector and host cells may be appropriately selected from those generally used for the expression of a protein. Conditions and methods for culturing a transformant may be conditions and methods known per se optimum for a selected host. The IGFBP may be appropriately collected from the resultant culture. The IGFBP is a secretory protein and hence is produced not only in a transformant but also in a culture solution. Thus, the IGFBP may be collected from a homogenized product of the transformant after culturing or a culture solution by the above-mentioned various conventional purification methods.

The present invention also relates to an inhibitor of Wnt signalling, comprising as an active ingredient an effective amount of a polynucleotide encoding an insulin-like growth-factor-binding protein (IGFBP), the protein being capable of binding to a Wnt receptor. The inhibitor of Wnt signalling according to the present invention may include one kind of polynucleotide encoding an insulin-like growth-factor-binding protein (IGFBP), the protein being capable of binding to a Wnt receptor, or may include two or more kinds of the polynucleotide.

The introduction of the polynucleotide encoding an insulin-like growth-factor-binding protein (IGFBP), the protein being capable of binding to a Wnt receptor, into appropriate cells allows the IGFBP to be expressed in the cells. The IGFBP is a secretory protein and hence is secreted extracellularly. Accordingly, a medicament comprising the above-mentioned polynucleotide acts as an inhibitor of Wnt signalling via the expression of the IGFBP, when being introduced into cells. The introduction of a polynucleotide into cells may be performed by a conventionally used genetic engineering technique using an appropriate expression vector having inserted therein the polynucleotide. The inhibitor of Wnt signalling, comprising the polynucleotide encoding an insulin-like growth-factor-binding protein (IGFBP), the protein being capable of binding to a Wnt receptor, encompasses an inhibitor of Wnt signalling comprising an expression vector having inserted therein the polynucleotide (hereinafter, sometimes referred to as an IGFBP expression vector), and cells containing the polynucleotide and expressing the polynucleotide (hereinafter, sometimes referred to as IGFBP expressing cells). The IGFBP expressing cells may be preferably cells transfected with the IGFBP expression vector. The expression vector and the cells transfected with the expression vector may be appropriately selected from those generally used for the expression of a protein. For example, vector DNA is not particularly limited as long as being replicable in a host, and may be vector DNA which is lack of part of DNA portions excluding portions necessary for proliferation as well as vector DNA obtained by extracting naturally occurring DNA. Typical examples of the vector DNA include plasmid, bacteriophage, and virus-derived vector DNAs. Examples of the plasmid DNA include *Escherichia coli*-derived plasmid, *Bacillus subtilis*-derived plasmid, and yeast-derived plasmid. An example of the bacteriophage DNA is λ phage. Examples of the virus-derived vector DNA include vectors derived from animal viruses such as a retrovirus, a vaccinia virus, an adenovirus, a papovavirus, SV40, a Fowlpox virus, and a pseudorabies virus, or vectors derived from insect viruses such as a baculovirus. Further examples of the vector DNA include transposon-derived, insertion element-derived, and yeast chromosome element-derived vector DNAs. Still further examples of the vector DNA include vector DNAs prepared by combining those vector DNAs, specifically, vector DNAs (such as cosmids and phagemids) prepared by combining genetic elements of plasmids and bacteriophages. The cells are not particularly limited as long as those are cells derived from living organisms. Among those, preferred are animal-derived cells, more preferred are mammal-derived cells, and still more preferred are human-derived cells. When the cells are used as an active ingredient in an inhibitor, the cells are preferably isolated cells or cultured cells, more preferably cells subjected to growth inhibitory treatment. The growth inhibitory treatment of the cells may be performed by a known method such as radiation.

The polynucleotide included in the inhibitor of Wnt signalling according to the present invention is not particularly limited as long as the polynucleotide is a polynucleotide encoding an insulin-like growth-factor-binding protein (IGFBP), the protein being capable of binding to a Wnt receptor. It is suitable to use a polynucleotide encoding IGFBP that binds to a Wnt receptor to inhibit Wnt signalling. Preferred examples of the polynucleotide encoding IGFBP capable of binding to a Wnt receptor include a polynucleotide encoding IGFBP-1, a polynucleotide encoding IGFBP-2, a polynucleotide encoding IGFBP-4, and a polynucleotide encoding IGFBP-6. Out of IGFBP-1, IGFBP-2, IGFBP-4, and IGFBP-6, IGFBP-4 exhibits the highest binding activity to a Wnt receptor and the highest Wnt signalling inhibitory action. Accordingly, a more preferred example of the polynucleotide encoding IGFBP included in the inhibitor of Wnt signalling according to the present invention is a polynucleotide encoding IGFBP-4. The polynucleotide encoding IGFBP may be derived from any species and is suitably derived from species identical to that of a subject, to which the inhibitor of Wnt signalling according to the present invention is applied. For example, when the inhibitor of Wnt signalling according to the present invention is applied to humans or human-derived tissues or cells, the polynucleotide encoding IGFBP included in the inhibitor is preferably derived from humans.

A preferred example of the polynucleotide encoding IGFBP-4 is a human-derived polynucleotide represented by a base sequence set forth in SEQ ID NO: 1.

A preferred example of the polynucleotide encoding IGFBP-1 is a human-derived polynucleotide represented by a base sequence set forth in SEQ ID NO: 3.

A preferred example of the polynucleotide encoding IGFBP-2 is a human-derived polynucleotide represented by a base sequence set forth in SEQ ID NO: 5.

A preferred example of the polynucleotide encoding IGFBP-6 is a human-derived polynucleotide represented by a base sequence set forth in SEQ ID NO: 7.

The polynucleotide encoding IGFBP included in the inhibitor of Wnt signalling according to the present invention encompasses a polynucleotide having sequence homology to a polynucleotide represented by a base sequence set forth in any one selected from SEQ ID NO: 1, SEQ ID NO: 3, SEQ ID NO: 5, and SEQ ID NO: 7, the polynucleotide encoding a protein capable of binding to a Wnt receptor. The sequence homology is generally about 50% or more, preferably about 70% or more, more preferably about 80% or more, still more preferably about 90% or more, yet still more preferably about 95% or more with respect to the entire base sequence.

The polynucleotide encoding IGFBP included in the inhibitor of Wnt signalling according to the present invention also encompasses a polynucleotide represented by a base sequence having 1 or more, e.g., 1 to 100, preferably 1 to 30, more preferably 1 to 10, still more preferably 1 to 5, yet still more preferably 1 to 3, particularly preferably 1 or 2 nucleotide mutations such as deletions, substitutions, additions, or insertions in a base sequence set forth in any one selected from SEQ ID NO: 1, SEQ ID NO: 3, SEQ ID NO: 5, and SEQ ID NO: 7, the polynucleotide encoding a protein capable of binding to a Wnt receptor. The extent of mutations, positions thereof, and the like are not particularly limited as long as the polynucleotide having mutations is a polynucleotide encoding a protein capable of binding to a Wnt receptor, more preferably a polynucleotide encoding a protein that inhibits Wnt signalling. Such polynucleotide having mutations may be a naturally occurring polynucleotide, or may be a polynucleotide obtained by introducing mutations into a naturally occurring gene, such as a polynucleotide having induced mutations. Means for introducing mutations are known per se, and for example, a site-directed mutagenesis method, a gene homologous recombination method, a primer elongation method, PCR, or the like may be used alone or in an appropriate combination thereof.

The polynucleotide encoding IGFBP included in the inhibitor of Wnt signalling according to the present invention also encompasses a polynucleotide including the above-mentioned polynucleotide.

The selection of the polynucleotide encoding IGFBP capable of binding to a Wnt receptor may be performed, for example, by allowing a polynucleotide to be tested to be expressed in cells to afford a protein encoded by the polynucleotide, and performing binding reactions using Wnt receptors Frz8 and LRP6.

In place of Frz8 and LRP6, binding domains thereof to Wnts such as a cysteine-rich domain of Frz8 (Frz8CRD) and an extracellular portion of LPR6 (LRP6N) may be also used to perform such binding reactions (see Example 1). The binding reactions may be performed by conventional protein binding assays.

The present invention also relates to a method of inhibiting Wnt signalling, comprising using an insulin-like growth-factor-binding protein (IGFBP), the protein being capable of binding to a Wnt receptor. The method of inhibiting Wnt signalling according to the present invention may be a method comprising using one kind of insulin-like growth-factor-binding protein (IGFBP), the protein being capable of binding to a Wnt receptor, or may be a method comprising using two or more kinds of the protein.

The inhibition of Wnt signalling may be achieved by bringing an insulin-like growth-factor-binding protein (IGFBP), the protein being capable of binding to a Wnt receptor, into contact with cells having Wnt signalling pathways (hereinafter, sometimes referred to as target cells). Any of in vitro treatment and in vivo treatment allows the insulin-like growth-factor-binding protein (IGFBP), the protein being capable of binding to a Wnt receptor, to be brought into contact with the target cells. The in vitro treatment may be performed by adding the insulin-like growth-factor-binding protein (IGFBP), the protein being capable of binding to a Wnt receptor, to the culture of the target cells. The in vivo treatment may be performed by administering to a subject the protein capable of binding to a Wnt receptor.

The present invention also relates to a method of inhibiting Wnt signalling, comprising using a polynucleotide encoding an insulin-like growth-factor-binding protein (IGFBP), the protein being capable of binding to a Wnt receptor. The method of inhibiting Wnt signalling according to the present invention may be a method comprising using one kind of polynucleotide encoding an insulin-like growth-factor-binding protein (IGFBP), the protein being capable of binding to a Wnt receptor, or may be a method comprising using two or more kinds of the polynucleotide. The method of inhibiting Wnt signalling, comprising using a polynucleotide encoding an insulin-like growth-factor-binding protein (IGFBP), the protein being capable of binding to a Wnt receptor, encompasses a method of inhibiting Wnt signalling, comprising using an IGFBP expression vector and a method of inhibiting Wnt signalling, comprising using IGFBP expressing cells.

The inhibition of Wnt signalling may be achieved by introducing a polynucleotide encoding an insulin-like growth-factor-binding protein (IGFBP), the protein being capable of binding to a Wnt receptor, into cells. The IGFBP is a secretory protein. Hence, the IGFBP expressed in the cells is secreted extracellularly and inhibits the binding of Wnt to a Wnt receptor to inhibit Wnt signalling. Further, the IGFBP exhibits its effect in a paracrine fashion, and hence, the inhibition of Wnt signalling may be performed by treating target cells with IGFBP expressing cells that secrete IGFBP. The IGFBP expressing cells may be preferably cells transfected with an IGFBP expression vector. The treatment of the target cells with the polynucleotide encoding an insulin-like growth-factor-binding protein (IGFBP), the protein being capable of binding to a Wnt receptor, the IGFBP expression vector, and the IGFBP expressing cells may be any of in vitro treatment and in vivo treatment. The in vitro treatment may be performed by introducing the above-mentioned polynucleotide or IGFBP expression vector into cultured target cells by a known genetic engineering technique or adding the IGFBP expressing cells in the culture of target cells. The in vivo treatment may be performed by administering to a subject the above-mentioned polynucleotide, IGFBP expression vector, or IGFBP expressing cells. When the IGFBP expressing cells are administered in the in vivo treatment, the cells are preferably isolated cells or cultured cells, more preferably cells subjected to growth inhibitory treatment. The growth inhibitory treatment of the cells may be performed by a known method such as radiation. It is more preferred that cells harvested from a subject be transformed with an expression vector having inserted therein the polynucleotide encoding an insulin-like growth-factor-binding protein (IGFBP), the protein being capable of binding to a Wnt receptor, and then administered to the same subject.

The present invention also relates to a use of an insulin-like growth-factor-binding protein (IGFBP), the protein being capable of binding to a Wnt receptor, and/or a polynucleotide encoding the protein, in the manufacture of an inhibitor of Wnt signalling.

The present invention also relates to a medicament for the prevention and/or treatment of a disease due to enhanced Wnt signalling, comprising as an active ingredient an effective amount of the above-mentioned inhibitor of Wnt signalling. The present invention also relates to a method for the prevention and/or treatment of a disease due to enhanced Wnt signalling, comprising using the above-mentioned inhibitor of Wnt signalling. The present invention also relates to a use of the above-mentioned inhibitor of Wnt signalling in the prevention and/or treatment of a disease due to enhanced Wnt signalling.

Wnts are proteins that control morphogenesis, and are known to be involved in various phenomena such as development, stem cell differentiation control, and cell malignant transformation. Further, there are reports that Wnts are important factors for the growth regulation and survival of stem cells (Non-Patent References 5 and 6). Accordingly, abnormalities in Wnt signalling cause diseases due to abnormal development such as congenital cardiac failure, and diseases according to abnormal cell function such as cancer diseases.

Canonical Wnt signalling plays a crucial role in cardiomyocyte differentiation (Non-Patent References 2 and 4). It has also been shown that the canonical Wnt signalling inhibits cardiogenesis in chick and frog embryos, and that Wnt antagonists such as dickkopf (Dkk) and crescent secreted from anterior endoderm or organizer region counteract the Wnt-mediated inhibitory signals and induce cardiogenesis in the anterior lateral mesoderm (Naito, A. T. et al., Developmental stage-specific biphasic roles of Wnt/beta-catenin signaling in cardiomyogenesis and hematopoiesis., Proc Natl Acad Sci USA 103, 19812-7 (2006); Tzahor, E. & Lassar, A. B., Wnt signals from the neural tube block ectopic cardiogenesis., Genes Dev 15, 255-60 (2001); Schneider, V. A. & Mercola, M., Wnt antagonism initiates cardiogenesis in *Xenopus laevis*., Genes Dev 15, 304-15 (2001); Marvin, M. J., Di Rocco, G., Gardiner, A., Bush, S. M. & Lassar, A. B., Inhibition of Wnt activity induces heart formation from posterior mesoderm., Genes Dev 15, 316-27 (2001)). It has been shown that the canonical Wnt signalling exhibits time-dependent effects on cardiogenesis in ES cells. The canonical Wnt signalling in the early phase of ES cell differentiation promotes cardiomyogenesis, whereas the canonical Wnt signalling in the late phase inhibits cardiomyocyte differentiation (Naito, A. T. et al., Developmental stage-specific biphasic roles of Wnt/beta-catenin signaling in cardiomyogenesis and hematopoiesis., Proc Natl Acad Sci USA 103, 19812-7 (2006); Ueno, S. et al., Biphasic role for Wnt/beta-catenin signaling in cardiac specification in zebrafish and embryonic stem cells., Proc Natl Acad Sci USA 104, 9685-90 (2007); Liu, Y. et al., Sox17 is essential for the specification of cardiac mesoderm in embryonic stem cells., Proc Natl Acad Sci USA 104, 3859-64 (2007)). Similar time-dependent effects of the canonical Wnt signalling have been shown in zebrafish embryos (Ueno, S. et al., Biphasic role for Wnt/beta-catenin signaling in cardiac specification in zebrafish and embryonic stem cells., Proc Natl Acad Sci USA 104, 9685-90 (2007)). In addition, several recent reports suggest that the canonical Wnt signalling is a positive regulator of cardiac progenitor cell proliferation in the secondary heart field (Lin, L. et al., Beta-catenin directly regulates Islet1 expression in cardiovascular progenitors and is required for multiple aspects of cardiogenesis., Proc Natl Acad Sci USA 104, 9313-8 (2007); Ai, D. et al., Canonical Wnt signaling functions in second heart field to promote right ventricular growth., Proc Natl Acad Sci USA 104, 9319-24 (2007); Kwon, C. et al., Canonical Wnt signaling is a positive regulator of mammalian cardiac progenitors., Proc Natl Acad Sci USA 104, 10894-9 (2007); Cohen, E. D. et al., Wnt/beta-catenin signaling promotes expansion of Isl-1-positive cardiac progenitor cells through regulation of FGF signaling., J Clin Invest 117, 1794-804 (2007); Qyang, Y. et al., The Renewal and Differentiation of Isl1$^+$ Cardiovascular Progenitors Are Controlled by a Wnt/beta-Catenin Pathway., Cell Stem Cell 1, 165-79 (2007)). As described above, the canonical Wnt signalling exhibits divergent effects on cardiogenesis at multiple stages of development. That is, the canonical Wnt signalling (i) promotes cardiogenesis at the time of gastrulation or mesoderm specification, (ii) inhibits cardiogenesis at the time when cardiac mesoderm is specified in the anterior lateral mesoderm, (iii) promotes the expansion of cardiac progenitors in the secondary heart field, and (iv) inhibits cardiogenesis at later stages when the embryonic heart is growing.

Thus, the inhibitor of Wnt signalling according to the present invention may be used for the preparation of cardiomyocytes through the induction of cardiomyocyte differentiation, and may be further applied to the induction of cardiac development. Indeed, the IGFBP included in the inhibitor of Wnt signalling according to the present invention induced cardiomyocyte differentiation (see Example 1). Specifically, IGFBP-4 induced the cardiomyocyte differentiation of a mouse-derived cell line, P19CL6 cells and embryonic stem cells (ES cells). Further, IGFBP-4 knockdown or Wnt pathway activation impaired normal cardiac development in *Xenopus* embryos, but the cardiac defects due to IGFBP-4 knockdown were rescued by the expression of IGFBP-4 that is resistant to the knockdown. Such cardiomyocyte inducing activity and cardiogenic activity of IGFBP-4 are resulting from a Wnt signalling inhibitory action of IGFBP-4. The inhibition of Wnt signalling in cardiac development is required at later stages of development, when the heart has been already formed at the ventral portion to start to grow and remodel to maintain embryonic circulation. Accordingly, the IGFBP is preferably applied in the late phase after embryoid body formation, when being used for, for example, the cardiomyocyte differentiation of ES cells.

The term "differentiation" or the phrase "differentiation of cells" refers that so-called non-differentiated cells having no particular morphological and functional features generate cells having particular morphological and functional features through the division of the cells. Further, in the process of differentiation, a particular gene, which has not been observed in the non-differentiated cells, is expressed. The expression of such gene is also included in the "differentiation". The phrase "induction of differentiation" refers to generating cells having morphological and functional features from the non-differentiated cells. Further, it is also included in the "induction of differentiation" to make the expression of a particular gene, which has not been observed in the non-differentiated cells.

The term "cardiomyocyte differentiation" means that cells having morphological and functional features as cardiomyocytes are generated by the division of non-differentiated cells. Further, the expression of a gene characteristic for cardiomyocytes is also included in the "cardiomyocyte differentiation". The cardiomyocytes exhibit adhesiveness and extensibility as the morphological features. The cardiomyocytes exhibit autonomous beating during stratification as the functional features. Examples of the gene characteristic for cardiomyocytes include cardiac marker genes such as an α myosin heavy chain (αMHC) gene, an Nkx2.5 gene, a GATA-4 gene, and a cardiac troponin T (cTnT) gene. The phrase "induction of cardiomyocyte differentiation" refers to generating cells having morphological and functional features of cardiomyocytes from non-differentiated cells. Further, it is also included in the "induction of cardiomyocyte differentiation" to make expression of the gene characteristic for cardiomyocytes.

In the present invention, there can be provided a medicament for the induction of cardiomyocyte differentiation, comprising an effective amount of the above-mentioned inhibitor of Wnt signalling, and a method of inducing cardiomyocyte differentiation, comprising using the above-mentioned inhibitor of Wnt signalling. The induction of cardiomyocyte differentiation may be achieved by bringing the above-mentioned inhibitor of Wnt signalling into contact with cells capable of differentiating into cardiomyocytes. Examples of the cells capable of differentiating into cardiomyocytes include pluripotent stem cells. The term "pluripotent stem cells" refers to cells that are capable of differentiating into cells having functional and morphological features to form various tissues or organs and having self-renewal ability. Examples of the pluripotent stem cells include tissue stem cells, embryonic stem cells (ES cells), and artificial pluripotent stem cells. The tissue stem cells refer to non-differentiated cells that are present in adult tissues and have self-renewal ability. Examples of the tissue stem cells include bone marrow-derived stem cells and heart-derived stem cells. The ES cells refer to a stem cell line made from interior cell mass belonging to part of blastocyst-stage embryos at the early stage of animal development, which are capable of differentiating into cells having functional and morphological features to form various tissues or organs. The artificial pluripotent stem cells refer to pluripotent cells obtained by introducing several kinds of transcription factor genes into somatic cells such as fibroblasts. Any of in vitro treatment and in vivo treatment allows the above-mentioned inhibitor of Wnt signalling to be brought into contact with cells capable of differentiating into cardiomyocytes. The in vitro treatment may be performed by adding the above-mentioned inhibitor of Wnt signalling in the culture of the cells. The in vivo treatment may be performed by administering to a subject the above-mentioned inhibitor of Wnt signalling.

In the present invention, there can also be provided cardiomyocytes, which are obtained by the above-mentioned method of inducing cardiomyocyte differentiation, and a use thereof. The cardiomyocytes are preferably cultured cardiomyocytes. The completion of the induction of the cardiomyocytes may be confirmed by the expression of cardiac marker genes such as an α myosin heavy chain (αMHC) gene, an Nkx2.5 gene, and a GATA-4 gene in the cells and the expression of a cardiac troponin T (cTnT) protein. The expression of those genes may be measured by a gene detection method known per se. Specific examples of the gene detection method include plaque hybridization, colony hybridization, a Southern blot method, a northern blot method, a nucleic acid sequence-based amplification (NASBA) method, or RT-PCR. There are also given gene detection methods at a cell level utilizing, for example, in situ RT-PCR and in situ hybridization. Alternatively, a protein encoded by the gene may be detected using an antibody that specifically recognizes the protein.

The cardiomyocytes to be provided by the method of inducing cardiomyocyte differentiation according to the present invention may be used for construction or reconstruction of myocardial tissues in vitro or in vivo. In recent years, extensive studies have been made on regenerative medicine based on the reconstruction of myocardial tissues as a method for the treatment of cardiac failure. The cardiac failure refers to a pathophysiological condition in which cardiac functions such as cardiac contractile force and expansive force are lowered, resulting in insufficient blood circulation necessary for systemic tissues, and is a pathology that occurs at the terminal stage of any of cardiac diseases such as cardiomyopathy, myocardial infarction, and valvular heart disease. In most of such cardiac diseases, damaged and degenerated myocardial tissues are observed. The reconstruction of the damaged and degenerated myocardial tissues allows the treatment of those diseases and the prevention and/or treatment of cardiac failure. The reconstruction of myocardial tissues may be performed by injecting cardiomyocytes into the damaged and degenerated myocardial tissues, or transplanting a cardiomyocyte sheet obtained by culturing cardiomyocytes or multilayered cardiomyocytes including stacked cardiomyocyte sheets by a surgical technique. Further, the multilayered cardiomyocytes have been reported to exhibit autonomous beating when being transplanted into a living body, and may be used as the heart for transplantation. As described above, the cardiomyocytes to be provided by the method of the present invention are useful for the construction or reconstruction of myocardial tissues, and hence can be used for a manipulation for the purpose of myocardial restoration in the damaged and degenerated heart. In addition, the cardiomyocytes can be used for the treatment of a variety of cardiac diseases such as cardiomyopathy, myocardial infarction, and valvular heart disease.

There are further reports on the association of Wnt signalling with diseases that the activation thereof is associated with several types of malignant tumors (Logan, C. Y. & Nusse, R., The Wnt signaling pathway in development and disease., Annu Rev Cell Dev Biol 20, 781-810 (2004); Clevers, H., Wnt/beta-catenin signaling in development and disease., Cell 127, 469-80 (2006)). Accordingly, the inhibitor of Wnt signalling according to the present invention can be applied to the prevention and/or treatment of cancer diseases. Meanwhile, it has been shown that IGFBP-4 treatment attenuated in vitro cell proliferation in several cancer cell lines, and that IGFBP-4 overexpression attenuated the in vivo growth of prostate cancer (Durai, R. et al., Biology of insulin-like growth factor binding protein-4 and its role in cancer (review)., Int J Oncol 28, 1317-25 (2006)). Further, decreased serum levels of IGFBP-4 are associated with the risk of breast cancer. IGFs are known to exhibit a cell proliferation action, and hence, it has been conventionally recognized that IGFBP-4 binds to the IGFs to inhibit the cell proliferation action, to thereby exhibit a cancer inhibitory action. However, there is a possibility that the inhibitory effect of IGFBP-4 on cell proliferation is mediated in part by the inhibition of canonical Wnt signalling.

The medicament according to the present invention may be prepared as a pharmaceutical composition further including, as necessary, various kinds of commonly used pharmaceutical carriers in addition to an active ingredient. Examples of the pharmaceutical carriers may include one or more kinds of pharmaceutically acceptable excipients, disintegrants, diluents, lubricants, flavors, colorants, sweetners, taste masking agents, suspending agents, wetting agents, emulsifiers, dispersants, aids, preservatives, buffers, binders, stabilizers, and coating agents. Further, the inhibitor of Wnt signalling according to the present invention may be prepared as a pharmaceutical composition including not only the pharmaceutical carriers but also a known inhibitor of Wnt signalling. In addition, the medicament for the induction of cardiomyocyte differentiation according to the present invention may be prepared as a pharmaceutical composition including not only the pharmaceutical carriers but also a known medicament for the induction of cardiomyocyte differentiation.

The amount of an active ingredient included in the medicament or pharmaceutical composition according to the present invention may be appropriately determined depending on, for example, the dose range or dosing frequency of the active ingredient. The amount is, for example, about 0.1 μg or more, preferably 1 μg or more, more preferably 10 μg or more, still more preferably 100 μg or more, yet still more preferably 1 mg or more.

In the case of applying the medicament or pharmaceutical composition according to the present invention in vitro, the dose and application condition may be determined by simple repetitive experiments. With regard to the dose of the medicament or pharmaceutical composition according to the present invention, for example, when being applied to cultured cells, the medicament or pharmaceutical composition is effective at a concentration in the range of generally about 1 ng/ml to about 1 mg/ml, preferably about 10 ng/ml to about 100 μg/ml, more preferably about 100 ng/ml to about 10 μg/ml, still more preferably about 100 ng/ml to about 1 μg/ml.

When the medicament or pharmaceutical composition according to the present invention is administered to a subject, the dose range is not particularly limited and appropriately selected depending on, for example, the effectiveness, modes of administration, and routes of administration of an ingredient to be incorporated, kinds of diseases, properties of a subject (such as body weight, age, medical condition, and presence or absence of a use of any other pharmaceutical), and judgement of a doctor in attendance. When the medicament according to the present invention is administered to a subject, a generally appropriate dose is preferably in the range of, for example, about 0.01 μg to about 100 mg, preferably about 0.1 μg to about 1 mg per kg of body weight of the subject. However, such dose may be modified using a common routine experiment for optimization well known in the art. The above-mentioned dosage may be administered at one time or in several divided portions daily.

Any of the routes of administration, i.e., systemic administration or local administration may be selected. In this case, an appropriate route of administration is selected depending on, for example, diseases or symptoms. The medicament according to the present invention may be administered through any of an oral route and a parenteral route. Examples of the parenteral route include subcutaneous administration, intradermal administration, and intramuscular administration in addition to general intravenous administration and intraarterial administration. In addition, transmucosal administration or transdermal administration may be performed.

The dosage form is not particularly limited, the medicament or pharmaceutical composition may be formulated into a variety of dosage forms. Examples of the dosage form include but not limited to: tablets, capsules, powders, granules, pills, liquids, emulsions, suspensions, solutions, spirits, syrups, extracts, and elixirs for oral administration; parenteral formulations including injections such as subcutaneous injections, intravenous injections, intramuscular injections, intraperitoneal injections; transdermal formulations or patches and ointments or lotions; sublingual formulations and buccal patches for buccal administration; aerosols for transnasal administration; and suppositories. Those formulations may be manufactured by a known method commonly used in a formulation process.

In the case of preparing oral solid formulations, an excipient, and as necessary, a binder, a disintegrant, a lubricant, a colorant, a taste masking agent, an odor masking agent, and the like may be added to an active ingredient to manufacture tablets, coated tablets, granules, powders, capsules, and the like by a conventional method. Such additives may be ones generally used in the art. Examples of the excipient include lactose, white soft sugar, sodium chloride, glucose, starch, calcium carbonate, kaolin, microcrystalline cellulose, and silicic acid. Examples of the binder include water, ethanol, propanol, a simple syrup, a glucose solution, a starch solution, a gelatin solution, carboxymethyl cellulose, hydroxypropyl cellulose, hydroxypropyl starch, methyl cellulose, ethyl cellulose, shellac, calcium phosphate, and polyvinylpyrrolidone. Examples of the disintegrant include dry starch, sodium alginate, powdered agar, sodium hydrogen carbonate, calcium carbonate, sodium lauryl sulfate, stearic acid monoglyceride, and lactose. Examples of the lubricant include purified talc, a stearic acid salt, borax, and polyethylene glycol. Examples of the taste masking agent include white soft sugar, orange peel, citric acid, and tartaric acid.

In the case of preparing oral liquid formulations, a taste masking agent, a buffer, a stabilizer, an odor masking agent, and the like may be added to an active ingredient to manufacture liquids for internal use, syrups, elixirs, and the like by a conventional method. In this case, the taste masking agent may be as exemplified above, an example of the buffer is sodium citrate, and examples of the stabilizer include tragacanth, gum arabic, and gelatin.

In the case of preparing injections, a pH adjustor, a buffer, a stabilizer, a tonicity adjusting agent, a local anesthetic, and the like may be added to an active ingredient to manufacture subcutaneous, intramuscular, and intravenous injections by a conventional method. In this case, examples of the pH adjustor and buffer include sodium citrate, sodium acetate, and sodium phosphate. Examples of the stabilizer include sodium pyrosulfite, ethylenediaminetetraacetic acid (EDTA), thioglycolic acid, and thiolactic acid. Examples of the local anesthetic include procaine hydrochloride and lidocaine hydrochloride. Examples of the tonicity adjusting agent include sodium chloride and glucose.

In the case of preparing suppositories, carriers for formulation known in the art such as polyethylene glycol, lanolin, cacao butter, and fatty acid triglyceride, and further as necessary, a surfactant such as a Tween (registered trademark) and the like may be added to an active ingredient to manufacture suppositories by a conventional method.

In the case of preparing ointments, a generally used base, stabilizer, wetting agent, preservative, and the like may be incorporated into an active ingredient as necessary, and the resultant is mixed and formulated into ointments by a conventional method. Examples of the base include liquid paraffin, white petrolatum, white beeswax, octyldodecyl alcohol, and paraffin. Examples of the preservative include methyl parahydroxybenzoate, ethyl parahydroxybenzoate, and propyl parahydroxybenzoate.

In the case of manufacturing patches, one has only to apply the ointment, a cream, a gel, a paste, or the like onto a general support by a conventional method. The support is suitably a fabric or a nonwoven fabric made of cotton, staple fibers, or chemical fibers, or a film or a foam sheet made of flexible vinyl chloride, polyethylene, polyurethane, or the like.

Further, the medicament according to the present invention may be in a sustained-release or controlled-release dosage form.

The medicament and pharmaceutical composition according to the present invention are generally preferably prepared as injections, drops, or liposome formulations when being each used as a gene therapeutic agent. The gene therapeutic agent may also be prepared, for example, in such a form that the cells are incorporated into phosphate-buffered physiological saline (pH 7.4), a Ringer's solution, and an intracellular composition injection when being prepared in a form including gene-transfected cells. Alternatively, the gene therapeutic agent may also be prepared in such a form that the agent is administered together with a substance for enhancing gene transfer efficiency such as protamine. The pharmaceutical composition of the present invention may be administered in one portion or in several divided portions daily, or may be intermittently administered at an interval of 1 day to several weeks when being used as the gene therapeutic agent. The administration may be performed in accordance with a method used in a common method for gene therapy.

EXAMPLES

Hereinafter, the present invention is described in more detail by way of examples. However, the present invention is by no means limited by the following examples.

Example 1

[1] Materials and Methods (Plasmids and Reagents)

Mouse IGFBP and *Xenopus* IGFBP-4 (hereinafter, sometimes abbreviated as XIGFBP-4) cDNA clones were purchased from Open Biosystmes. A mutant (XIGFBP-4-H74P) in which the 74th histidine (His) is replaced by proline (Pro) in XIGFBP-4 was produced by a QuikChange (registered trademark) Site-Directed Mutagenesis kit (manufactured by Stratagene). Such mutant does not bind to IGFs. His-tagged human wild-type IGFBP-4 and mutant IGFBP-4-H74P (Qin, X., Strong, D. D., Baylink, D. J. & Mohan, S., Structure-function analysis of the human insulin-like growth factor binding protein-4., J Biol Chem 273, 23509-16 (1998)) were produced using a HitTrap HP kit (manufactured by Amersham) and then purified.

Soluble forms of LRP6 deletion mutants and probes for in situ hybridization analysis (Nkx2.5, cTnI, and Hex) were generated by PCR. IGFBP-4, Wnt3A, IGF-I, IGF-II, and BMP2 were purchased from R&D. Neutralizing antibodies were purchased from R&D (anti-I GFBP-4 antibody), Sigma (anti-IGF-I antibody and anti-IGF-II antibody), and Oncogene (anti-type I IGF receptor antibody). Antibodies used for immunoprecipitation, western blotting, and immunostaining were purchased from Invitrogen (anti-Myc antibody and anti-V5 antibody), Santa Cruz (anti-troponin T (cTnT) antibody, anti-IGFBP-4 antibody, anti-topoisomerase I (TOPO-I) antibody, Sigma (anti-β-actin antibody, anti-β-catenin antibody, and anti-FLAG (M2) antibody), and Developmental Studies Hybridoma Bank (anti-sarcomeric myosin heavy chain antibody (MF20)).

Full-length Frz8, a cysteine-rich domain of Frz8 (Frz8CRD), and an extracellular portion of LRP6 (LRP6N) are described in the references (He, X. et al., A member of the Frizzled protein family mediating axis induction by Wnt-5A., Science 275, 1652-4 (1997); Tamai, K. et al., LDL-receptor-related proteins in Wnt signal transduction., Nature 407, 530-5 (2000)). Full-length LRP6, membrane-bound forms of LRP6 deletion mutants, and dickkopf-1 (DKK1) are described in the reference (Mao, B. et al., LDL-receptor-related protein 6 is a receptor for Dickkopf proteins., Nature 411, 321-5 (2001)). pXwnt8 and pCSKA-Xwnt8, which are *Xenopus* Wnt8 (Xwnt8) expression vectors, are described in the references (Christian, J. L., McMahon, J. A., McMahon, A. P. & Moon, R. T., Xwnt-8, a *Xenopus* Wnt-1/int-1-related gene responsive to mesoderm-inducing growth factors, may play a role in ventral mesodermal patterning during embryogenesis., Development 111, 1045-55 (1991); Christian, J. L. & Moon, R. T., Interactions between Xwnt-8 and Spemann organizer signaling pathways generate dorsoventral pattern in the embryonic mesoderm of *Xenopus*., Genes Dev 7, 13-28 (1993)). PCS2-β-catenin, which is a β-catenin expression vector, is described in the reference (Yost, C. et al., The axis-inducing activity, stability, and subcellular distribution of beta-cateninis regulated in *Xenopus* embryos by glycogen synthase kinase 3., Genes Dev 10, 1443-54 (1996)). αMHC-GFP, which is an expression vector of a green fluorescent protein (GFP) to be controlled by an α myosin heavy chain (αMHC) promoter, is described in the reference (Kolossov, E. et al., Identification and characterization of embryonic stem cell-derived pacemaker and atrial cardiomyocytes., FASEB J 19, 577-9 (2005)). BRE-luc, which is a BMP-responsive reporter gene, is described in the reference (Korchynskyi, O. & ten Dijke, P., Identification and functional characterization of distinct critically important bone morphogenetic protein-specific response elements in the Id1 promoter., J Biol Chem 277, 4883-91 (2002)). pCGN-Dv1-1, which is a Disheveled-1 (Dv1-1) expression vector, is described in the reference (Kishida, M. et al., Synergistic activation of the Wnt signaling pathway by Dv1 and casein kinase Iepsilon., J Biol Chem 276, 33147-55 (2001)).

(Cell Culture Experiment)

The induction of cardiomyocyte differentiation and culture of P19CL6 cells and ES cells were performed by essentially the same methods as those described in previous reports (Monzen, K. et al., Bone morphogenetic proteins induce cardiomyocyte differentiation through the mitogen-activated protein kinase kinase kinase TAK1 and cardiac transcription factors Csx/Nkx-2.5 and GATA-4., Mol Cell Biol 19, 7096-105 (1999); Naito, A. T. et al., Developmental stage-specific biphasic roles of Wnt/beta-catenin signaling in cardiomyogenesis and hematopoiesis., Proc Natl Acad Sci USA 103, 19812-7 (2006)).

P19CL6 cells or ES cells stably transfected with αMHC-GFP were generated by transfection of αMHC-GFP into P19CL6 cells or ht7 ES cells and subsequent selection using G418.

Luciferase reporter gene assays, western blot assays, immunostaining, and RT-PCR were performed by the same methods as those described in the previous report (Naito, A. T. et al., Developmental stage-specific biphasic roles of Wnt/beta-catenin signaling in cardiomyogenesis and hematopoiesis., Proc Natl Acad Sci USA 103, 19812-7 (2006)). The reporter gene assays were conducted repeatedly at least three times.

PCR primers and PCR conditions are listed in Table 1.

TABLE 1

| Gene | Primer | SEQ ID NO | PCR product (bp) | Annealing (° C.) |
|---|---|---|---|---|
| αMHC | 5'-GGAAGAGTGAGCGGCCATCAAGG-3'<br>5'-CTGCTGGAGAGGTTATTCCTCG-3' | 9<br>10 | 302 | 65 |
| Nkx2.5 | 5'-CAGTGGAGCTGGACAAAGCC-3'<br>5'-TAGCGACGGTTCTGGAATTT-3' | 11<br>12 | 216 | 55 |
| GATA-4 | 5'-CTGTCATCTCACTATGGGCA-3'<br>5'-CCAAGTCCGAGCAGGAATTT-3' | 13<br>14 | 275 | 60 |
| β-Actin | 5'-GGACCTGGCTGGCCGGGACC-3'<br>5'-GCGGTGCACGATGGAGGGGC-3' | 15<br>16 | 583 | 60 |
| IGFBP-1 | 5'-CCAGGGATCCAGCTGCCGTGCG-3'<br>5'-GGCGTTCCACAGGATGGGCTG-3' | 17<br>18 | 259 | 60 |
| IGFBP-2 | 5'-CAACTGTGACAAGCATGGCCG-3'<br>5'-CACCAGTCTCCTGCTGCTCGT-3' | 19<br>20 | 176 | 60 |
| IGFBP-3 | 5'-GACACCCAGAACTTCTCCTCC-3'<br>5'-CATACTTGTCCACACACCAGC-3' | 21<br>22 | 220 | 60 |
| IGFBP-4 | 5'-CGTCCTGTGCCCCAGGGTTCCT-3'<br>5'-GAAGCTTCACCCCTGTCTTCCG-3' | 23<br>24 | 200 | 60 |
| IGFBP-5 | 5'-GTTTGCCTCAACGAAAAGAGCT-3'<br>5'-CTGCTTTCTCTTGTAGAATCCTT-3' | 25<br>26 | 393 | 60 |
| IGFBP-6 | 5'-CCCCGAGAGAACGAAGAGACG-3'<br>5'-CTGCGAGGAACGACACTGCTG-3' | 27<br>28 | 351 | 60 |
| XIGFBP-4 (MO-s) | 5'-CAAACTCATTCATCTCCAGCCC-3'<br>5'-TTCCTTTCCCCTCTCAGATGCC-3' | 29<br>30 | 808 | 55 |
| XIGFBP-4 (MO-r) | 5'-ATGTCAGGTTACTGTCATCCTGCCC-3'<br>51-TTCCTTTCCCCTCTCAGATGCC-3' | 31<br>30 | 767 | 55 |
| Siamois | 5'-TACCGCACTGACTCTGCAAG-3'<br>5'-CTGAGGCTCCTGTGGAATTC-3' | 32<br>33 | 192 | 62 |
| Xnr 3 | 5'-CTTCTGCACTAGATTCTG-3'<br>5'-CAGCTTCTGGCCAAGACT-3' | 34<br>35 | 281 | 58 |
| ODC | 5'-GTCAATGATGGAGTGTATGGATC-3'<br>5'-TCCAATCCGCTCTCCTGAGCAC-3' | 36<br>37 | 386 | 55 |

The small interfering RNA (siRNA) construct-mediated knockdown of IGFBPs was performed by intracellularly expressing siRNAs using pSIREN-RetroQ vectors (manufactured by Clontech). Specifically, pSIREN-RetroQ vectors ligated with double-strand oligonucleotides were transfected into P19CL6 cells or ES cells, and puromycin-resistant clones were isolated and then proliferated.

Base sequences of oligonucleotides that form the double-strand oligonucleotides are listed in Table 2.

TABLE 2

| Gene | Oligonucleotide sequence | SEQ ID NO |
|---|---|---|
| mIGFBP-3 | AATCCTAGATGAAGTGTTA | 38 |
| mIGFBP-4-1 | GAGCCAGGCTGCGGTTGTT | 39 |
| mIGFBP-4-2 | GCAAGTGCTGGTGTGTGGA | 40 |
| mIGFBP-5 | AAGGCCTCCAAGCTAATTA | 41 |
| XIGFBP-4-MO1 | GCAGGGTGGCAATATCCAGACATGA | 42 |
| XIGFBP-4-MO2 | CTTGCTGGGCTGGAGATGAATGAGT | 43 |

β-Catenin stabilization assays were performed using nuclear extracts of L cells. The nuclear extracts of L cells were prepared using an NE-PER Nuclear and Cytoplasmic Extraction reagent (manufactured by Pierce). Data are shown as mean±standard deviation.

(Immunoprecipitation (IP)/Western Analyses and Binding Assays)

Conditioned media each including full-length IGFBP or various deletion mutants thereof, LRP6, Frz8CRD, and DKK1 were produced using 293 cells, and IP/western analysis was performed using those media. Binding reactions were performed at 4° C. overnight. Immunoprecipitation was performed using a Protein G Sepharose 4 Fast Flow (manufactured by Amersham). The $^{125}$I-labelling of IGFBP-4 and Wnt3A was performed using an IODO-BEADS (registered trademark) iodization reagent (manufactured by Pierce). A liquid-phase binding assay was basically performed by the same method as that previously reported (Semenov, M. V. et al., Head inducer Dickkopf-1 is a ligand for Wnt coreceptor LRP6., Curr Biol 11, 951-61 (2001)). In brief, Myc-tagged LRP6N (LRP6N-Myc) or Myc-tagged Frz8CRD (Frz8CRD-Myc) was mixed with various concentrations of $^{125}$I-labelled IGFBP-4, and then incubated at 4° C. overnight. LRP6N-Myc or Frz8CRD- Myc was immunoprecipitated, and the radioactivity of bound IGFBP-4 was measured after extensive washing of the Protein G Sepharose beads. For a competitive binding assay, conditioned media including LRP6N-Myc or Frz8CRD-Myc were mixed with $^{125}$I-labelled Wnt3A and non-labelled IGFBP-4, and then incubated at 4° C. overnight. Next, LRP6N-Myc or Frz8CRD-Myc was immunoprecipitated, and the radioactivity of bound Wnt3A was measured.

(Xenopus Experiments and Mouse In Situ Hybridization Analysis)

Axis duplication assays, animal cap assays, and in situ hybridization analyses in Xenopus were basically performed by the same methods as those previously reported (Kobayashi, H. et al., Novel Daple-like protein positively regulates both the Wnt/beta-catenin pathway and the Wnt/JNK pathway in Xenopus., Mech Dev 122, 1138-53 (2005)). Two independent cDNAs for XIGFBP-4, presumably resulting from pseudotetraploid genomes, were identified by a rapid amplification of cDNA ends (5'RACE) method. Two independent MOs that target both of those two IGFBP-4 transcripts were designed (Gene Tools). MO1 targets a sequence consisting of 25 nucleotides from the 2nd nucleotide adjacent to the upstream of a translation start codon to the 23th nucleotide in the translation region, and MO2 targets a sequence consisting of 25 nucleotides in the untranslated region. MO-sensitive XIGFBP-4 cDNA, which includes a 41 bp 5'-untranslated region, was generated by PCR. MO-resistant XIGFBP-4 cDNA (wild-type and H74P mutant) was generated by introducing five silent mutations in the MO1 target sequence and excluding a 5'-untranslated region. In order to determine the specificity of MOs, MO-sensitive or MO-resistant XIGFBP-4-Myc mRNA was injected into Xenopus embryos with or without MOs, and protein and mRNA expression was analyzed. PCR primers and PCR conditions are listed in Table 1 above. MOs and plasmid DNAs were injected at the 8-cell stage into the dorsal region of two dorsal-vegetal blastomeres fated to be heart and liver anlage. The introduction of mRNA by electroporation was performed by essentially the same method as that previously reported (Sasagawa, S., Takabatake, T., Takabatake, Y., Muramatsu, T. & Takeshima, K., Improved mRNA electroporation method for Xenopus neurula embryos., Genesis 33, 81-5 (2002)). The injection of mRNA (5 ng in 5 nl solution) into the vicinity of heart anlage and the application of electric pulses were performed at stage 29. The whole mount in situ hybridization analysis of mouse IGFBP-4 was performed as the same method as that previously reported (Hosoda, T. et al., A novel myocyte-specific gene Midori promotes the differentiation of P19CL6 cells into cardiomyocytes., J Biol Chem 276, 35978-89 (2001)).

[2] Search of Novel Soluble Factor that Modulates Morphogenesis and Cell Proliferation The search of a novel soluble factor that modulates morphogenesis and cell proliferation, such as cardiac development and/or cardiomyocyte differentiation, was performed using P19CL6 cells, a mouse-derived cell line that differentiates into cardiomyocytes. The P19CL6 cells are known to differentiate into cardiomyocytes with high efficiency in the presence of 1% DMSO (Monzen, K. et al., Bone morphogenetic proteins induce cardiomyocyte differentiation through the mitogen-activated protein kinase kinase kinase TAK1 and cardiac transcription factors Csx/Nkx-2.5 and GATA-4., Mol Cell Biol 19, 7096-105 (1999)).

Specifically, the P19CL6 cells (2,000 cells/35-mm dish) were cultured in culture media conditioned by various kinds of cells in the absence of DMSO to screen the cardiogenic activity of each of the conditioned media. The extent of cardiomyocyte differentiation was assessed by immunostaining using a monoclonal antibody (MF20, Developmental Studies Hybridoma Bank) that recognizes a sarcomeric myosin heavy chain. An increased MF20-positive area indicates the cardiomyocyte differentiation of P19CL6 cells. Further, in the cultured P19CL6 cells, the expression of cardiac marker (a myosin heavy chain (αMHC), Nkx2.5, and GATA-4) genes and a cTnT protein in the heart were detected. The expression of the cardiac marker genes was detected by RT-PCR using primers for the respective genes. The expression of a β-actin gene was detected as a control. The used primers and PCR conditions are shown in Table 1 above. The cTnT protein was detected by western blotting using an anti-cTnT antibody (manufactured by Santa Cruz). As a control, actin was detected by an anti-β-actin antibody (manufactured by Sigma).

Among the several kinds of cells tested, culture media conditioned by a mouse bone marrow mesenchymal cell line OP9 induced the cardiomyocyte differentiation of P19CL6 cells without DMSO treatment (FIG. 1-a, left and middle panels). An increased MF20-positive area was accompanied by the induction of the cardiac marker genes such as αMHC, Nkx2.5, and GATA-4 and increased levels of the cTnT protein (FIG. 1-a, right panel). In contrast, culture media conditioned by COS7 cells, mouse embryonic fibroblasts, NIH3T3 cells, HeLa cells, END2 cells (visceral endoderm-like cells), neonatal rat cardiomyocytes, and neonatal rat cardiac fibroblasts did not induce the cardiomyocyte differentiation of P19CL6 cells in the absence of DMSO (FIG. 1-a and data not shown).

Based on those observations, the inventors of the present invention postulated that OP9 cells secreted a cardiogenic factor (s). In order to identify an OP9 cell-derived cardiogenic factor, cDNA clones isolated by a signal sequence trap method from an OP9 cell cDNA library (Ueno, H. et al., A stromal cell-derived membrane protein that supports hematopoietic stem cells., Nat Immunol 4, 457-63 (2003)) were tested for their cardiogenic activities by transient expression. When available, recombinant proteins were also used to confirm the results.

Among the candidate factors tested, IGFBP-4 treatment induced the cardiomyocyte differentiation of P19CL6 cells as evidenced by an increase in MF20-positive area and the induction of cardiac markers (FIG. 1-b). Further, when P19CL6 cells were cultured in OP9-conditioned media pretreated with an anti-IGFBP-4 neutralizing antibody (manufactured by R&D), the application of the anti-IGFBP-4 neutralizing antibody attenuated the efficiency of cardiomyocyte differentiation induced by the OP9-conditioned media (FIG. 1-c).

The above-mentioned results strongly suggest that IGFBP-4 is a cardiogenic factor secreted from OP9 cells.

[3] Examination on Mechanism of Cardiomyogenesis Induction by IGFBP-4

As IGFBPs have been characterized as molecules that bind to IGFs to modulate the actions of the IGFs, the inventors examined whether a cardiogenesis promoting effect of IGFBP-4 is mediated by either enhancement or inhibition of the actions of IGFs. First, P19CL6 cells were treated with a combination of an anti-IGF-I neutralizing antibody (manufactured by Sigma) and an anti-IGF-II neutralizing antibody (manufactured by Sigma) or a neutralizing antibody against an IGF type I receptor (manufactured by Oncogene). If treatment with those antibodies induces cardiomyocyte differentiation and/or increases a cardiogenic effect of IGFBP-4, the following assessment was given: the inhibition of IGF signalling by IGFBP-4 induces cardiomyocyte differentiation. On the other hand, if treatment with those antibodies attenuates IGFBP-4-induced cardiogenesis, the following assessment was given: the enhancement of IGF signalling by IGFBP-4 induces cardiomyocyte differentiation. Further, the cardiomyocyte differentiation of P19CL6 cells was tested using an IGFBP-4 mutant (IGFBP-4-H74P) that does not bind to IGFs in place of IGFBP-4.

Treatment with a combination of an anti-IGF-I neutralizing antibody and an anti-IGF-II neutralizing antibody or a neutralizing antibody against an IGF type I receptor did not have any influence on the efficiency of IGFBP-4-induced cardiomyocyte differentiation (FIG. 1-d and data not shown). Further, even treatment of P19CL6 cells with IGF-I (manufactured by R&D) and IGF-II (manufactured by R&D) did not induce cardiomyocyte differentiation (data not shown). In addition, treatment with IGFBP-4-H74P induced the cardiomyocyte differentiation of P19CL6 cells with higher efficiency than wild-type IGFBP-4 (FIG. 1-e). This is presumably because endogenous IGF causes the sequestration of wild-type IGFBP-4, but does not cause the sequestration of mutant IGFBP-4-H74P. Consistent with the results, exogenous IGF attenuated cardiogenesis induced by wild-type IGFBP-4, but did not attenuate cardiogenesis induced by IGFBP-4-H74P (FIG. 1-f).

Taken together, those observations suggest that IGFBP-4 induces cardiomyocyte differentiation in an IGF-independent fashion.

It has been showed that canonical Wnt signalling plays a crucial role in cardiomyocyte differentiation (Non-Patent References 2 and 4).

In view of the foregoing, the hypothesis that IGFBP-4 modulated canonical Wnt signalling was examined. The examination was conducted using a reporter gene TOP-FLASH (manufactured by Upstate) that allows measuring the transcription activity of a β-catenin-dependent transcription factor Tcf and FOPFLASH (manufactured by Upstate) as its negative control. First, P19CL6 cells were transfected with TOPFLASH or FOPFLASH as a reporter gene and an LRP6 or Frz8 expression vector, and treated with Wnt3A and IGFBP-4. The TOPFLASH activity was assessed by measuring a luciferase activity. Further, as a control, an effect of IGFBP-4 on a signalling pathway which is initiated by BMP2 and includes the transcription of a target gene via Smad was examined using a BMP-responsive reporter gene BRE-luc. In P19CL6 cells, Wnt3A treatment enhanced the TOPFLASH activity (FIG. 2-a). Further, the enhancement of the TOPFLASH activity with Wnt3A was further enhanced by transfection with the LRP6 or Frz8 expression vector (FIG. 2-a). On the other hand, the TOPFLASH activity enhanced by Wnt3A was attenuated by IGFBP-4 (FIG. 2-a). In the case of using FOPFLASH as the negative control, Wnt3A treatment, transfection with the LRP6 or Frz8 expression vector, and IGFBP-4 treatment did not alter any TOPFLASH activity (FIG. 5-a). Further, IGFBP-4 did not have any influence on the concentration-dependent activation of BMP-responsive BRE-luc induced by BMP2 (FIG. 5-b).

Those results revealed that IGFBP-4 inhibited a β-catenin-dependent transcription activity induced by Wnt3A treatment. In other words, the results suggested that IGFBP-4 served as an inhibitor specific for a canonical Wnt pathway.

Next, the IGFBP-4-induced inhibition of canonical Wnt pathway in vivo was examined by axis duplication assays in Xenopus embryos. Secondary axis formation was induced by the injection of Xwnt8 mRNA into Xenopus embryos, but the Xwnt8 mRNA-induced secondary axis formation was effectively inhibited by the injection of XIGFBP-4 mRNA into embryos (FIG. 2-b). Similarly, secondary axis formation was caused by the injection of LRP6 mRNA into embryos, and LRP6 mRNA-induced secondary axis formation was effectively inhibited by the injection of XIGFBP-4 mRNA into embryos (FIG. 2-c). The injection of XIGFBP-4 mRNA alone had little influences on axis formation (FIG. 2-b and FIG. 2-c).

Those results indicate that IGFBP-4 inhibits canonical Wnt signalling both in vivo and in vitro.

In order to elucidate the mechanism of IGFBP-4-induced Wnt inhibition, Xenopus cap assays and TOPFLASH reporter gene assays were performed. First, LRP6 mRNA, β-catenin mRNA, β-galactosidase mRNA, and IGFBP-4 mRNA were injected into the animal pole of Xenopus two-cell embryos in accordance with the combinations shown in FIG. 5-c. After that, animal caps were dissected from embryos at stage 85, and cultured in a Steinberg solution including 5 ng/ml activin and 0.1% bovine serum albumin until embryos reached stage 17. Next, the expression of Wnt target genes of the resultant embryos, siamois and Xnr-3 were measured. As a control, the expression of an ornithine decarboxylase (ODC) gene was measured. The TOPFLASH reporter gene assays were performed in the same manner as described above. First, P19CL6 cells were transfected with an LRP6 expression vector, a β-catenin expression vector, or a Dvl-1 expression vector, and TOP-FLASH, and treated with Wnt3A and IGFBP-4. Further, P19CL6 cells transfected with TOPFLASH alone were treated with an activator of Wnt signals lithium chloride and IGFBP-4.

In the animal cap assays, IGFBP-4 inhibited LRP6-induced Wnt target gene expression, but did not inhibit β-catenin-induced Wnt target gene expression (FIG. 5-c). Similarly, IGFBP-4 attenuated the TOPFLASH activity induced by Wnt3A or LRP6 (FIG. 5-d), but did not have any influence on the TOPFLASH activity induced by a Wnt signalling factor, Dvl-1 or 3-catenin, and the TOPFLASH activity induced by a Wnt signal activator, lithium chloride (FIG. 5-d and FIG. 5-e).

Those results suggest that IGFBP-4 inhibits canonical Wnt signalling at the level of cell surface receptors.

Next, the inventors tested whether IGFBP-4 antagonized Wnt signalling via direct physical interaction with a Wnt receptor LRP5/6 or Frizzled. First, conditioned media including LRP6N-Myc, Frz8CRD-Myc, or V5-tagged IGFBP4 (IGFBP-4-V5) were prepared using 293 cells. Then, a binding reaction of IGFBP-4-V5 with LRP6N-Myc or Frz8CRD-Myc was performed at 4° C. overnight. Binding analysis was conducted by immunoprecipitation with an anti-Myc antibody and subsequent immunoblotting with an anti-V5 antibody or an anti-Myc antibody, and by immunoprecipitation with an anti-V5 antibody and subsequent immunoblotting with an anti-Myc antibody or an anti-V5 antibody. In addition, a liquid-phase binding assay (LBR) using $^{125}$I-labelled IGFBP-4 was performed for conditioned media including LRP6N-Myc or Frz8CRD-Myc. A similar liquid-phase binding assay was performed using $^{125}$I-labelled Wnt3A to examine an effect of IGFBP-4 on the binding of Wnt3A to LRP6N-Myc or Frz8CRD-Myc.

The above-mentioned test results revealed that IGFBP-4 interacted with LRP6N (FIG. 2-d) and Frz8CRD (FIG. 2-e). Further, the liquid-phase binding assay demonstrated that the interaction between IGFBP-4 and LRP6N or between IGFBP-4 and Frz8CRD was specific and saturable (FIG. 2-f and FIG. 2-g). Scatchard plot analysis revealed that there are two binding sites with different binding affinities for LRP6N (FIG. 2-f, inset) and a single binding site for Frz8CRD (FIG. 2-g, inset). Further, the analysis also demonstrated that IGFBP-4 inhibited the binding of Wnt3A to LRP6N (FIG. 2-h) and Frz8CRD (FIG. 2-i), and a Lineweaver-Burk plot revealed that IGFBP-4 was a competitive inhibitor of the binding of Wnt3A to Frz8CDR (FIG. 6-a).

In addition, binding analyses using various deletion mutants of LRP6 and IGFBP-4 (FIG. 6-b) revealed that IGFBP-4 interacted with a large variety of domains of LRP6, and that the carboxy-terminal thyroglobulin domain of IGFBP-4 was important for the binding of IGFBP-4 to LRP6 or Frz8CRD (FIG. 6-c to FIG. 6-f).

The above-mentioned results revealed that IGFBP-4 antagonized a Wnt/β-catenin pathway through direct interactions with Frizzled and LRP5/6.

There are reports showing that the inhibition of canonical Wnt signalling promotes cardiomyocyte differentiation in ES cells and chick, Xenopus, and zebrafish embryos (Naito, A. T. et al., Developmental stage-specific biphasic roles of Wnt/beta-catenin signaling in cardiomyogenesis and hematopoiesis., Proc Natl Acad Sci USA 103, 19812-7 (2006); Tzahor, E. & Lassar, A. B., Wnt signals from the neural tube block ectopic cardiogenesis., Genes Dev 15, 255-60 (2001); Schneider, V. A. & Mercola, M., Wnt antagonism initiates cardiogenesis in Xenopus laevis., Genes Dev 15, 304-15 (2001); Marvin, M. J., Di Rocco, G., Gardiner, A., Bush, S. M. & Lassar, A. B., Inhibition of Wnt activity induces heart formation from posterior mesoderm., Genes Dev 15, 316-27 (2001); Ueno, S. et al., Biphasic role for Wnt/beta-catenin signaling in cardiac specification in zebrafish and embryonic stem cells., Proc Natl Acad Sci USA 104, 9685-90 (2007)). Thus, the above-mentioned results and previous reports suggest that IGFBP-4 promotes cardiogenesis by inhibiting canonical Wnt signalling.

[4] Elucidation of Role of Endogenous IGFBP-4 in Cardiomyocyte Differentiation

The expression of IGFBP family members in the cardiomyocyte differentiation of P19CL6 cells was examined. The cardiomyocyte differentiation of P19CL6 cells was induced by the addition of DMSO, and the expression of IGFBPs was measured by RT-PCR on day 0, day 2, day 4, day 6, and day 8 after the addition of DMSO.

This revealed that the expression of IGFBP-4 was upregulated during the cardiomyocyte differentiation of P19CL6 cells (FIG. 3-a). IGFBP-3 and IGFBP-5 were also upregulated in the early and late phases of differentiation, respectively. The expression of IGFBP-2 was not altered, and the expression of IGFBP-1 or IGFBP-6 was not detected.

Next, the effect of knockdown of IGFBP-4 in the cardiomyocyte differentiation of P19CL6 cells was examined. The knockdown of IGFBP-4 was conducted using two kinds of two independent siRNA constructs for IGFBP-4. The cardiomyocyte differentiation of P19CL6 cells was induced by the addition of DMSO, and the cardiomyocyte differentiation was assessed by the expression of cardiac marker gene (αMHC, Nkx2.5, and GATA-4) and the expression of a cTnT protein. Further, the effects of siRNA-mediated knockdown of IGFBP-3 and IGFBP-5 were similarly examined.

Any of IGFBP-4 siRNAs inhibited the DMSO-induced cardiomyocyte differentiation of P19CL6 cells (FIG. 3-b). In contrast, IGFBP-3 siRNA or IGFBP-5 siRNA did not inhibit the DMSO-induced cardiomyocyte differentiation of P19CL6 cells (FIG. 3-b, right panel).

Further, treatment with an anti-IGFBP-4 neutralizing antibody also inhibited the DMSO-induced cardiomyocyte differentiation of P19CL6 cells (FIG. 3-c).

Those results revealed that the secretion of endogenous IGFBP-4 was required for the cardiomyocyte differentiation of P19CL6 cells. In order to further elucidate the relevance between the secretion of endogenous IGFBP-4 and the cardiomyocyte differentiation of P19CL6 cells, the cardiomyocyte differentiation of P19CL6 cells stably transfected with an αMHC-GFP reporter gene was induced by DMSO, and IGFBP-4 immunostaining was performed. The IGFBP-4 immunostaining revealed that P19CL6 cells that had undergone the induction of cardiomyocyte differentiation with DMSO were surrounded by IGFBP-4-positive cells (FIG. 3-d). The results suggest that IGFBP-4 shows a paracrine effect predominantly on cardiomyocyte differentiation. In addition, an effect of IGFBP-4 on the induction of the cardiomyocyte differentiation of ES cells was similarly examined. The results were essentially the same as the examination results of an effect of IGFBP-4 on the induction of cardiomyocyte differentiation of P19CL6 cells (FIG. 7-a to FIG. 7-g). The ES cells were stably transfected with an αMHC-GFP reporter gene, and the cardiomyocyte differentiation was induced by a hanging drop method. IGFBP-4 (1 µg/ml) inhibited the cardiomyocyte differentiation of ES cells when being applied on day 0 to day 3 (D0-3), whereas it enhanced cardiogenesis when being applied on day 3 to day 5 (D3-5) (FIG. 7-a to FIG. 7-c). Further, the cardiomyocyte differentiation of ES cells was attenuated by the siRNA-mediated knockdown of IGFBP-4 and anti-IGFBP-4 antibody treatment (FIG. 7-e and FIG. 7-f). Further, in situ hybridization analysis of IGFBP-4 in mouse embryos (E95) revealed that mouse IGFBP-4 was strongly expressed in the tissues adjacent to the heart such as pharyngeal arches and liver bud in E95 (FIG. 7-h). Those results strongly support that IGFBP-4 shows a paracrine effect predominantly on myocyte differentiation. Together with a previous report (Jung, J., Zheng, M., Goldfarb, M. & Zaret, K. S., Initiation of mammalian liver development from endoderm by fibroblast growth factors., Science 284, 1998-2003 (1999)) showing that cardiac mesoderm secretes fibroblast growth factors (FGFs) and induces liver progenitors in the ventral mesoderm, those observations suggest that there are reciprocal signalling between the heart and the liver that coordinately promotes the development of each other.

Next, the inventors examined whether or not the effect of endogenous IGFBP-4 in the cardiomyocyte differentiation was mediated by the inhibition of a canonical Wnt pathway. Specifically, control P19CL6 cells and P19CL6 cells in which IGFBP-4 was knockdown by siRNAs were transfected with a GFP or LRP6N expression vector, and the cardiomyocyte differentiation was induced by DMSO treatment. LRP6N is a dominant-negative form of wild-type LRP6, and the overexpression thereof inhibits Wnt signalling. The expression of LRP6N enhanced the cardiomyocyte differentiation of P19CL6 cells, and rescued the cardiomyocyte differentiation of P19CL6 cells attenuated by the knockdown of IGFBP-4 (FIG. 3-e).

The above-mentioned observations suggest that endogenous IGFBP-4 is required for the cardiomyocyte differentiation of P19CL6 cells and ES cells, and that the cardiogenic effect of IGFBP-4 is mediated by a Wnt/β-catenin signalling inhibitory effect.

[5] Elucidation of Role of Endogenous IGFBP-4 in Cardiac Development In Vivo

The role of endogenous IGFBP-4 in cardiac development in vivo was tested using *Xenopus* embryos. First, in situ hybridization analyses of the expression of Nkx2.5 (early cardiac marker), cTnI (mature cardiac marker), Hex (liver marker), and XIGFBP-4 mRNAs at stages 34, 38, and 42 in *Xenopus* embryos were performed. As a result, the strong expression of XIGFBP-4 was detected at stage 38 in the anterior part of the liver adjacent to the heart (FIG. 4-*a*).

Next, the effect of knockdown of XIGFBP-4 by two independent morpholino (MO) constructs (FIG. 8-*a* and Table 2) in cardiogenesis was examined. Those two MOs were designed and synthesized for two XIGFBP-4 (XIGFBP-4 and XIGFBP-4d) (FIG. 8-*a*). As a result, the knockdown of XIGFBP-4 by two independent morpholino (MO) constructs resulted in cardiac defects, with 70% or more of the embryos having small heart or no heart (FIG. 4-*b*). On the other hand, the co-expression of XIGFBP-4 cDNA, IGF binding-defective XIGFBP-4 mutant (XIGFBP-4-H74P), or LRP6N as dominant-negative LRP6 rescued MO-induced cardiac defects (FIG. 4-*b*). Further, the fact that the MO used was specific for XIGFBP-4 was evident from the fact that the expression of an XIGFBP-4-Myc protein translated from MO-sensitive mRNA was attenuated by the co-injection of MO1 or MO2, whereas the expression of a protein from MO-resistant mRNA was not affected by the co-injection (FIG. 8-*b*), and the fact that the co-injection of MO-resistant XIGFBP-4 cDNA (FIG. 8-*a*) rescued MO-induced cardiac defects (FIG. 8-*c*).

Importantly, the co-expression of IGF binding-defective XIGFBP-4-H74P or dominant-negative LRP6 also rescued the cardiac defects induced by the knockdown of XIGFBP (FIG. 4-*b*), whereas the overexpression of Xwnt8 in the heart forming region resulted in cardiac defects similar to those induced by the knockdown of XIGFBP-4 (FIG. 8-*d* to FIG. 8-*f*). The fact supports the notion that the cardiogenic effect of IGFBP-4 is independent of IGFs but is mediated by the inhibition of a Wnt/β-catenin pathway.

Temporal profiles of cardiac defects induced by the knockdown of XIGFBP-4 were also tested by heart troponin I (cTnI) in situ hybridization (FIG. 4-*c*). At stage 34, the morphology of the heart was comparable between control embryos and MO-injected embryos. However, at stage 38, when XIGFBP-4 started to be expressed in the anterior part of the liver, the expression of cTnI was markedly decreased in MO-injected embryos, and the expression of cTnI was attenuated and no heart-like structure was observed at stage 42.

As described above, the heart is initially formed but the subsequent growth of the heart is perturbed in the absence of XIGFBP-4. This suggests that IGFBP-4 should promote cardiogenesis by maintaining the growth and/or survival of embryonic cardiomyocytes.

Example 2

IGFBPs comprise six members, i.e., IGFBP-1 to IGFBP-6. Wnt signalling inhibitory actions of those IGFBP family members were examined by reporter gene assays and β-catenin stabilization assays. Further, the interactions between each of the IGFBP family members with LRP6 or Frz8 were examined by IP/western analyses. The reporter gene assays, β-catenin stabilization assays, and IP/western analyses were performed by the same methods as those described in Example 1.

Among the IGFBP family members, IGFBP-4 most strongly inhibited Wnt3A-induced β-catenin expression. It was revealed that IGFBP-1, IGFBP-2, and IGFBP-6 also exhibited moderate Wnt inhibitory activities, whereas IGFBP-3 and IGFBP-5 did not exhibit such activities (FIG. 9-*a* to FIG. 9-*c*). Consistent with the results, the IP/western analyses revealed that IGFBP-1, IGFBP-2, IGFBP-4, and IGFBP-6 interacted with LRP6 or Frz8CRD, whereas IGFBP-3 and IGFBP-5 did not interact with LRP6 or Frz8CRD (FIG. 9-*d* and FIG. 9-*e*).

Those results revealed that IGFBP-1, IGFBP-2, and IGFBP-6 as well as IGFBP-4 bind to a Wnt receptor LRP6 or Frz8, to thereby inhibit Wnt signalling.

SEQUENCE LISTING FREE TEXT

SEQ ID NO: 1: A gene encoding IGFBP-4 (SEQ ID NO: 2).

SEQ ID NO: 3: A gene encoding IGFBP-1 (SEQ ID NO: 4).

SEQ ID NO: 5: A gene encoding IGFBP-2 (SEQ ID NO: 6).

SEQ ID NO: 7: A gene encoding IGFBP-6 (SEQ ID NO: 8).

SEQ ID NO: 9: A designed oligonucleotide for use as a primer.

SEQ ID NO: 10: A designed oligonucleotide for use as a primer.

SEQ ID NO: 11: A designed oligonucleotide for use as a primer.

SEQ ID NO: 12: A designed oligonucleotide for use as a primer.

SEQ ID NO: 13: A designed oligonucleotide for use as a primer.

SEQ ID NO: 14: A designed oligonucleotide for use as a primer.

SEQ ID NO: 15: A designed oligonucleotide for use as a primer.

SEQ ID NO: 16: A designed oligonucleotide for use as a primer.

SEQ ID NO: 17: A designed oligonucleotide for use as a primer.

SEQ ID NO: 18: A designed oligonucleotide for use as a primer.

SEQ ID NO: 19: A designed oligonucleotide for use as a primer.

SEQ ID NO: 20: A designed oligonucleotide for use as a primer.

SEQ ID NO: 21: A designed oligonucleotide for use as a primer.

SEQ ID NO: 22: A designed oligonucleotide for use as a primer.

SEQ ID NO: 23: A designed oligonucleotide for use as a primer.

SEQ ID NO: 24: A designed oligonucleotide for use as a primer.

SEQ ID NO: 25: A designed oligonucleotide for use as a primer.

SEQ ID NO: 26: A designed oligonucleotide for use as a primer.

SEQ ID NO: 27: A designed oligonucleotide for use as a primer.

SEQ ID NO: 28: A designed oligonucleotide for use as a primer.
SEQ ID NO: 29: A designed oligonucleotide for use as a primer.
SEQ ID NO: 30: A designed oligonucleotide for use as a primer.
SEQ ID NO: 31: A designed oligonucleotide for use as a primer.
SEQ ID NO: 32: A designed oligonucleotide for use as a primer.
SEQ ID NO: 33: A designed oligonucleotide for use as a primer.
SEQ ID NO: 34: A designed oligonucleotide for use as a primer.
SEQ ID NO: 35: A designed oligonucleotide for use as a primer.
SEQ ID NO: 36: A designed oligonucleotide for use as a primer.
SEQ ID NO: 37: A designed oligonucleotide for use as a primer.
SEQ ID NO: 38: A designed oligonucleotide for use as a siRNA.
SEQ ID NO: 39: A designed oligonucleotide for use as a siRNA.
SEQ ID NO: 40: A designed oligonucleotide for use as a siRNA.
SEQ ID NO: 41: A designed oligonucleotide for use as a siRNA.
SEQ ID NO: 42: A designed oligonucleotide for use as a morpholino.
SEQ ID NO: 43: A designed oligonucleotide for use as a morpholino.
SEQ ID NO: 44: A partial sequence of a *Xenopus* IGFBP-4 gene.
SEQ ID NO: 45: A partial sequence of a *Xenopus* IGFBP-4 variant gene.
SEQ ID NO: 46: A morpholino target sequence in a *Xenopus* IGFBP-4 gene.
SEQ ID NO: 47: A morpholino target sequence in a *Xenopus* IGFBP-4 gene.
SEQ ID NO: 48: A partial sequence of a morpholino resistant *Xenopus* IGFBP-4 gene.

The invention claimed is:

1. A method of inhibiting Wnt signalling, comprising contacting an insulin-like growth-factor-binding protein (IGFBP) with a Wnt receptor in vitro, wherein the insulin-like growth-factor-binding protein (IGFBP) is a protein represented by an amino acid sequence set forth in SEQ ID NO: 2 of Sequence Listing.

2. The method of inhibiting Wnt signalling according to claim 1, wherein the Wnt receptor is low-density lipoprotein receptor-related protein 6 (LRP6) and Frizzled 8 (Frz8).

* * * * *

SEQUENCE LISTING

```
<160> NUMBER OF SEQ ID NOS: 48

<210> SEQ ID NO 1
<211> LENGTH: 2246
<212> TYPE: DNA
<213> ORGANISM: Homo Sapiens
<220> FEATURE:
<221> NAME/KEY: CDS
<222> LOCATION: (313)..(1089)
<220> FEATURE:
<221> NAME/KEY: misc_feature
<223> OTHER INFORMATION: a gene encoding IGFBP-4 (SEQ ID NO:2)

<400> SEQUENCE: 1
aaagtccggg ggagccggtc ccgggcagcc gctcagcccc ctgcccctcg ccgcccgccg      60
cctgcctggg ccgggccgag gatgcggcgc agcgcctcgg cggccaggct tgctcccctc     120
cggcacgcct gctaacttcc cccgctacgt ccccgttcgc ccgccgggcc gccccgtctc     180
cccgcgccct ccgggtcggg tcctccagga gcgccaggcg ctgccgccgt gtgccctccg     240
ccgctcgccc gcgcgcccgc gctccccgcc tgcgcccagc gccccgcgcc cgcgcccagt     300
cctcgggcgg tc atg ctg ccc ctc tgc ctc gtg gcc gcc ctg ctg ctg gcc    351
              Met Leu Pro Leu Cys Leu Val Ala Ala Leu Leu Leu Ala
                1               5                  10 gcc ggg ccc ggg ccg agc ctg ggc gac gaa gcc atc cac tgc ccg ccc       399
Ala Gly Pro Gly Pro Ser Leu Gly Asp Glu Ala Ile His Cys Pro Pro
      15                  20                  25 tgc tcc gag gag aag ctg gcg cgc tgc cgc ccc ccc gtg ggc tgc gag       447
Cys Ser Glu Glu Lys Leu Ala Arg Cys Arg Pro Pro Val Gly Cys Glu
 30                  35                  40                  45 gag ctg gtg cga gag ccg ggc tgc ggc tgt tgc gcc act tgc gcc ctg       495
Glu Leu Val Arg Glu Pro Gly Cys Gly Cys Cys Ala Thr Cys Ala Leu
                 50                  55                  60 ggc ttg ggg atg ccc tgc ggg gtg tac acc ccc cgt tgc ggc tcg ggc       543
Gly Leu Gly Met Pro Cys Gly Val Tyr Thr Pro Arg Cys Gly Ser Gly
             65                  70                  75 ctg cgc tgc tac ccg ccc cga ggg gtg gag aag ccc ctg cac aca ctg       591
Leu Arg Cys Tyr Pro Pro Arg Gly Val Glu Lys Pro Leu His Thr Leu
         80                  85                  90
```

-continued

| | |
|---|---|
| atg cac ggg caa ggc gtg tgc atg gag ctg gcg gag atc gag gcc atc<br>Met His Gly Gln Gly Val Cys Met Glu Leu Ala Glu Ile Glu Ala Ile<br>95                         100                     105 | 639 |
| cag gaa agc ctg cag ccc tct gac aag gac gag ggt gac cac ccc aac<br>Gln Glu Ser Leu Gln Pro Ser Asp Lys Asp Glu Gly Asp His Pro Asn<br>110                       115                   120                   125 | 687 |
| aac agc ttc agc ccc tgt agc gcc cat gac cgc agg tgc ctg cag aag<br>Asn Ser Phe Ser Pro Cys Ser Ala His Asp Arg Arg Cys Leu Gln Lys<br>             130                   135                   140 | 735 |
| cac ttc gcc aaa att cga gac cgg agc acc agt ggg ggc aag atg aag<br>His Phe Ala Lys Ile Arg Asp Arg Ser Thr Ser Gly Gly Lys Met Lys<br>                   145                   150                   155 | 783 |
| gtc aat ggg gcg ccc cgg gag gat gcc cgg cct gtg ccc cag ggc tcc<br>Val Asn Gly Ala Pro Arg Glu Asp Ala Arg Pro Val Pro Gln Gly Ser<br>160                         165                     170 | 831 |
| tgc cag agc gag ctg cac cgg gcg ctg gag cgg ctg gcc gct tca cag<br>Cys Gln Ser Glu Leu His Arg Ala Leu Glu Arg Leu Ala Ala Ser Gln<br>175                       180                   185 | 879 |
| agc cgc acc cac gag gac ctc tac atc atc ccc atc ccc aac tgc gac<br>Ser Arg Thr His Glu Asp Leu Tyr Ile Ile Pro Ile Pro Asn Cys Asp<br>190                       195                   200                   205 | 927 |
| cgc aac ggc aac ttc cac ccc aag cag tgt cac cca gct ctg gat ggg<br>Arg Asn Gly Asn Phe His Pro Lys Gln Cys His Pro Ala Leu Asp Gly<br>             210                   215                   220 | 975 |
| cag cgt ggc aag tgc tgg tgt gtg gac cgg aag acg ggg gtg aag ctt<br>Gln Arg Gly Lys Cys Trp Cys Val Asp Arg Lys Thr Gly Val Lys Leu<br>                   225                   230                   235 | 1023 |
| ccg ggg ggc ctg gag cca aag ggg gag ctg gac tgc cac cag ctg gct<br>Pro Gly Gly Leu Glu Pro Lys Gly Glu Leu Asp Cys His Gln Leu Ala<br>240                         245                   250 | 1071 |
| gac agc ttt cga gag tga ggcctgccag caggccaggg actcagcgtc<br>Asp Ser Phe Arg Glu<br>    255 | 1119 |
| ccctgctact cctgtgctct ggaggctgca gagctgaccc agagtggagt ctgagtctga | 1179 |
| gtcctgtctc tgcctgcggc ccagaagttt ccctcaaatg cgcgtgtgca cgtgtgcgtg | 1239 |
| tgcgtgcgtg tgtgtgtgtt tgtgagcatg ggtgtgccct ggggtaagc cagagcctgg | 1299 |
| ggtgttctct ttggtgttac acagcccaag aggactgaga ctggcactta gcccaagagg | 1359 |
| tctgagccct ggtgtgtttc cagatcgatc ctggattcac tcactcactc attccttcac | 1419 |
| tcatccagcc acctaaaaac atttactgac catgtactac gtgccagctc tagttttcag | 1479 |
| ccttgggagg ttttattctg acttcctctg attttggcat gtggagacac tcctataagg | 1539 |
| agagttcaag cctgtgggag tagaaaaatc tcattcccag agtcagagga gaagagacat | 1599 |
| gtaccttgac catcgtcctt cctctcaagc tagccagagg gtgggagcct aaggaagcgt | 1659 |
| ggggtagcag atgagtaat ggtcacgagg tccagaccca ctcccaaagc tcagacttgc | 1719 |
| caggctccct ttctcttctt ccccaggtcc ttcctttagg tctggttgtt gcaccatctg | 1779 |
| cttggttggc tggcagctga gagccctgct gtgggagagc aagggggtc aaaggaagac | 1839 |
| ttgaagcaca gagggctagg gaggtgggt acatttctct gagcagtcag ggtgggaaga | 1899 |
| aagaatgcaa gagtggactg aatgtgccta atggagaaga cccacgtgct aggggatgag | 1959 |
| gggcttcctg ggtcctgttc cctaccccat ttgtggtcac agccatgaag tcaccgggat | 2019 |
| gaacctatcc ttccagtggc tcgctccctg tagctctgcc tccctctcca tatctccttc | 2079 |
| ccctacacct ccctccccac acctccctac tccctgggc atcttctggc ttgactggat | 2139 |

```
ggaaggagac ttaggaacct accagttggc catgatgtct ttcttctttt ttcttttttt    2199
taacaaaaca gaacaaaacc aaaaaatgtc cagatgaaaa aaaaaaa                  2246
```

<210> SEQ ID NO 2
<211> LENGTH: 258
<212> TYPE: PRT
<213> ORGANISM: Homo Sapiens

<400> SEQUENCE: 2

```
Met Leu Pro Leu Cys Leu Val Ala Ala Leu Leu Ala Ala Gly Pro
1               5                   10                  15

Gly Pro Ser Leu Gly Asp Glu Ala Ile His Cys Pro Pro Cys Ser Glu
            20                  25                  30

Glu Lys Leu Ala Arg Cys Arg Pro Val Gly Cys Glu Glu Leu Val
        35                  40                  45

Arg Glu Pro Gly Cys Gly Cys Cys Ala Thr Cys Ala Leu Gly Leu Gly
    50                  55                  60

Met Pro Cys Gly Val Tyr Thr Pro Arg Cys Gly Ser Gly Leu Arg Cys
65                  70                  75                  80

Tyr Pro Pro Arg Gly Val Glu Lys Pro Leu His Thr Leu Met His Gly
                85                  90                  95

Gln Gly Val Cys Met Glu Leu Ala Glu Ile Glu Ala Ile Gln Glu Ser
            100                 105                 110

Leu Gln Pro Ser Asp Lys Asp Glu Gly Asp His Pro Asn Asn Ser Phe
        115                 120                 125

Ser Pro Cys Ser Ala His Asp Arg Arg Cys Leu Gln Lys His Phe Ala
    130                 135                 140

Lys Ile Arg Asp Arg Ser Thr Ser Gly Gly Lys Met Lys Val Asn Gly
145                 150                 155                 160

Ala Pro Arg Glu Asp Ala Arg Pro Val Pro Gln Gly Ser Cys Gln Ser
                165                 170                 175

Glu Leu His Arg Ala Leu Glu Arg Leu Ala Ala Ser Gln Ser Arg Thr
            180                 185                 190

His Glu Asp Leu Tyr Ile Ile Pro Ile Pro Asn Cys Asp Arg Asn Gly
        195                 200                 205

Asn Phe His Pro Lys Gln Cys His Pro Ala Leu Asp Gly Gln Arg Gly
    210                 215                 220

Lys Cys Trp Cys Val Asp Arg Lys Thr Gly Val Lys Leu Pro Gly Gly
225                 230                 235                 240

Leu Glu Pro Lys Gly Glu Leu Asp Cys His Gln Leu Ala Asp Ser Phe
                245                 250                 255

Arg Glu
```

<210> SEQ ID NO 3
<211> LENGTH: 1660
<212> TYPE: DNA
<213> ORGANISM: Homo Sapiens
<220> FEATURE:
<221> NAME/KEY: CDS
<222> LOCATION: (294)..(1073)
<220> FEATURE:
<221> NAME/KEY: misc_feature
<223> OTHER INFORMATION: a gene encoding IGFBP-1 (SEQ ID NO:4)

<400> SEQUENCE: 3

```
ggtgcactag caaaacaaac ttattttgaa cactcagctc ctagcgtgcg gcgctgccaa     60
tcattaacct cctggtgcaa gtggcgcggc ctgtgccctt tataaggtgc gcgctgtgtc    120
```

```
cagcgagcat cggccaccgc catcccatcc agcgagcatc tgccgccgcg ccgccgccac        180
cctcccagag agcactggcc accgctccac catcacttgc ccagagtttg ggccaccgcc        240
cgccgccacc agcccagaga gcatcggccc ctgtctgctg ctcgcgcctg gag atg          296
                                                          Met
                                                           1 tca gag gtc ccc gtt gct cgc gtc tgg ctg gta ctg ctc ctg ctg act         344
Ser Glu Val Pro Val Ala Arg Val Trp Leu Val Leu Leu Leu Leu Thr
         5                  10                 15 gtc cag gtc ggc gtg aca gcc ggc gct ccg tgg cag tgc gcg ccc tgc         392
Val Gln Val Gly Val Thr Ala Gly Ala Pro Trp Gln Cys Ala Pro Cys
         20                 25                 30 tcc gcc gag aag ctc gcg ctc tgc ccg ccg gtg tcc gcc tcg tgc tcg         440
Ser Ala Glu Lys Leu Ala Leu Cys Pro Pro Val Ser Ala Ser Cys Ser
     35                 40                 45 gag gtc acc cgg tcc gcc ggc tgc ggc tgt tgc ccg atg tgc gcc ctg         488
Glu Val Thr Arg Ser Ala Gly Cys Gly Cys Cys Pro Met Cys Ala Leu
 50                 55                 60                 65 cct ctg ggc gcc gcg tgc ggc gtg gcg act gca cgc tgc gcc cgg gga         536
Pro Leu Gly Ala Ala Cys Gly Val Ala Thr Ala Arg Cys Ala Arg Gly
                 70                 75                 80 ctc agt tgc cgc gcg ctg ccg ggg gag cag caa cct ctg cac gcc ctc         584
Leu Ser Cys Arg Ala Leu Pro Gly Glu Gln Gln Pro Leu His Ala Leu
             85                 90                 95 acc cgc ggc caa ggc gcc tgc gtg cag gag tct gac gcc tcc gct ccc         632
Thr Arg Gly Gln Gly Ala Cys Val Gln Glu Ser Asp Ala Ser Ala Pro
         100                105                110 cat gct gca gag gca ggg agc cct gaa agc cca gag agc acg gag ata         680
His Ala Ala Glu Ala Gly Ser Pro Glu Ser Pro Glu Ser Thr Glu Ile
     115                120                125 act gag gag gag ctc ctg gat aat ttc cat ctg atg gcc cct tct gaa         728
Thr Glu Glu Glu Leu Leu Asp Asn Phe His Leu Met Ala Pro Ser Glu
130                135                140                145 gag gat cat tcc atc ctt tgg gac gcc atc agt acc tat gat ggc tcg         776
Glu Asp His Ser Ile Leu Trp Asp Ala Ile Ser Thr Tyr Asp Gly Ser
                 150                155                160 aag gct ctc cat gtc acc aac atc aaa aaa tgg aag gag ccc tgc cga         824
Lys Ala Leu His Val Thr Asn Ile Lys Lys Trp Lys Glu Pro Cys Arg
             165                170                175 ata gaa ctc tac aga gtc gta gag agt tta gcc aag gca cag gag aca         872
Ile Glu Leu Tyr Arg Val Val Glu Ser Leu Ala Lys Ala Gln Glu Thr
         180                185                190 tca gga gaa gaa att tcc aaa ttt tac ctg cca aac tgc aac aag aat         920
Ser Gly Glu Glu Ile Ser Lys Phe Tyr Leu Pro Asn Cys Asn Lys Asn
     195                200                205 gga ttt tat cac agc aga cag tgt gag aca tcc atg gat gga gag gcg         968
Gly Phe Tyr His Ser Arg Gln Cys Glu Thr Ser Met Asp Gly Glu Ala
210                215                220                225 gga ctc tgc tgg tgc gtc tac cct tgg aat ggg aag agg atc cct ggg        1016
Gly Leu Cys Trp Cys Val Tyr Pro Trp Asn Gly Lys Arg Ile Pro Gly
                 230                235                240 tct cca gag atc agg gga gac ccc aac tgc cag ata tat ttt aat gta        1064
Ser Pro Glu Ile Arg Gly Asp Pro Asn Cys Gln Ile Tyr Phe Asn Val
             245                250                255 caa aac tga aaccagatga aataatgttc tgtcacgtga aatatttaag               1113
Gln Asn tatatagtat atttatactc tagaacatgc acatttatat atatatgtat atgtatatat      1173
atatagtaac tacttttat actccataca taacttgata tagaaagctg tttatttatt       1233
```

```
cactgtaagt ttatttttc tacacagtaa aaacttgtac tatgttaata acttgtccta    1293
tgtcaatttg tatatcatga aacacttctc atcatattgt atgtaagtaa ttgcatttct    1353
gctcttccaa agctcctgcg tctgttttta aagagcatgg aaaaatactg cctagaaaat    1413
gcaaaatgaa ataagagaga gtagttttc agctagtttg aaggaggacg gttaacttgt    1473
atattccacc attcacattt gatgtacatg tgtagggaaa gttaaaagtg ttgattacat    1533
aatcaaagct acctgtggtg atgttgccac ctgttaaaat gtacactgga tatgttgtta    1593
aacacgtgtc tataatggaa acatttacaa taaatattct gcatggaaat actgttaaaa    1653
aaaaaaa                                                               1660
```

<210> SEQ ID NO 4
<211> LENGTH: 259
<212> TYPE: PRT
<213> ORGANISM: Homo Sapiens

<400> SEQUENCE: 4

```
Met Ser Glu Val Pro Val Ala Arg Val Trp Leu Val Leu Leu Leu Leu
1               5                   10                  15

Thr Val Gln Val Gly Val Thr Ala Gly Ala Pro Trp Gln Cys Ala Pro
            20                  25                  30

Cys Ser Ala Glu Lys Leu Ala Leu Cys Pro Pro Val Ser Ala Ser Cys
        35                  40                  45

Ser Glu Val Thr Arg Ser Ala Gly Cys Gly Cys Cys Pro Met Cys Ala
    50                  55                  60

Leu Pro Leu Gly Ala Ala Cys Gly Val Ala Thr Ala Arg Cys Ala Arg
65                  70                  75                  80

Gly Leu Ser Cys Arg Ala Leu Pro Gly Glu Gln Gln Pro Leu His Ala
                85                  90                  95

Leu Thr Arg Gly Gln Gly Ala Cys Val Gln Glu Ser Asp Ala Ser Ala
            100                 105                 110

Pro His Ala Ala Glu Ala Gly Ser Pro Glu Ser Pro Glu Ser Thr Glu
        115                 120                 125

Ile Thr Glu Glu Glu Leu Leu Asp Asn Phe His Leu Met Ala Pro Ser
    130                 135                 140

Glu Glu Asp His Ser Ile Leu Trp Asp Ala Ile Ser Thr Tyr Asp Gly
145                 150                 155                 160

Ser Lys Ala Leu His Val Thr Asn Ile Lys Lys Trp Lys Glu Pro Cys
                165                 170                 175

Arg Ile Glu Leu Tyr Arg Val Val Glu Ser Leu Ala Lys Ala Gln Glu
            180                 185                 190

Thr Ser Gly Glu Glu Ile Ser Lys Phe Tyr Leu Pro Asn Cys Asn Lys
        195                 200                 205

Asn Gly Phe Tyr His Ser Arg Gln Cys Glu Thr Ser Met Asp Gly Glu
    210                 215                 220

Ala Gly Leu Cys Trp Cys Val Tyr Pro Trp Asn Gly Lys Arg Ile Pro
225                 230                 235                 240

Gly Ser Pro Glu Ile Arg Gly Asp Pro Asn Cys Gln Ile Tyr Phe Asn
                245                 250                 255

Val Gln Asn
```

<210> SEQ ID NO 5
<211> LENGTH: 1439
<212> TYPE: DNA
<213> ORGANISM: Homo Sapiens

```
<220> FEATURE:
<221> NAME/KEY: CDS
<222> LOCATION: (121)..(1107)
<220> FEATURE:
<221> NAME/KEY: misc_feature
<223> OTHER INFORMATION: a gene encoding IGFBP-2 (SEQ ID NO:6)

<400> SEQUENCE: 5
tgcggcggcg agggaggagg aagaagcgga ggaggcggct cccgcgctcg cagggccgtg      60
ccacctgccc gcccgcccgc tcgctcgctc gcccgccgcg ccgcgctgcc gaccgccagc     120 atg ctg ccg aga gtg ggc tgc ccc gcg ctg ccg ctg ccg ccg ccg          168
Met Leu Pro Arg Val Gly Cys Pro Ala Leu Pro Leu Pro Pro Pro
1               5                   10                  15 ctg ctg ccg ctg ctg ccg ctg ctg ctg cta ctg ggc gcg agt ggc          216
Leu Leu Pro Leu Leu Pro Leu Leu Leu Leu Leu Gly Ala Ser Gly
                20                  25                  30 ggc ggc ggc ggg gcg cgc gcg gag gtg ctg ttc cgc tgc ccg ccc tgc      264
Gly Gly Gly Gly Ala Arg Ala Glu Val Leu Phe Arg Cys Pro Pro Cys
        35                  40                  45 aca ccc gag cgc ctg gcc gcc tgc ggg ccc ccg ccg gtt gcg ccg ccc      312
Thr Pro Glu Arg Leu Ala Ala Cys Gly Pro Pro Pro Val Ala Pro Pro
    50                  55                  60 gcc gcg gtg gcc gca gtg gcc gga ggc gcc cgc atg cca tgc gcg gag      360
Ala Ala Val Ala Ala Val Ala Gly Gly Ala Arg Met Pro Cys Ala Glu
65                  70                  75                  80 ctc gtc cgg gag ccg ggc tgc ggc tgc tgc tcg gtg tgc gcc cgg ctg      408
Leu Val Arg Glu Pro Gly Cys Gly Cys Cys Ser Val Cys Ala Arg Leu
                85                  90                  95 gag ggc gag gcg tgc ggc gtc tac acc ccg cgc tgc ggc cag ggg ctg      456
Glu Gly Glu Ala Cys Gly Val Tyr Thr Pro Arg Cys Gly Gln Gly Leu
            100                 105                 110 cgc tgc tat ccc cac ccg ggc tcc gag ctg ccc ctg cag gcg ctg gtc      504
Arg Cys Tyr Pro His Pro Gly Ser Glu Leu Pro Leu Gln Ala Leu Val
        115                 120                 125 atg ggc gag ggc act tgt gag aag cgc cgg gac gcc gag tat ggc gcc      552
Met Gly Glu Gly Thr Cys Glu Lys Arg Arg Asp Ala Glu Tyr Gly Ala
    130                 135                 140 agc ccg gag cag gtt gca gac aat ggc gat gac cac tca gaa gga ggc      600
Ser Pro Glu Gln Val Ala Asp Asn Gly Asp Asp His Ser Glu Gly Gly
145                 150                 155                 160 ctg gtg gag aac cac gtg gac agc acc atg aac atg ttg ggc ggg gga      648
Leu Val Glu Asn His Val Asp Ser Thr Met Asn Met Leu Gly Gly Gly
                165                 170                 175 ggc agt gct ggc cgg aag ccc ctc aag tcg ggt atg aag gag ctg gcc      696
Gly Ser Ala Gly Arg Lys Pro Leu Lys Ser Gly Met Lys Glu Leu Ala
            180                 185                 190 gtg ttc cgg gag aag gtc act gag cag cac cgg cag atg ggc aag ggt      744
Val Phe Arg Glu Lys Val Thr Glu Gln His Arg Gln Met Gly Lys Gly
        195                 200                 205 ggc aag cat cac ctt ggc ctg gag gag ccc aag aag ctg cga cca ccc      792
Gly Lys His His Leu Gly Leu Glu Glu Pro Lys Lys Leu Arg Pro Pro
    210                 215                 220 cct gcc agg act ccc tgc caa cag gaa ctg gac cag gtc ctg gag cgg      840
Pro Ala Arg Thr Pro Cys Gln Gln Glu Leu Asp Gln Val Leu Glu Arg
225                 230                 235                 240 atc tcc acc atg cgc ctt ccg gat gag cgg ggc cct ctg gag cac ctc      888
Ile Ser Thr Met Arg Leu Pro Asp Glu Arg Gly Pro Leu Glu His Leu
                245                 250                 255
```

```
tac tcc ctg cac atc ccc aac tgt gac aag cat ggc ctg tac aac ctc     936
Tyr Ser Leu His Ile Pro Asn Cys Asp Lys His Gly Leu Tyr Asn Leu
        260                 265                 270 aaa cag tgc aag atg tct ctg aac ggg cag cgt ggg gag tgc tgg tgt     984
Lys Gln Cys Lys Met Ser Leu Asn Gly Gln Arg Gly Glu Cys Trp Cys
        275                 280                 285 gtg aac ccc aac acc ggg aag ctg atc cag gga gcc ccc acc atc cgg    1032
Val Asn Pro Asn Thr Gly Lys Leu Ile Gln Gly Ala Pro Thr Ile Arg
        290                 295                 300 ggg gac ccc gag tgt cat ctc ttc tac aat gag cag cag gag gct cgc    1080
Gly Asp Pro Glu Cys His Leu Phe Tyr Asn Glu Gln Gln Glu Ala Arg
305                 310                 315                 320 ggg gtg cac acc cag cgg atg cag tag accgcagcca gccggtgcct          1127
Gly Val His Thr Gln Arg Met Gln
                    325 ggcgcccctg ccccccgccc ctctccaaac accggcagaa aacggagagt gcttgggtgg  1187 tgggtgctgg aggattttcc agttctgaca cacgtattta tatttggaaa gagaccagca  1247 ccgagctcgg cacctccccg gcctctctct tcccagctgc agatgccaca cctgctcctt  1307 cttgctttcc ccgggggagg aaggggggttg tggtcgggga gctggggtac aggtttgggg  1367 agggggaaga gaaattttta tttttgaacc cctgtgtccc ttttgcataa gattaaagga  1427 aggaaaagta aa                                                      1439

<210> SEQ ID NO 6
<211> LENGTH: 328
<212> TYPE: PRT
<213> ORGANISM: Homo Sapiens

<400> SEQUENCE: 6

Met Leu Pro Arg Val Gly Cys Pro Ala Leu Pro Leu Pro Pro Pro
1               5                   10                  15

Leu Leu Pro Leu Leu Pro Leu Leu Leu Leu Leu Gly Ala Ser Gly
                20                  25                  30

Gly Gly Gly Gly Ala Arg Ala Glu Val Leu Phe Arg Cys Pro Pro Cys
            35                  40                  45

Thr Pro Glu Arg Leu Ala Ala Cys Gly Pro Pro Val Ala Pro Pro
        50                  55                  60

Ala Ala Val Ala Ala Val Ala Gly Gly Ala Arg Met Pro Cys Ala Glu
65                  70                  75                  80

Leu Val Arg Glu Pro Gly Cys Gly Cys Cys Ser Val Cys Ala Arg Leu
                85                  90                  95

Glu Gly Glu Ala Cys Gly Val Tyr Thr Pro Arg Cys Gly Gln Gly Leu
                100                 105                 110

Arg Cys Tyr Pro His Pro Gly Ser Glu Leu Pro Leu Gln Ala Leu Val
            115                 120                 125

Met Gly Glu Gly Thr Cys Glu Lys Arg Arg Asp Ala Glu Tyr Gly Ala
        130                 135                 140

Ser Pro Glu Gln Val Ala Asp Asn Gly Asp Asp His Ser Glu Gly Gly
145                 150                 155                 160

Leu Val Glu Asn His Val Asp Ser Thr Met Asn Met Leu Gly Gly Gly
                165                 170                 175

Gly Ser Ala Gly Arg Lys Pro Leu Lys Ser Gly Met Lys Glu Leu Ala
            180                 185                 190

Val Phe Arg Glu Lys Val Thr Glu Gln His Arg Gln Met Gly Lys Gly
        195                 200                 205
```

-continued

```
Gly Lys His His Leu Gly Leu Glu Glu Pro Lys Lys Leu Arg Pro Pro
    210                 215                 220

Pro Ala Arg Thr Pro Cys Gln Gln Glu Leu Asp Gln Val Leu Glu Arg
225                 230                 235                 240

Ile Ser Thr Met Arg Leu Pro Asp Glu Arg Gly Pro Leu Glu His Leu
                245                 250                 255

Tyr Ser Leu His Ile Pro Asn Cys Asp Lys His Gly Leu Tyr Asn Leu
            260                 265                 270

Lys Gln Cys Lys Met Ser Leu Asn Gly Gln Arg Gly Glu Cys Trp Cys
        275                 280                 285

Val Asn Pro Asn Thr Gly Lys Leu Ile Gln Gly Ala Pro Thr Ile Arg
    290                 295                 300

Gly Asp Pro Glu Cys His Leu Phe Tyr Asn Glu Gln Gln Glu Ala Arg
305                 310                 315                 320

Gly Val His Thr Gln Arg Met Gln
                325

<210> SEQ ID NO 7
<211> LENGTH: 980
<212> TYPE: DNA
<213> ORGANISM: Homo Sapiens
<220> FEATURE:
<221> NAME/KEY: CDS
<222> LOCATION: (67)..(789)
<220> FEATURE:
<221> NAME/KEY: misc_feature
<223> OTHER INFORMATION: a gene encoding IGFBP-6 (SEQ ID NO:8)

<400> SEQUENCE: 7
gcggcggcgg gcagcagctg cgctgcgact gctctggaag gagaggacgg ggcacaaacc    60 ctgacc atg acc ccc cac agg ctg ctg cca ccg ctg ctg ctg ctg cta    108
       Met Thr Pro His Arg Leu Leu Pro Pro Leu Leu Leu Leu Leu
       1               5                   10 gct ctg ctg ctc gct gcc agc cca gga ggc gcc ttg gcg cgg tgc cca    156
Ala Leu Leu Leu Ala Ala Ser Pro Gly Gly Ala Leu Ala Arg Cys Pro
15                  20                  25                  30 ggc tgc ggg caa ggg gtg cag gcg ggt tgt cca ggg ggc tgc gtg gag    204
Gly Cys Gly Gln Gly Val Gln Ala Gly Cys Pro Gly Gly Cys Val Glu
                35                  40                  45 gag gag gat ggg ggg tcg cca gcc gag ggc tgc gcg gaa gct gag ggc    252
Glu Glu Asp Gly Gly Ser Pro Ala Glu Gly Cys Ala Glu Ala Glu Gly
            50                  55                  60 tgt ctc agg agg gag ggg cag gag tgc ggg gtc tac acc cct aac tgc    300
Cys Leu Arg Arg Glu Gly Gln Glu Cys Gly Val Tyr Thr Pro Asn Cys
        65                  70                  75 gcc cca gga ctg cag tgc cat ccg ccc aag gac gac gag gcc cct ttg    348
Ala Pro Gly Leu Gln Cys His Pro Pro Lys Asp Asp Glu Ala Pro Leu
80                  85                  90 cgg gcg ctg ctc ctc ggc cga ggc cgc tgc ctt ccg gcc cgc gcg cct    396
Arg Ala Leu Leu Leu Gly Arg Gly Arg Cys Leu Pro Ala Arg Ala Pro
95                  100                 105                 110 gct gtt gca gag gag aat cct aag gag agt aaa ccc caa gca ggc act    444
Ala Val Ala Glu Glu Asn Pro Lys Glu Ser Lys Pro Gln Ala Gly Thr
                115                 120                 125 gcc cgc cca cag gat gtg aac cgc aga gac caa cag agg aat cca ggc    492
Ala Arg Pro Gln Asp Val Asn Arg Arg Asp Gln Gln Arg Asn Pro Gly
            130                 135                 140 acc tct acc acg ccc tcc cag ccc aat tct gcg ggt gtc caa gac act    540
Thr Ser Thr Thr Pro Ser Gln Pro Asn Ser Ala Gly Val Gln Asp Thr
145                 150                 155
```

-continued

| | | |
|---|---|---|
| gag atg ggc cca tgc cgt aga cat ctg gac tca gtg ctg cag caa ctc<br>Glu Met Gly Pro Cys Arg Arg His Leu Asp Ser Val Leu Gln Gln Leu<br>160                  165                    170 | | 588 |
| cag act gag gtc tac cga ggg gct caa aca ctc tac gtg ccc aat tgt<br>Gln Thr Glu Val Tyr Arg Gly Ala Gln Thr Leu Tyr Val Pro Asn Cys<br>175                  180                   185                  190 | | 636 |
| gac cat cga ggc ttc tac cgg aag cgg cag tgc cgc tcc tcc cag ggg<br>Asp His Arg Gly Phe Tyr Arg Lys Arg Gln Cys Arg Ser Ser Gln Gly<br>                  195                   200                  205 | | 684 |
| cag cgc cga ggt ccc tgc tgg tgt gtg gat cgg atg ggc aag tcc ctg<br>Gln Arg Arg Gly Pro Cys Trp Cys Val Asp Arg Met Gly Lys Ser Leu<br>              210                   215                  220 | | 732 |
| cca ggg tct cca gat ggc aat gga agc tcc tcc tgc ccc act ggg agt<br>Pro Gly Ser Pro Asp Gly Asn Gly Ser Ser Ser Cys Pro Thr Gly Ser<br>        225                   230                  235 | | 780 |
| agc ggc taa agctggggga tagaggggct gcagggccac tggaaggaac<br>Ser Gly<br>    240 | | 829 |
| atggagctgt catcactcaa caaaaaaccg aggccctcaa tccaccttca ggccccgccc | | 889 |
| catgggcccc tcaccgctgg ttggaaagag tgttggtgtt ggctggggtg tcaataaagc | | 949 |
| tgtgcttggg gtcgctgaaa aaaaaaaaaa a | | 980 |

<210> SEQ ID NO 8
<211> LENGTH: 240
<212> TYPE: PRT
<213> ORGANISM: Homo Sapiens

<400> SEQUENCE: 8

Met Thr Pro His Arg Leu Leu Pro Pro Leu Leu Leu Leu Leu Ala Leu
1                   5                    10                  15

Leu Leu Ala Ala Ser Pro Gly Gly Ala Leu Ala Arg Cys Pro Gly Cys
                20                    25                    30

Gly Gln Gly Val Gln Ala Gly Cys Pro Gly Gly Cys Val Glu Glu Glu
          35                    40                    45

Asp Gly Gly Ser Pro Ala Glu Gly Cys Ala Glu Ala Glu Gly Cys Leu
    50                    55                    60

Arg Arg Glu Gly Gln Glu Cys Gly Val Tyr Thr Pro Asn Cys Ala Pro
65                   70                    75                  80

Gly Leu Gln Cys His Pro Pro Lys Asp Asp Glu Ala Pro Leu Arg Ala
                85                    90                    95

Leu Leu Leu Gly Arg Gly Arg Cys Leu Pro Ala Arg Ala Pro Ala Val
                100                   105                 110

Ala Glu Glu Asn Pro Lys Glu Ser Lys Pro Gln Ala Gly Thr Ala Arg
        115                    120                  125

Pro Gln Asp Val Asn Arg Arg Asp Gln Gln Arg Asn Pro Gly Thr Ser
    130                    135                  140

Thr Thr Pro Ser Gln Pro Asn Ser Ala Gly Val Gln Asp Thr Glu Met
145                  150                  155                160

Gly Pro Cys Arg Arg His Leu Asp Ser Val Leu Gln Gln Leu Gln Thr
                165                   170                 175

Glu Val Tyr Arg Gly Ala Gln Thr Leu Tyr Val Pro Asn Cys Asp His
        180                    185                  190

Arg Gly Phe Tyr Arg Lys Arg Gln Cys Arg Ser Ser Gln Gly Gln Arg
    195                    200                  205

```
Arg Gly Pro Cys Trp Cys Val Asp Arg Met Gly Lys Ser Leu Pro Gly
    210                 215                 220

Ser Pro Asp Gly Asn Gly Ser Ser Ser Cys Pro Thr Gly Ser Ser Gly
225                 230                 235                 240

<210> SEQ ID NO 9
<211> LENGTH: 23
<212> TYPE: DNA
<213> ORGANISM: artificial
<220> FEATURE:
<223> OTHER INFORMATION: designed oligonucleotide for use as a primer

<400> SEQUENCE: 9
ggaagagtga gcggccatca agg                                          23

<210> SEQ ID NO 10
<211> LENGTH: 22
<212> TYPE: DNA
<213> ORGANISM: artificial
<220> FEATURE:
<223> OTHER INFORMATION: designed oligonucleotide for use as a primer

<400> SEQUENCE: 10
ctgctggaga ggttattcct cg                                           22

<210> SEQ ID NO 11
<211> LENGTH: 20
<212> TYPE: DNA
<213> ORGANISM: artificial
<220> FEATURE:
<223> OTHER INFORMATION: designed oligonucleotide for use as a primer

<400> SEQUENCE: 11
cagtggagct ggacaaagcc                                              20

<210> SEQ ID NO 12
<211> LENGTH: 20
<212> TYPE: DNA
<213> ORGANISM: artificial
<220> FEATURE:
<223> OTHER INFORMATION: designed oligonucleotide for use as a primer

<400> SEQUENCE: 12
tagcgacggt tctggaattt                                              20

<210> SEQ ID NO 13
<211> LENGTH: 20
<212> TYPE: DNA
<213> ORGANISM: artificial
<220> FEATURE:
<223> OTHER INFORMATION: designed oligonucleotide for use as a primer

<400> SEQUENCE: 13
ctgtcatctc actatgggca                                              20

<210> SEQ ID NO 14
<211> LENGTH: 20
<212> TYPE: DNA
<213> ORGANISM: artificial
<220> FEATURE:
<223> OTHER INFORMATION: designed oligonucleotide for use as a primer

<400> SEQUENCE: 14
ccaagtccga gcaggaattt                                              20
```

```
<210> SEQ ID NO 15
<211> LENGTH: 20
<212> TYPE: DNA
<213> ORGANISM: artificial
<220> FEATURE:
<223> OTHER INFORMATION: designed oligonucleotide for use as a primer

<400> SEQUENCE: 15
ggacctggct ggccgggacc                                                   20

<210> SEQ ID NO 16
<211> LENGTH: 20
<212> TYPE: DNA
<213> ORGANISM: artificial
<220> FEATURE:
<223> OTHER INFORMATION: designed oligonucleotide for use as a primer

<400> SEQUENCE: 16
gcggtgcacg atggaggggc                                                   20

<210> SEQ ID NO 17
<211> LENGTH: 22
<212> TYPE: DNA
<213> ORGANISM: artificial
<220> FEATURE:
<223> OTHER INFORMATION: designed oligonucleotide for use as a primer

<400> SEQUENCE: 17
ccagggatcc agctgccgtg cg                                                22

<210> SEQ ID NO 18
<211> LENGTH: 21
<212> TYPE: DNA
<213> ORGANISM: artificial
<220> FEATURE:
<223> OTHER INFORMATION: designed oligonucleotide for use as a primer

<400> SEQUENCE: 18
ggcgttccac aggatgggct g                                                 21

<210> SEQ ID NO 19
<211> LENGTH: 21
<212> TYPE: DNA
<213> ORGANISM: artificial
<220> FEATURE:
<223> OTHER INFORMATION: designed oligonucleotide for use as a primer

<400> SEQUENCE: 19
caactgtgac aagcatggcc g                                                 21

<210> SEQ ID NO 20
<211> LENGTH: 21
<212> TYPE: DNA
<213> ORGANISM: artificial
<220> FEATURE:
<223> OTHER INFORMATION: designed oligonucleotide for use as a primer

<400> SEQUENCE: 20
caccagtctc ctgctgctcg t                                                 21

<210> SEQ ID NO 21
<211> LENGTH: 21
<212> TYPE: DNA
<213> ORGANISM: artificial
<220> FEATURE:
<223> OTHER INFORMATION: designed oligonucleotide for use as a primer
```

<400> SEQUENCE: 21
gacacccaga acttctcctc c                                              21

<210> SEQ ID NO 22
<211> LENGTH: 21
<212> TYPE: DNA
<213> ORGANISM: artificial
<220> FEATURE:
<223> OTHER INFORMATION: designed oligonucleotide for use as a primer

<400> SEQUENCE: 22
catacttgtc cacacaccag c                                              21

<210> SEQ ID NO 23
<211> LENGTH: 22
<212> TYPE: DNA
<213> ORGANISM: artificial
<220> FEATURE:
<223> OTHER INFORMATION: designed oligonucleotide for use as a primer

<400> SEQUENCE: 23
cgtcctgtgc cccagggttc ct                                             22

<210> SEQ ID NO 24
<211> LENGTH: 22
<212> TYPE: DNA
<213> ORGANISM: artificial
<220> FEATURE:
<223> OTHER INFORMATION: designed oligonucleotide for use as a primer

<400> SEQUENCE: 24
gaagcttcac ccctgtcttc cg                                             22

<210> SEQ ID NO 25
<211> LENGTH: 22
<212> TYPE: DNA
<213> ORGANISM: artificial
<220> FEATURE:
<223> OTHER INFORMATION: designed oligonucleotide for use as a primer

<400> SEQUENCE: 25
gtttgcctca acgaaaagag ct                                             22

<210> SEQ ID NO 26
<211> LENGTH: 23
<212> TYPE: DNA
<213> ORGANISM: artificial
<220> FEATURE:
<223> OTHER INFORMATION: designed oligonucleotide for use as a primer

<400> SEQUENCE: 26
ctgctttctc ttgtagaatc ctt                                            23

<210> SEQ ID NO 27
<211> LENGTH: 21
<212> TYPE: DNA
<213> ORGANISM: artificial
<220> FEATURE:
<223> OTHER INFORMATION: designed oligonucleotide for use as a primer

<400> SEQUENCE: 27
ccccgagaga acgaagagac g                                              21

```
<210> SEQ ID NO 28
<211> LENGTH: 21
<212> TYPE: DNA
<213> ORGANISM: artificial
<220> FEATURE:
<223> OTHER INFORMATION: designed oligonucleotide for use as a primer

<400> SEQUENCE: 28
ctgcgaggaa cgacactgct g                                              21

<210> SEQ ID NO 29
<211> LENGTH: 22
<212> TYPE: DNA
<213> ORGANISM: artificial
<220> FEATURE:
<223> OTHER INFORMATION: designed oligonucleotide for use as a primer

<400> SEQUENCE: 29
caaactcatt catctccagc cc                                             22

<210> SEQ ID NO 30
<211> LENGTH: 22
<212> TYPE: DNA
<213> ORGANISM: artificial
<220> FEATURE:
<223> OTHER INFORMATION: designed oligonucleotide for use as a primer

<400> SEQUENCE: 30
ttcctttccc ctctcagatg cc                                             22

<210> SEQ ID NO 31
<211> LENGTH: 25
<212> TYPE: DNA
<213> ORGANISM: artificial
<220> FEATURE:
<223> OTHER INFORMATION: designed oligonucleotide for use as a primer

<400> SEQUENCE: 31
atgtcaggtt actgtcatcc tgccc                                          25

<210> SEQ ID NO 32
<211> LENGTH: 20
<212> TYPE: DNA
<213> ORGANISM: artificial
<220> FEATURE:
<223> OTHER INFORMATION: designed oligonucleotide for use as a primer

<400> SEQUENCE: 32
taccgcactg actctgcaag                                                20

<210> SEQ ID NO 33
<211> LENGTH: 20
<212> TYPE: DNA
<213> ORGANISM: artificial
<220> FEATURE:
<223> OTHER INFORMATION: designed oligonucleotide for use as a primer

<400> SEQUENCE: 33
ctgaggctcc tgtggaattc                                                20

<210> SEQ ID NO 34
<211> LENGTH: 18
<212> TYPE: DNA
<213> ORGANISM: artificial
<220> FEATURE:
<223> OTHER INFORMATION: designed oligonucleotide for use as a primer
```

```
<400> SEQUENCE: 34
cttctgcact agattctg                                                   18

<210> SEQ ID NO 35
<211> LENGTH: 18
<212> TYPE: DNA
<213> ORGANISM: artificial
<220> FEATURE:
<223> OTHER INFORMATION: designed oligonucleotide for use as a primer

<400> SEQUENCE: 35
cagcttctgg ccaagact                                                   18

<210> SEQ ID NO 36
<211> LENGTH: 23
<212> TYPE: DNA
<213> ORGANISM: artificial
<220> FEATURE:
<223> OTHER INFORMATION: designed oligonucleotide for use as a primer

<400> SEQUENCE: 36
gtcaatgatg gagtgtatgg atc                                             23

<210> SEQ ID NO 37
<211> LENGTH: 22
<212> TYPE: DNA
<213> ORGANISM: artificial
<220> FEATURE:
<223> OTHER INFORMATION: designed oligonucleotide for use as a primer

<400> SEQUENCE: 37
tccaatccgc tctcctgagc ac                                              22

<210> SEQ ID NO 38
<211> LENGTH: 19
<212> TYPE: DNA
<213> ORGANISM: artificial
<220> FEATURE:
<223> OTHER INFORMATION: designed oligonucleotide for use as a siRNA

<400> SEQUENCE: 38
aatcctagat gaagtgtta                                                  19

<210> SEQ ID NO 39
<211> LENGTH: 19
<212> TYPE: DNA
<213> ORGANISM: artificial
<220> FEATURE:
<223> OTHER INFORMATION: designed oligonucleotide for use as a siRNA

<400> SEQUENCE: 39
gagccaggct gcggttgtt                                                  19

<210> SEQ ID NO 40
<211> LENGTH: 19
<212> TYPE: DNA
<213> ORGANISM: artificial
<220> FEATURE:
<223> OTHER INFORMATION: designed oligonucleotide for use as a siRNA

<400> SEQUENCE: 40
gcaagtgctg gtgtgtgga                                                  19
```

```
<210> SEQ ID NO 41
<211> LENGTH: 19
<212> TYPE: DNA
<213> ORGANISM: artificial
<220> FEATURE:
<223> OTHER INFORMATION: designed oligonucleotide for use as a siRNA

<400> SEQUENCE: 41
aaggcctcca agctaatta                                                    19

<210> SEQ ID NO 42
<211> LENGTH: 25
<212> TYPE: DNA
<213> ORGANISM: artificial
<220> FEATURE:
<223> OTHER INFORMATION: designed oligonucleotide for use as a
      morpholino

<400> SEQUENCE: 42
gcagggtggc aatatccaga catga                                             25

<210> SEQ ID NO 43
<211> LENGTH: 25
<212> TYPE: DNA
<213> ORGANISM: artificial
<220> FEATURE:
<223> OTHER INFORMATION: designed oligonucleotide for use as a
      morpholino

<400> SEQUENCE: 43
cttgctgggc tggagatgaa tgagt                                             25

<210> SEQ ID NO 44
<211> LENGTH: 71
<212> TYPE: DNA
<213> ORGANISM: Xenopus laevis
<220> FEATURE:
<221> NAME/KEY: misc_feature
<223> OTHER INFORMATION: partial sequence of Xenopus IGFBP-4 gene

<400> SEQUENCE: 44
caaactcatt catctccagc ccagcaagtc acctaaacgt catgtctgga tattgccacc       60
ctgccctttt g                                                            71

<210> SEQ ID NO 45
<211> LENGTH: 71
<212> TYPE: DNA
<213> ORGANISM: Xenopus laevis
<220> FEATURE:
<221> NAME/KEY: misc_feature
<223> OTHER INFORMATION: partial sequence of Xenopus IGFBP-4 variant
      gene

<400> SEQUENCE: 45
cccactcatt catctccagc ccagcaagtc acctaaacat catgtctgga tattgccacc       60
ctgcccttct g                                                            71

<210> SEQ ID NO 46
<211> LENGTH: 25
<212> TYPE: DNA
<213> ORGANISM: Xenopus laevis
<220> FEATURE:
<221> NAME/KEY: misc_feature
<223> OTHER INFORMATION: morpholino target sequence in Xenopus IGFBP-4
      gene
```

```
<400> SEQUENCE: 46
tcatgtctgg atattgccac cctgc                                              25

<210> SEQ ID NO 47
<211> LENGTH: 25
<212> TYPE: DNA
<213> ORGANISM: Xenopus laevis
<220> FEATURE:
<221> NAME/KEY: misc_feature
<223> OTHER INFORMATION: morpholino target sequence in Xenopus IGFBP-4
      gene

<400> SEQUENCE: 47
actcattcat ctccagccca gcaag                                              25

<210> SEQ ID NO 48
<211> LENGTH: 30
<212> TYPE: DNA
<213> ORGANISM: artificial
<220> FEATURE:
<223> OTHER INFORMATION: partial sequence of morpholino resistant
      XIGFBP-4 gene

<400> SEQUENCE: 48
atgtcaggtt actgtcatcc tgccctttg                                          30
```